US 9,576,362 B2

(12) United States Patent
Yaguchi

(10) Patent No.: US 9,576,362 B2
(45) Date of Patent: *Feb. 21, 2017

(54) IMAGE PROCESSING DEVICE, INFORMATION STORAGE DEVICE, AND PROCESSING METHOD TO ACQUIRE A SUMMARY IMAGE SEQUENCE

(71) Applicant: OLYMPUS CORPORATION, Shibuya-ku, Tokyo (JP)

(72) Inventor: Yoichi Yaguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 125 days.

This patent is subject to a terminal disclaimer.

(21) Appl. No.: 14/479,235

(22) Filed: Sep. 5, 2014

(65) Prior Publication Data
US 2014/0376817 A1 Dec. 25, 2014

Related U.S. Application Data

(63) Continuation of application No. PCT/JP2013/056271, filed on Mar. 7, 2013.

(30) Foreign Application Priority Data

Mar. 7, 2012 (JP) ................................. 2012-050860
Apr. 18, 2012 (JP) ................................. 2012-094691
May 23, 2012 (JP) ................................. 2012-117318

(51) Int. Cl.
*G06K 9/00* (2006.01)
*G06T 7/00* (2006.01)
(Continued)

(52) U.S. Cl.
CPC ............ *G06T 7/003* (2013.01); *A61B 1/00009* (2013.01); *G06F 19/321* (2013.01);
(Continued)

(58) Field of Classification Search
CPC .............. A61B 1/00009; G06F 19/321; G06K 9/00751; G06K 9/68
See application file for complete search history.

(56) References Cited

U.S. PATENT DOCUMENTS 6,697,523 B1  2/2004  Divakaran et al.
7,110,454 B1  9/2006  Chakraborty
(Continued)

FOREIGN PATENT DOCUMENTS

CN  102096917 A  * 12/2010
CN  102096917 A    6/2011
(Continued)

OTHER PUBLICATIONS

U.S. Appl. No. 14/480,570, First Named Inventor: Hiroshi Matsuzaki, Title: "Image Processing Device, Information Storage Device, and Image Processing Method", filed Sep. 8, 2014.
(Continued)

*Primary Examiner* — Siamak Harandi
(74) *Attorney, Agent, or Firm* — Holtz, Holtz & Volek PC

(57) ABSTRACT

An image processing device includes an image sequence acquisition section that acquires an image sequence that includes a plurality of images, and a processing section that performs an image summarization process that deletes some of the plurality of images included in the acquired image sequence to acquire a summary image sequence, the processing section selecting a reference image and a determination target image from the plurality of images, calculating a coverage ratio of the determination target image by the reference image based on deformation information about the reference image and the determination target image, and determining whether or not the determination target image can be deleted based on the coverage ratio.

45 Claims, 36 Drawing Sheets

(51) Int. Cl.
*A61B 1/00* (2006.01)
*G06F 19/00* (2011.01)
*G06K 9/68* (2006.01)

(52) U.S. Cl.
CPC .......... *G06K 9/00751* (2013.01); *G06K 9/68* (2013.01); *G06T 7/0024* (2013.01); *F04C 2270/0421* (2013.01)

(56) References Cited

U.S. PATENT DOCUMENTS

| | | |
|---|---|---|
| 7,120,873 B2 | 10/2006 | Li |
| 8,204,317 B2 | 6/2012 | Barbieri et al. |
| 8,279,343 B2 | 10/2012 | Uemukai et al. |
| 8,606,083 B2 | 12/2013 | Girgensohn et al. |
| 8,655,036 B2 | 2/2014 | Valadez et al. |
| 8,869,198 B2 | 10/2014 | Riveiro et al. |
| 2004/0088723 A1 | 5/2004 | Ma et al. |
| 2007/0124282 A1 | 5/2007 | Wittkotter |
| 2007/0171279 A1 | 7/2007 | Hasegawa et al. |
| 2007/0195165 A1 | 8/2007 | Hirakawa |
| 2008/0212881 A1 | 9/2008 | Hirakawa |
| 2009/0041356 A1 | 2/2009 | Barbieri et al. |
| 2009/0051695 A1 | 2/2009 | Matsuda |
| 2009/0162025 A1 | 6/2009 | Girgensohn et al. |
| 2009/0245692 A1 | 10/2009 | Okutomi et al. |
| 2010/0067808 A1* | 3/2010 | Matsuzaki ............ A61B 1/041 382/218 |
| 2010/0194992 A1 | 8/2010 | Kouno |
| 2012/0207369 A1 | 8/2012 | Valadez et al. |
| 2012/0218394 A1 | 8/2012 | Yoshino et al. |
| 2012/0281969 A1 | 11/2012 | Jiang et al. |
| 2014/0376792 A1 | 12/2014 | Matsuzaki et al. |
| 2015/0030254 A1 | 1/2015 | Yaguchi |

FOREIGN PATENT DOCUMENTS

| | | |
|---|---|---|
| JP | 2006320650 A | 11/2006 |
| JP | 2007195586 A | 8/2007 |
| JP | 2007257287 A | 10/2007 |
| JP | 2008146460 A | 6/2008 |
| JP | 2009005020 A | 1/2009 |
| JP | 2009050321 A | 3/2009 |
| JP | 2010069208 A | 4/2010 |
| JP | 2010158308 A | 7/2010 |
| JP | 2010183290 A | 8/2010 |
| JP | 2011024763 A | 2/2011 |
| JP | 2011104011 A | 6/2011 |
| JP | 2011175599 A | 9/2011 |
| JP | 2011200283 A | 10/2011 |

OTHER PUBLICATIONS

Extended European Search Report dated Dec. 1, 2015, issued in counterpart European Application No. 13778652.1.
Bezerra, et al., "Low Cost Soccer Video Summaries Based on Visual Rhythm", Proceedings of the ACM International Multimedia Conference and Exhibition—MIR '06; Oct. 26-27, 2006; pp. 71-77; 3, 3.2 and 5.2.
Yun, et al., "Face Detection for video summary using illumination-compensation and morphological processing", Pattern Recognition Letters, Elsevier, Amersterdam, NL; vol. 30, No. 9, Jul. 1, 2009; pp. 856-860; 2, 3.2, 6, Figure 1.
Yun, et al., "Robust Face Detection for Video Summary Using Illumination-Compensation and Morphological Processing", Third International Conference on Natural Computation (ICNC 2007), Aug. 24, 2007; pp. 710-714; 2, 3.2 and 6.
International Search Report (ISR) dated Apr. 2, 2013 issued in International Application No. PCT/JP2013/056271.
U.S. Appl. No. 14/514,062, filed Oct. 14, 2014, First Named Inventor: Yoichi Yaguchi, Title: "Image Processing Device, Information Storage Device, and Image Processing Method".
Chinese Office Action (and English translation thereof) dated Nov. 26, 2015, issued in Chinese Application No. 201380012887.X.
Partial Supplementary European Search Report dated Mar. 1, 2016, issued in European Application No. 13758100.5.
Yanwei, et al., "Multi-View Video Summarization", IEEE Transactions on Multimedia, vol. 12, No. 7, Nov. 2010, pp. 717-729.
Li, et al., "Online redundant image elimination and its application to wireless capsule endoscopy", Signal, Image and Video Processing 8.8 (2012): pp. 1497-1506.
Szczypaski, et al., "A model of deformable rings for interpretation of wireless capsule endoscopic videos", Medical Image Analysis 112 (2009): pp. 312-324.

* cited by examiner

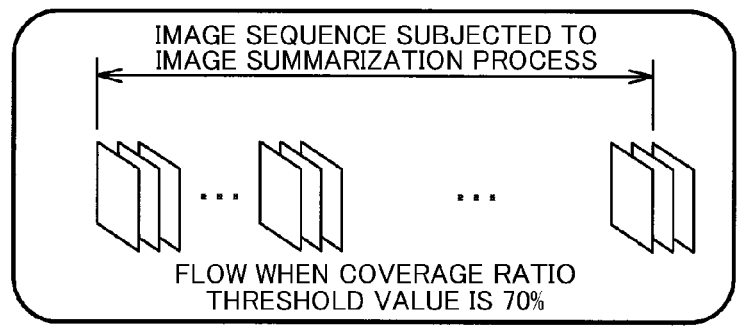
FIG. 13A
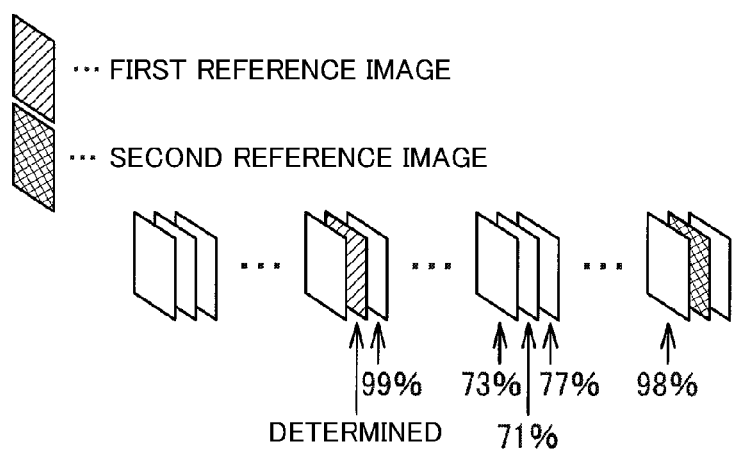
FIG. 13B
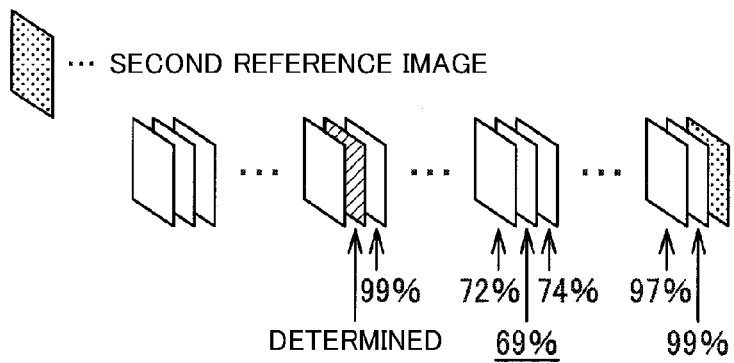

DEFORMATION INFORMATION

MASK PIXEL

ADJACENT IMAGES $$\text{ACCURACY INFORMATION} = \frac{\text{NUMBER OF MASK PIXELS}}{\text{TOTAL NUMBER OF PIXELS}}$$

FIRST IMAGE
SECOND IMAGE

SCENE CHANGE

IMAGE PROCESSING DEVICE, INFORMATION STORAGE DEVICE, AND PROCESSING METHOD TO ACQUIRE A SUMMARY IMAGE SEQUENCE

CROSS REFERENCE TO RELATED APPLICATION

This application is a continuation of International Patent Application No. PCT/JP2013/056271, having an international filing date of Mar. 7, 2013, which designated the United States, the entirety of which is incorporated herein by reference. Japanese Patent Application No. 2012-050860 filed on Mar. 7, 2012 and Japanese Patent Application No. 2012-094691, filed on Apr. 18, 2012 and Japanese Patent Application No. 2012-117318 filed on May 23, 2012 are also incorporated herein by reference in its entirety.

BACKGROUND

The present invention relates to an image processing device, an information storage device, an image processing method, and the like.

When still images are continuously captured in time series at given time intervals, or when a spatial object is covered by a number of images, or when a movie is captured, and each image that forms the movie is used as a still image, for example, a very large number of temporally or spatially continuous images (hereinafter may be referred to as "image sequence") are acquired. In such a case, it is likely that the images that are closely situated in the image sequence (i.e., images that are close to each other temporally or spatially) are similar images, and it is not likely that it is necessary to check all of a large number of images in order to determine the captured information. Since the number of images may typically be tens of thousands or more, it takes time for the user to check all of the images.

Therefore, it has been desired to summarize the original image sequence using an image sequence that includes a smaller number of images by deleting images from the original image sequence. This process is hereinafter referred to as "image summarization process". For example, JP-A-2009-5020 discloses an image summarization method that extracts a scene change boundary image included in the image sequence, or an image that represents the image sequence, and allows images from which the information represented by the image sequence can be easily determined to remain.

For example, when applying the image summarization technique in the medical field, it is necessary to prevent a situation in which an area that cannot be observed occurs due to deletion of an image in order to prevent a situation in which a disease is missed.

SUMMARY

According to one aspect of the invention, there is provided an image processing device comprising:

an image sequence acquisition section that acquires an image sequence that includes a plurality of images; and a processing section that performs an image summarization process that deletes some of the plurality of images included in the image sequence acquired by the image sequence acquisition section to acquire a summary image sequence, the processing section selecting a reference image and a determination target image from the plurality of images, calculating a coverage ratio of the determination target image by the reference image based on deformation information about the reference image and the determination target image, and determining whether or not the determination target image can be deleted based on the coverage ratio.

According to another aspect of the invention, there is provided an image processing device comprising:

an image sequence acquisition section that acquires an image sequence that includes a plurality of images; and a processing section that performs an image summarization process that deletes some of the plurality of images included in the image sequence acquired by the image sequence acquisition section to acquire a summary image sequence, the processing section selecting a reference image and a determination target image from the plurality of images, setting an observation area within the determination target image, calculating a corresponding area that is an area of the reference image that corresponds to the observation area based on deformation information about the reference image and the determination target image, and determining whether or not the determination target image can be deleted based on at least one of a first feature quantity calculated from the corresponding area and a second feature quantity calculated from the observation area.

According to another aspect of the invention, there is provided a computer-readable storage device with an executable program stored thereon, wherein the program instructs a computer to function as:

an image sequence acquisition section that acquires an image sequence that includes a plurality of images; and a processing section that performs an image summarization process that deletes some of the plurality of images included in the image sequence acquired by the image sequence acquisition section to acquire a summary image sequence, the processing section selecting a reference image and a determination target image from the plurality of images, calculating a coverage ratio of the determination target image by the reference image based on deformation information about the reference image and the determination target image, and determining whether or not the determination target image can be deleted based on the coverage ratio.

According to another aspect of the invention, there is provided a computer-readable storage device with an executable program stored thereon, wherein the program instructs a computer to function as:

an image sequence acquisition section that acquires an image sequence that includes a plurality of images; and a processing section that performs an image summarization process that deletes some of the plurality of images included in the image sequence acquired by the image sequence acquisition section to acquire a summary image sequence, the processing section selecting a reference image and a determination target image from the plurality of images, setting an observation area within the determination target image, calculating a corresponding area that is an area of the reference image that corresponds to the observation area based on deformation information about the reference image and the determination target image, and determining whether or not the determination target image can be deleted based on at least one of a first feature quantity calculated from the corresponding area and a second feature quantity calculated from the observation area.

According to another aspect of the invention, there is provided an image processing method comprising:

acquiring an image sequence that includes a plurality of images;

selecting a reference image and a determination target image from the plurality of images included in the image sequence;

calculating a coverage ratio of the determination target image by the reference image based on deformation information about the reference image and the determination target image;

determining whether or not the determination target image can be deleted based on the coverage ratio; and performing an image summarization process that deletes some of the plurality of images included in the image sequence based on a result of the determination as to whether or not the determination target image can be deleted to acquire a summary image sequence.

According to another aspect of the invention, there is provided an image processing method comprising:

acquiring an image sequence that includes a plurality of images;

selecting a reference image and a determination target image from the plurality of images included in the image sequence;

setting an observation area within the determination target image, and calculating a corresponding area that is an area of the reference image that corresponds to the observation area based on deformation information about the reference image and the determination target image;

determining whether or not the determination target image can be deleted based on at least one of a first feature quantity calculated from the corresponding area and a second feature quantity calculated from the observation area; and performing an image summarization process that deletes some of the plurality of images included in the image sequence based on a result of the determination as to whether or not the determination target image can be deleted to acquire a summary image sequence.

BRIEF DESCRIPTION OF THE DRAWINGS

FIGS. 13A and 13B are views illustrating an image summarization process according to the second embodiment.

DESCRIPTION OF EXEMPLARY EMBODIMENTS

Figure 1:
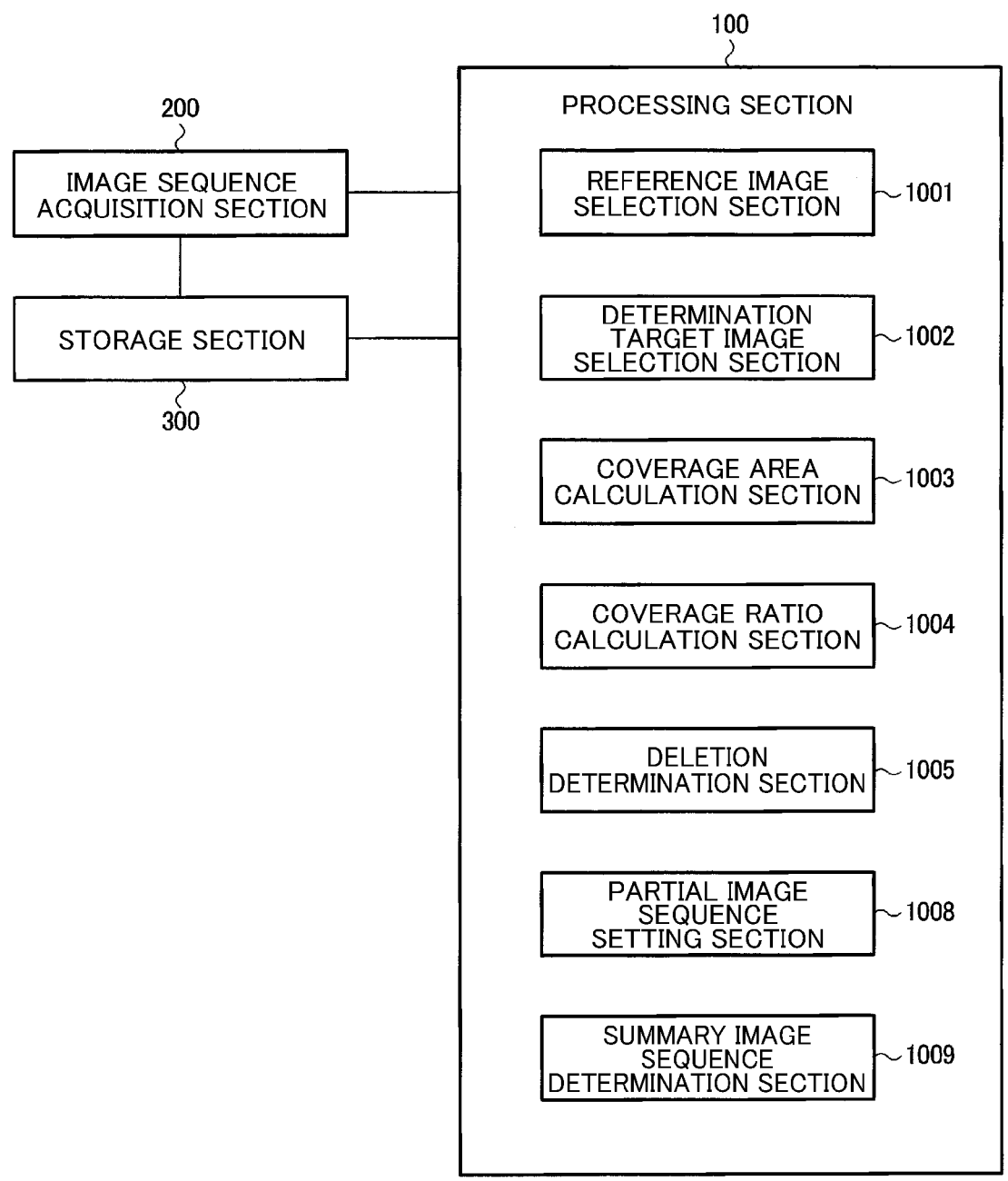
FIG. 1 illustrates a system configuration example of an image processing device according to a first embodiment.

According to one embodiment of the invention, there is provided an image processing device comprising:

an image sequence acquisition section that acquires an image sequence that includes a plurality of images; and a processing section that performs an image summarization process that deletes some of the plurality of images included in the image sequence acquired by the image sequence acquisition section to acquire a summary image sequence, the processing section selecting a reference image and a determination target image from the plurality of images, calculating a coverage ratio of the determination target image by the reference image based on deformation information about the reference image and the determination target image, and determining whether or not the determination target image can be deleted based on the coverage ratio.

According to one embodiment of the invention, the reference image and the determination target image are selected from the acquired image sequence, and the coverage ratio of the determination target image by the reference image is calculated based on the deformation information about the reference image and the determination target image to determine whether or not the determination target image can be deleted. Therefore, since whether or not the determination target image can be deleted can be determined based on the degree by which the determination target image is covered by the reference image (i.e., the image that is allowed to remain in the summary image sequence in a narrow sense), it is possible to prevent a situation in which an area that cannot be observed occurs due to deletion of an image, for example.

According to another embodiment of the invention, there is provided an image processing device comprising:

an image sequence acquisition section that acquires an image sequence that includes a plurality of images; and a processing section that performs an image summarization process that deletes some of the plurality of images included in the image sequence acquired by the image sequence acquisition section to acquire a summary image sequence, the processing section selecting a reference image and a determination target image from the plurality of images, setting an observation area within the determination target image, calculating a corresponding area that is an area of the reference image that corresponds to the observation area based on deformation information about the reference image and the determination target image, and determining whether or not the determination target image can be deleted based on at least one of a first feature quantity calculated from the corresponding area and a second feature quantity calculated from the observation area.

According to this embodiment of the invention, the observation area is set within the determination target image, and the corresponding area that corresponds to the observation area is set within the reference image based on the deformation information. Whether or not the determination target image can be deleted is determined based on at least one of the feature quantity of the observation area and the feature quantity of the corresponding area. Therefore, it is possible to prevent a situation in which an area that cannot be observed occurs due to deletion of an image by allowing the determination target image including the observation area to remain in the summary image sequence when the corresponding area is not suitable for observation, for example.

Another embodiment of the invention relates to a computer-readable storage device with an executable program stored thereon, wherein the program instructs a computer to function as each section described above.

According to another embodiment of the invention, there is provided an image processing method comprising:

acquiring an image sequence that includes a plurality of images;

selecting a reference image and a determination target image from the plurality of images included in the image sequence;

calculating a coverage ratio of the determination target image by the reference image based on deformation information about the reference image and the determination target image;

determining whether or not the determination target image can be deleted based on the coverage ratio; and performing an image summarization process that deletes some of the plurality of images included in the image sequence based on a result of the determination as to whether or not the determination target image can be deleted to acquire a summary image sequence.

According to another embodiment of the invention, there is provided an image processing method comprising:

acquiring an image sequence that includes a plurality of images;

selecting a reference image and a determination target image from the plurality of images included in the image sequence;

setting an observation area within the determination target image, and calculating a corresponding area that is an area of the reference image that corresponds to the observation area based on deformation information about the reference image and the determination target image;

determining whether or not the determination target image can be deleted based on at least one of a first feature quantity calculated from the corresponding area and a second feature quantity calculated from the observation area; and performing an image summarization process that deletes some of the plurality of images included in the image sequence based on a result of the determination as to whether or not the determination target image can be deleted to acquire a summary image sequence.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

A method used in connection with several exemplary embodiments of the invention is described below. It is desirable to perform the image summarization process when an image sequence that includes a large number of temporally or spatially continuous images has been acquired, and the user performs a process (e.g., medical practice (e.g., diagnosis) when the image sequence is an endoscopic image sequence) using the image sequence. This is because the number of images included in the image sequence is very large, and it takes time for the user to check all of the images included in the image sequence to make a determination. Moreover, it is likely that similar images are included in the image sequence, and the amount of information that can be acquired is limited even if such similar images are thoroughly checked.

Specific examples of such an image sequence include an image sequence captured using a capsule endoscope. The capsule endoscope is a capsule-shaped endoscope that includes a small camera, and captures an image at given time intervals (e.g., twice a second). The capsule endoscope remains inside a body for several hours (tens or more hours in some cases) until it is discharged from the body, and several tens of thousands of captured images are acquired during a single examination. When the capsule endoscope moves inside a living body, the capsule endoscope may stop or move backward due to the motion of the living body, for example. Therefore, a large number of captured images may include a number of images that capture a similar object, and are not useful for finding a lesion or the like.

A known image summarization process may extract a scene change boundary image or an image that represents the image sequence. However, such a known image summarization process does not take account of the relationship between the object captured within the deletion target image and the object captured within the image that is allowed to remain when deleting an image. Therefore, the object that is captured within an image included in the image sequence that is not subjected to the image summarization process may not be captured within each image included in the image sequence obtained by the image summarization process. Since the degree of occurrence of an object that is not included in each image of the image sequence obtained by the image summarization process depends on the processing target image sequence, it is difficult to control the degree of occurrence of such an object using a known method.

This is particularly undesirable when applying the image summarization process in the medical field. This is because it is necessary to prevent a situation in which the attention area (e.g., lesion) is missed as much as possible. In order to prevent a situation in which the attention area is missed, it is desirable to capture a wide range inside a living body, and prevent a situation in which an object range that cannot be observed occurs due to deletion of a given image during the image summarization process.

In order to deal with this problem, several aspects of the invention propose a method that utilizes deformation information about images (deformation information about deformation between images). For example, a reference image (i.e., an image that is allowed to remain (an image (candidate image) that may be allowed to remain depending on the embodiment)) and a determination target image (i.e., a deletion determination target image) may be selected, and the image summarization process may be performed based on the coverage ratio of the determination target image by the reference image. Specifically, the reference image is deformed to calculate a coverage area within the determination target image (see FIG. 3). The object captured within the reference image corresponds to the object captured within the coverage area within the determination target image. Specifically, an area of the determination target image other than the coverage area cannot be covered by the reference image when the determination target image is deleted.

Therefore, the degree of occurrence of an object range that cannot be observed is controlled by calculating the ratio of the coverage area with respect to the determination target image as the coverage ratio, and determining whether or not to delete the determination target image based on the calculated coverage ratio, for example. For example, the determination target image is deleted when the coverage ratio is equal to or larger than a threshold value, and is not deleted when the coverage ratio is less than the threshold value. In this case, the degree of occurrence of an area that cannot be covered can be controlled corresponding to the threshold value. Since the degree of occurrence of an area that cannot be covered can be reduced by increasing the threshold value, it is possible to effectively prevent a situation in which a lesion is missed, for example. It is possible to reduce the number of images included in the image sequence obtained by the image summarization process, and reduce the burden imposed on the user (although an area that cannot be covered may occur) by decreasing the threshold value.

Figure 19:
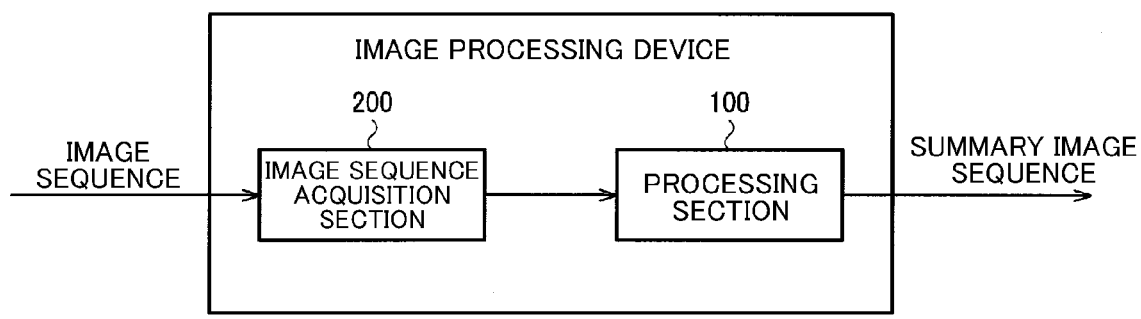
FIG. 19 illustrates a system configuration example of an image summarization process according to one embodiment of the invention.

An image processing device according to one embodiment of the invention may include a processing section 100 and an image sequence acquisition section 200 (see FIG. 19). The image sequence acquisition section 200 acquires an image sequence that includes a plurality of images. The processing section 100 performs an image summarization process that deletes some of the plurality of images included in the image sequence acquired by the image sequence acquisition section 200 to acquire a summary image sequence. Specifically, the processing section 100 selects the reference image and the determination target image from the plurality of images, and calculates the coverage ratio of the determination target image by the reference image based on the deformation information about the reference image and the determination target image. The processing section 100 determines whether or not the determination target image can be deleted based on the calculated coverage ratio.

This makes it possible to implement the image summarization process based on the coverage ratio. When it has been determined that the determination target image can be deleted, it may be determined that the determination target image is deleted (first embodiment and second embodiment), or it may not be determined that the determination target image is deleted until it is determined whether or not another determination target image can be deleted (third embodiment).

The first embodiment illustrates a method that sequentially performs the image summarization process that ensures the coverage ratio of the image that follows the reference image. Modifications of the first embodiment illustrate a method that calculates the coverage ratio using a plurality of points instead of the coverage area, a method that calculates the coverage ratio using a plurality of reference images, a method that utilizes weighting corresponding to the position within the image when calculating the coverage ratio, and a method that calculates the desired deformation information based on the deformation information about adjacent images. Note that the modifications described in connection with the first embodiment may also be applied to the second embodiment and the third embodiment.

The second embodiment illustrates a method that ensures the coverage ratio by the images that precede or follow the determination target image based on the reference images that precede or follow the determination target image. The third embodiment illustrates a method that sets the reference image at a position other than the endpoint of the image sequence, and determines whether or not to delete partial image sequences that precede or follow the reference image.

Figure 26:
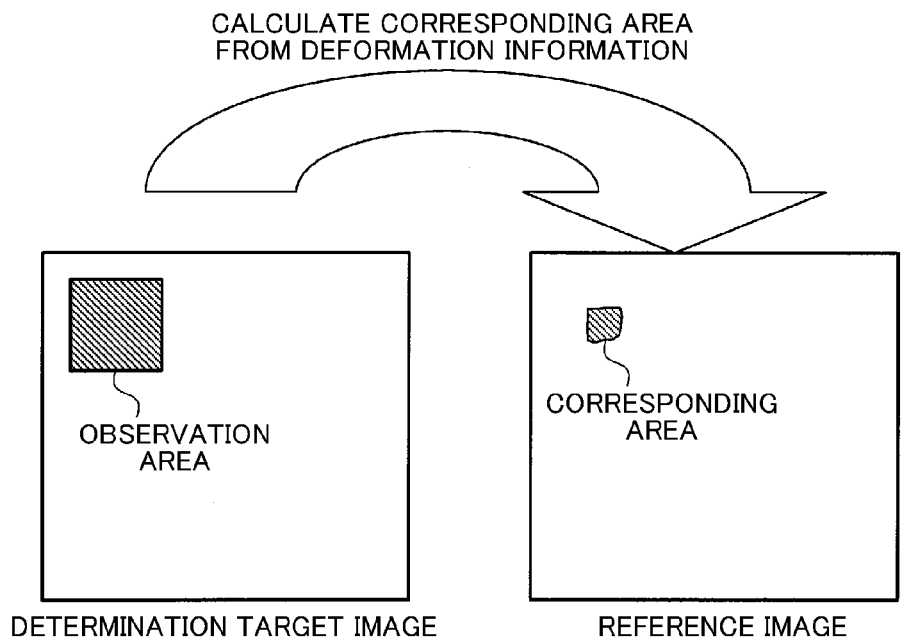
FIG. 26 illustrates an example in which size information is used as a feature quantity.

When whether or not the determination target image can be deleted is merely determined based the coverage ratio, even if the object area captured within the deletion target image is captured within the image that is allowed to remain, it may be difficult to take account of ease of observation of the object area within the image that is allowed to remain. In FIG. 26, the object that is captured within a given area of the determination target image is captured within a very narrow area of the reference image, for example. In the example illustrated in FIG. 26, it may be determined based on the coverage ratio that the object is captured within the reference image, and is not missed even if the determination target image is deleted (i.e., it may be determined that the determination target image can be deleted). However, since the size of the object within the reference image is very small (see FIG. 26), the reference image illustrated in FIG. 26 may not be suitable for observation depending on the number of pixels (resolution) of the reference image. If the size of the object is small, the object may be missed. Even if the object is not missed, it is difficult to sufficiently observe the object when it is necessary to closely observe the object in order to determine whether or not the object is a lesion, or determine the degree of progression of the lesion, for example.

In order to deal with this problem, several aspects of the invention propose a method that selects the reference image and the determination target image, and determines whether or not the determination target image can be deleted based on the feature quantity of an observation area within the determination target image, and the feature quantity of a corresponding area that is an area within the reference image that corresponds to the observation area. In this case, the corresponding area is calculated by deforming the observation area based on the deformation information about the reference image and the determination target image. Specifically, the object area captured within the observation area corresponds to (coincides with in a narrow sense) the object area captured within the corresponding area.

For example, a situation in which the size of the corresponding area is smaller than that of the observation area (see FIG. 26) can be detected by utilizing size information (e.g., area) about the area as the feature quantity. This makes it possible to deal with the above problem. Specifically, since the object is captured within a narrow range (i.e., a range corresponding to the corresponding area) within the reference image, and is not suitable for observation, it is determined that the determination target image cannot be deleted (i.e., the determination target image is allowed to remain in the summary image sequence), and the object is observed in a state in which the object is captured over a wide range (i.e., a range corresponding to the observation area) within the determination target image.

In this case, an image processing device according to one embodiment of the invention may include the processing section 100 and the image sequence acquisition section 200 (see FIG. 19). The image sequence acquisition section 200 acquires an image sequence that includes a plurality of images. The processing section 100 performs an image summarization process that deletes some of the plurality of images included in the image sequence acquired by the image sequence acquisition section 200 to acquire a summary image sequence. Specifically, the processing section 100 selects the reference image and the determination target image used for the image summarization process from the plurality of images, sets the observation area within the determination target image, calculates the corresponding area (i.e., an area of the reference image that corresponds to the observation area) based on the deformation information about the reference image and the determination target image, and determines whether or not the determination target image can be deleted based on at least one of a first feature quantity calculated from the corresponding area and a second feature quantity calculated from the observation area.

A fourth embodiment illustrates a basic method that implements the image summarization process that determines whether or not the determination target image can be deleted based on the feature quantity of the observation area and the feature quantity of the corresponding area. When the process that determines whether or not the determination target image can be deleted based on the feature quantity of the observation area and the feature quantity of the corresponding area is referred to as "first deletion determination process", the image summarization process may be implemented by combining the first deletion determination process with a second deletion determination process (e.g., a process that utilizes the coverage ratio) that differs from the first deletion determination process. A specific method will be described in connection with a fifth embodiment.

A modification may be made that takes account of an improvement in the speed and the accuracy of the process that utilizes the deformation information. For example, it may be inefficient to select the reference image and the determination target image from the entire processing target image sequence. Specifically, when the imaging target differs to a large extent between the first part and the second part of the processing target image sequence (e.g., when the first part and the second part of an image sequence captured by a capsule endoscope respectively capture the stomach and the small intestine), it is not considered that the images in the second part are covered by the images in the first part. Therefore, it may be unnecessary to perform a comparison process on the first part and the second part. In this case, an improvement in efficiency can be achieved by separately performing the image summarization process on the first part and the image summarization process on the second part.

Several aspects of the invention thus propose a method that detects a scene change from the image sequence, and divides the image sequence into a plurality of partial image sequences based on the detected scene change. The image summarization process that utilizes the deformation information may be independently performed on each partial image sequence. This makes it possible to efficiently perform the image summarization process. Moreover, since the image summarization process can be performed on a plurality of partial image sequences in parallel, the processing speed can be increased. This modification will be described in connection with a sixth embodiment.

2. First Embodiment

The first embodiment illustrates the image summarization process that ensures the coverage ratio of the image that follows the reference image. A basic method and four modifications are described below. Note that the modifications may be used either alone or in combination.

2.1 Method According to First Embodiment

FIG. 1 illustrates a system configuration example of an image processing device according to the first embodiment. The image processing device includes a processing section 100, an image sequence acquisition section 200, and a storage section 300.

The processing section 100 performs an image summarization process that deletes some of a plurality of images included in an image sequence acquired by the image sequence acquisition section 200. The function of the processing section 100 may be implemented by hardware such as a processor (e.g., CPU) or an ASIC (e.g., gate array), a program, or the like.

The image sequence acquisition section 200 acquires the image sequence that is subjected to the image summarization process. The storage section 300 stores the image sequence acquired by the image sequence acquisition section 200, and serves as a work area for the processing section 100 and the like. The function of the storage section 300 may be implemented by a memory (e.g., RAM), a hard disk drive (HDD), or the like.

The processing section 100 may include a reference image selection section 1001, a determination target image selection section 1002, a coverage area calculation section 1003, a coverage ratio calculation section 1004, a deletion determination section 1005, a partial image sequence setting section 1008, and a summary image sequence determination section 1009 (see FIG. 1). Note that the configuration of the processing section 100 is not limited to the configuration illustrated in FIG. 1. Various modifications may be made, such as omitting some of the elements illustrated in FIG. 1, or adding other elements. Note that each section is provided to describe each subroutine when the image summarization process performed by the processing section 100 is divided into a plurality of subroutines. The processing section 100 does not necessarily include each section as an element.

The reference image selection section 1001 selects a reference image from the plurality of images included in the image sequence. The determination target image selection section 1002 selects an image among the plurality of images included in the image sequence that differs from the reference image as a determination target image.

The coverage area calculation section 1003 projects the reference image onto the determination target image by utilizing deformation information (deformation parameter) about the reference image and the determination target image to calculate the coverage area. The coverage ratio calculation section 1004 calculates the coverage ratio based on the coverage area.

The deletion determination section 1005 determines whether or not the determination target image can be deleted based on the calculated coverage ratio. For example, the deletion determination section 1005 determines whether or not the determination target image can be deleted by comparing the coverage ratio with a given threshold value.

The partial image sequence setting section 1008 sets an image sequence that is included in the image sequence and includes one or more images to be the partial image sequence based on the position of the determination target image in the image sequence when the deletion determination section 1005 has determined that the determination target image cannot be deleted.

The summary image sequence determination section 1009 determines a summary image sequence that is an image sequence obtained by the image summarization process. In the first embodiment, the reference image selected by the reference image selection section 1001 is allowed to remain in the summary image sequence. The determination target image that can be deleted is deleted, and is not allowed to remain in the summary image sequence.

Figure 2:
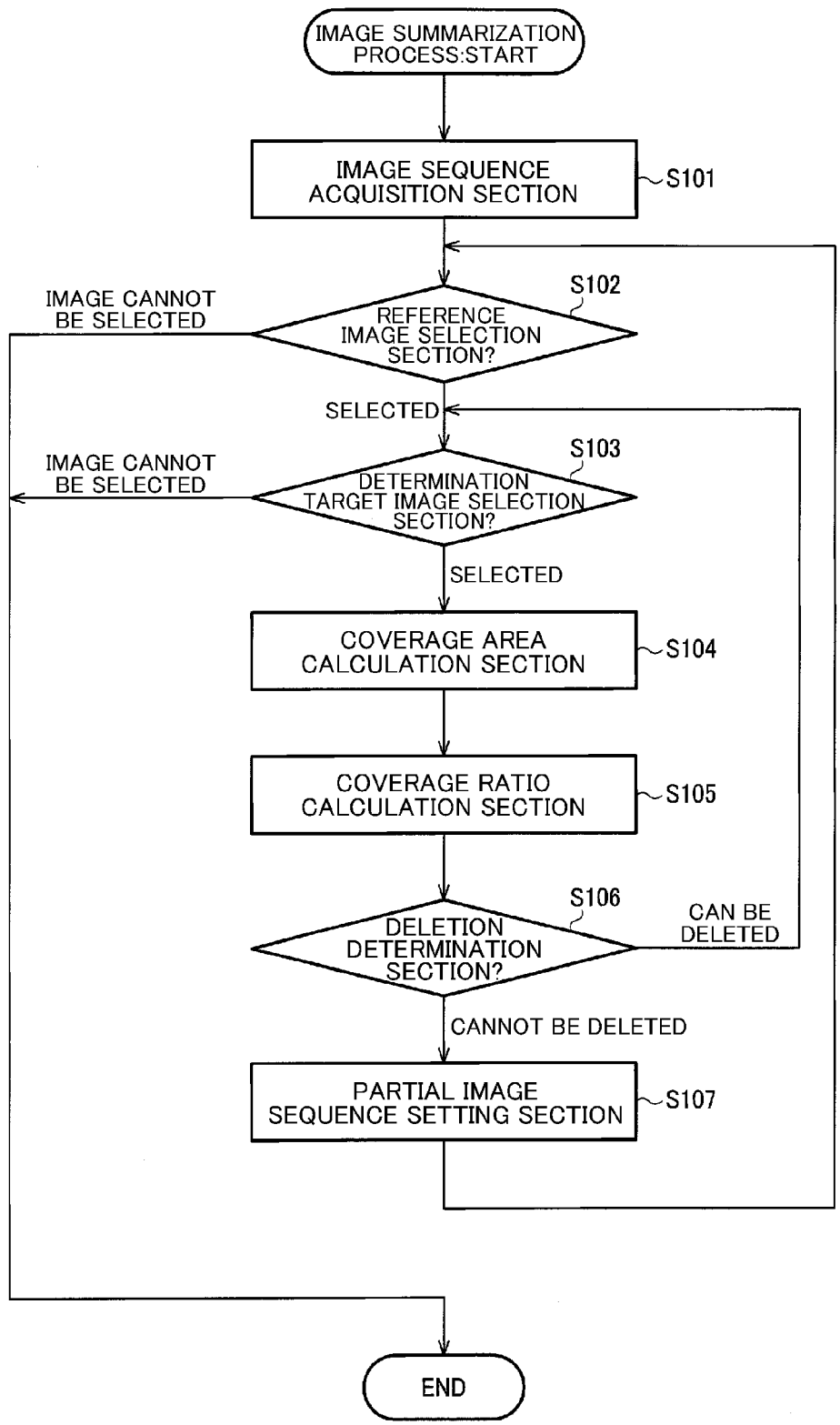
FIG. 2 is a flowchart illustrating a process according to the first embodiment.

FIG. 2 is a flowchart illustrating the image summarization process according to the first embodiment. When the image summarization process has started, the image sequence that is subjected to the image summarization process is acquired (S101). The image sequence is acquired by the image sequence acquisition section 200. The image sequence may include RGB channel images that are arranged in time series. Alternatively, the image sequence may be a spatially consecutive image sequence (e.g., an image sequence that includes spatially arranged images that have been captured using imaging devices arranged in a row). The expression "spatially" used in connection with the spatially consecutive image sequence may refer to a space that represents a two-dimensional or three-dimensional position, or may refer to a color space or the like.

When the image sequence has been acquired, the reference image selection section 1001 selects the first image of the input image sequence (i.e., the image sequence acquired in the step S101, or the partial image sequence set in a step S107) as the reference image (S102). The selected reference image is allowed to remain in the summary image sequence. Note that the process is terminated when the reference image cannot be selected from the input image sequence (e.g., when no image is included in the image sequence) due to an error or the like.

The determination target image selection section 1002 selects the determination target image from the images included in the input image sequence (S103). When the determination target image has not been set, the determination target image selection section 1002 selects the image that immediately follows the reference image (i.e., the second image of the input image sequence) as the determination target image. When the kth image of the input image sequence has been selected as the determination target image, the determination target image selection section 1002 selects the (k+1)th image (i.e., shifts the selection position by 1) of the input image sequence as the next determination target image. The process is terminated when the determination target image cannot be selected (e.g., when the number of images included in the input image sequence is less than 2 or k+1).

Figure 3:
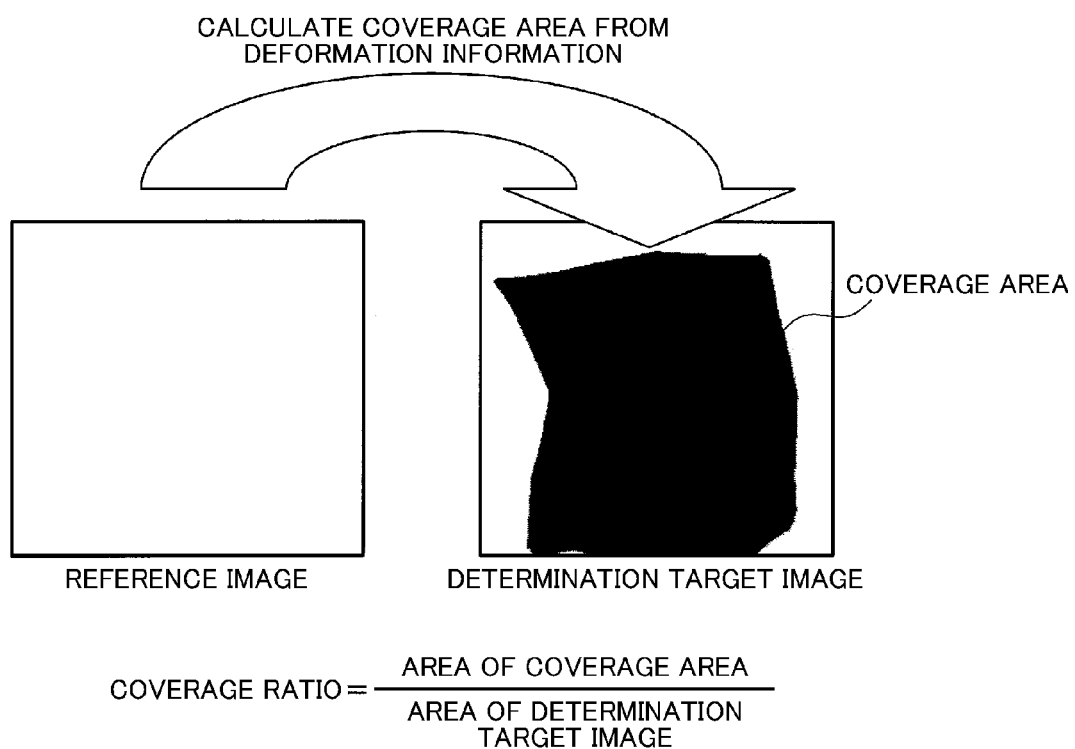
FIG. 3 is a view illustrating a coverage ratio calculation process that utilizes a coverage area.

When the reference image and the determination target image have been selected, the coverage area calculation section 1003 projects the reference image onto the determination target image by utilizing the deformation parameter about the reference image and the determination target image to calculate the coverage area (S104). The deformation parameter may be a non-rigid deformation parameter estimated by the method disclosed in JP-A-2011-24763, for example. FIG. 3 illustrates an example of the coverage area. The deformation parameter represents a state in which the object captured within the reference image is deformed within the determination target image. In other words, the object captured within the reference image corresponds to (identical with in a narrow sense) the object captured within the coverage area within the determination target image.

When the coverage area has been calculated, the coverage ratio calculation section 1004 calculates the coverage ratio based on the coverage area and the determination target image (S105). The coverage ratio may be calculated from the area ratio of the coverage area to the entire determination target image (see FIG. 3), for example.

The deletion determination section 1005 compares the calculated coverage ratio with a threshold value that is set in advance (S106). Note that the threshold value may be set by the system, or may be determined based on an input performed by the user. When the coverage ratio is less than the threshold value, it is determined that the determination target image cannot be deleted, and the partial image sequence setting process is performed. When the coverage ratio is equal to or larger than the threshold value, it is determined that the determination target image can be deleted, and the next determination target image is selected in the step S103.

When it has been determined that the determination target image cannot be deleted in the step S106, the partial image sequence setting section 1008 sets the partial image sequence (S107). Specifically, an image sequence that includes the determination target image that cannot be deleted, and the subsequent images is set to be the partial image sequence. When the partial image sequence has been set, the process in the step S102 is performed using the partial image sequence as the input image sequence.

FIGS. 4A to 4D illustrate the image summarization process described above. When an image sequence that includes N images (see FIG. 4A) has been acquired by the image sequence acquisition section 200, the first image is selected as the reference image, and the second image is selected as the determination target image. The coverage ratio of the determination target image by the reference image is calculated, and whether or not the determination target image can be deleted is determined When it has been determined that the determination target image can be deleted, the next determination target image is selected. Specifically, the third image is selected as the determination target image (i.e., the position of the determination target image is shifted to the subsequent image) (see FIG. 4B). The coverage ratio of the determination target image by the reference image is calculated, and whether or not the determination target image can be deleted is determined. Another image selected as the determination target image (i.e., the determination target image is updated) until it is determined that the determination target image cannot be deleted.

When it has been determined that the second to (k−1)th images can be deleted (i.e., the second to (k−1)th images are covered by the reference image to the extent set based on the threshold value), and the kth image cannot be deleted (see FIG. 4C), the second to (k−1)th images are deleted (i.e., the second to (k−1)th images are not allowed to remain in the summary image sequence). Since the kth image is not sufficiently covered by the reference image, it is necessary to allow the kth image to remain in the summary image sequence. Therefore, the kth image and the subsequent images (kth to Nth images) are set to be the partial image sequence. Note that the term "partial image sequence" used in connection with the first to fifth embodiments refers to the unit of repetition processing, and differs from the partial image sequence used in connection with the sixth embodiment that is subjected to parallel processing.

Figure 4A:
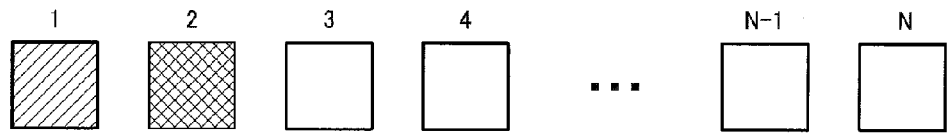
FIGS. 4A to 4D are views illustrating an image summarization process according to the first embodiment.
Figure 4B:
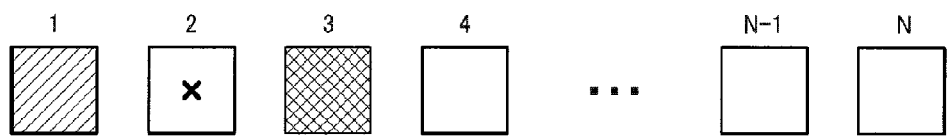
Figure 4C:
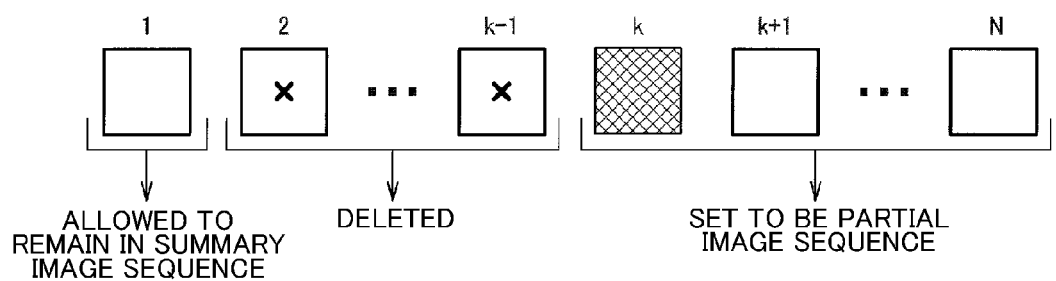
Figure 4D:
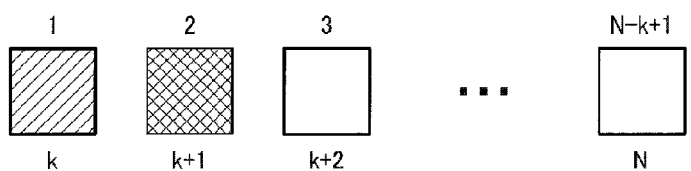

The process illustrated in FIGS. 4A to 4C is then performed on the partial image sequence. Specifically, the partial image sequence that includes N−x+1 images is used as the input image sequence (see FIG. 4D), and the process is performed using the first image (i.e., the kth image in FIG. 4C) as the reference image, and using the second image (i.e., the (k+1)th image in FIG. 4C) as the determination target image. The subsequent process is performed in the same manner as described above. When it has been determined that the determination target image can be deleted, the subsequent image is selected as the determination target image. When it has been determined that the determination target image cannot be deleted, the reference image is allowed to remain in the summary image sequence, the image that can be deleted is deleted, and the current determination target image and the subsequent images are set to be a new partial image sequence. The process is terminated when it has been determined that the last image of the input image sequence can be deleted, or when only one image is included in the input image sequence (i.e., when the determination target image cannot be set).

According to the first embodiment, the image processing device includes the image sequence acquisition section 200 that acquires an image sequence that includes a plurality of images, and the processing section 100 that performs the image summarization process that deletes some of the plurality of images included in the image sequence acquired by the image sequence acquisition section 200 to acquire the summary image sequence (see FIG. 1). The processing section 100 selects the reference image and the determination target image from the plurality of images. This process is performed by the reference image selection section 1001 and the determination target image selection section 1002, for example. The processing section 100 calculates the coverage ratio of the determination target image by the reference image based on the deformation information about the reference image and the determination target image, and determines whether or not the determination target image can be deleted based on the calculated coverage ratio. The coverage ratio calculation process is performed by the coverage ratio calculation section 1004, and the deletion determination process is performed by the deletion determination section 1005, for example.

The coverage ratio is information that represents the degree by which the object captured within the determination target image is captured within the reference image. For example, when an image having an aspect ratio of 1:1 is acquired, a 10×10 m (dimensions in the real space) square object is captured over the entire determination target image, and a 5×5 m square object that is included in the 10×10 m square object is captured over the entire reference image. In this case, a 100 $m^2$ (area in the real space) area is captured within the determination target image, and a 25 $m^2$ (area in the real space) area (that is included in the 100 $m^2$ area) is captured within the reference image. Therefore, the reference image covers 25% of the determination target image. In this case, the coverage ratio is 25 or 0.25, for example. Since a planar object is rarely captured almost perpendicularly, the reference image and the determination target image normally differ in shape even if an identical object is captured within the reference image and the determination target image. According to the first embodiment, the deformation information corresponding to such a deformation is acquired using the method disclosed in JP-A-2011-24763 or the like, and the coverage ratio is calculated using the deformation information. Note that the coverage ratio is information that represents the degree of coverage of the determination target image by the reference image, and is not limited to a ratio and the like.

Whether or not the determination target image can be deleted is determined by performing a comparison process using a given threshold value, for example. It is expected that the degree of occurrence of an area that cannot be observed due to deletion of an image can be reduced by increasing the threshold value (e.g., setting the threshold value to a value that corresponds to 100%). On the other hand, the number of images included in the summary image sequence can be reduced by decreasing the threshold value. Since the effect of reducing the degree of occurrence of an area that cannot be observed due to deletion of an image and the effect of reducing the number of images included in the summary image sequence have a trade-off relationship, and can be controlled by appropriately setting the threshold value, it is desirable to appropriately set the threshold value corresponding to the situation.

The above configuration makes it possible to prevent occurrence of an object area that cannot be observed due to deletion of an image during the image summarization process, and control the degree by which occurrence of such an object area is prevented. Specifically, when a value that corresponds to x % is used as the threshold value used to determine whether or not the determination target image can be deleted (deletion determination process), the method according to the first embodiment ensures that x % of the object captured within the determination target image is covered by the reference image even when the determination target image is deleted. Note that an area of the determination target image that is covered by the reference image may be less than x % even when a value that corresponds to x % is used as the threshold value since it is difficult to accurately calculate the deformation of the object within the image as the deformation information.

When first to Nth (N is an integer equal to or larger than 2) images have been input as the input image sequence, the processing section 100 may select the first image as the reference image, and select the kth (k is an integer that satisfies 2≤k≤N−1) image as the determination target image. The processing section 100 may calculate the coverage ratio based on the deformation information about the reference image and the determination target image, and determine whether or not the determination target image can be deleted based on the calculated coverage ratio. The processing section 100 may select the (k+1)th image as the determination target image when it has been determined that the kth image can be deleted.

The input image sequence refers to an image sequence that is subjected to the above process (selection of the reference image and the determination target image, determination as to whether or not the determination target image can be deleted, and update of the determination target image when the determination target image can be deleted), and may be an image sequence acquired by the image sequence acquisition section 200, or may be an image sequence that includes images among the images included in the image sequence acquired by the image sequence acquisition section 200.

This makes it possible to implement the process illustrated in FIGS. 4A and 4B and the like when the input image sequence has been input. The determination target image is selected from the images that follow the reference image (e.g., the image that is adjacent to the reference image), and the determination target image is updated with the image that follows the current determination target image when the selected determination target image can be deleted. Specifically, whether or not the determination target image can be deleted is determined sequentially from the image situated closer to the reference image to determine (search) an image that cannot be deleted. The determination target image that can be deleted (that has been determined to be deleted) is basically deleted, and is not allowed to remain in the summary image sequence. Note that the configuration is not limited thereto. A determination target image among the determination target images that can be deleted may be allowed to remain in the summary image sequence.

The processing section 100 may perform a process that allows the image selected as the reference image to remain in the summary image sequence. The processing section 100 may set the partial image sequence that includes the kth to Nth images to be the next input image sequence when it has been determined that the kth image selected as the determination target image cannot be deleted, and may perform the process on the set input image sequence.

This makes it possible to implement the process illustrated in FIG. 4C. Since the process that determines whether or not the determination target image can be deleted (deletion determination process) is performed based on the degree by which the determination target image is covered by the reference image, occurrence of an area that cannot be observed can be prevented by allowing the reference image to remain, even if the determination target image that can be deleted, is deleted. Specifically, the reference image is allowed to remain in the summary image sequence. When it has been determined that the kth image cannot be deleted (i.e., when the kth image is not sufficiently covered by the reference image), it is necessary to allow the kth image to remain in the summary image sequence. In this case, the kth image is set to be the next reference image. For example, the partial image sequence that includes the kth to Nth images is set to be the next input image sequence. According to this configuration, the first image of the input image sequence (i.e., the kth image included in the image sequence acquired by the image sequence acquisition section 200) is selected as the reference image, and the (k+1)th and subsequent images are sequentially selected as the determination target image (see FIG. 4D). Note that the partial image sequence that includes images among the images included in the image sequence illustrated in FIG. 4D may be set to be the input image sequence. The process is repeatedly (or recursively) performed.

The processing section 100 may calculate the coverage area (i.e., an area in which the determination target image is covered by the reference image (an area of the determination target image that is covered by the reference image) based on the deformation information about the reference image and the determination target image. The processing section 100 may calculate the ratio of the coverage area to the determination target image as the coverage ratio.

This makes it possible to calculate the coverage ratio based on the coverage area. The coverage area is an area illustrated in FIG. 3. The coverage area is an area obtained by deforming the reference image based on the deformation information, and projecting the deformed reference image onto the determination target image. The object area captured within the reference image corresponds to (coincides with when the deformation information includes no error (ideal situation)) the object area captured within the calculated coverage area. Therefore, the coverage ratio can be calculated from the ratio (i.e., area ratio) of the coverage area to the determination target image. Note that the coverage area is calculated by deforming the reference image based on the deformation information, and the calculated coverage area need not necessarily be projected onto the determination target image. The coverage area need not necessarily be calculated based on the entirety of the reference image. The coverage area may be calculated by deforming part of the reference image based on the deformation information.

The first embodiment may also be applied to a program that causes a computer to function as the image sequence acquisition section 200 that acquires an image sequence that includes a plurality of images, and the processing section 100 that performs the image summarization process that deletes some of the plurality of images included in the image sequence acquired by the image sequence acquisition section 200 to acquire the summary image sequence. The processing section 100 selects the reference image and the determination target image from the plurality of images. The processing section 100 calculates the coverage ratio of the determination target image by the reference image based on the deformation information about the reference image and the determination target image, and determines whether or not the determination target image can be deleted based on the calculated coverage ratio.

This makes it possible to implement the above image processing using a program. For example, an image sequence acquired by a capsule endoscope or the like may be input to a system (e.g., PC), and the image summarization process may be implemented by a program that is executed by a processing section (e.g., CPU or GPU) included in the system. The program is stored in an information storage device. The information storage device may be an arbitrary recording device that is readable by a system (e.g., PC), such as an optical disk (e.g., DVD and CD), a magnetooptical disk, a hard disk (HDD), or a memory (e.g., nonvolatile memory and RAM).

2.2 Modification (Calculation of Coverage Ratio Based on a Plurality of Points)

A modification of the first embodiment is described below. Although an example in which the reference image is deformed using the deformation parameter to calculate the coverage area has been described above, the coverage ratio calculation method is not limited thereto. For example, a plurality of points may be set to the determination target image, and moved based on the deformation parameter, and the coverage ratio may be calculated based on the positional relationship between the reference image and the plurality of points that have been moved. The details thereof are described below.

The processing section 100 is configured in the same manner as in FIG. 1, except that the coverage area calculation section 1003 is omitted. The process performed by the coverage ratio calculation section 1004 differs from that described above. The remaining configuration including the process is the same as described above, and detailed description thereof is omitted. The following description focuses on the coverage ratio calculation process.

Figure 5:
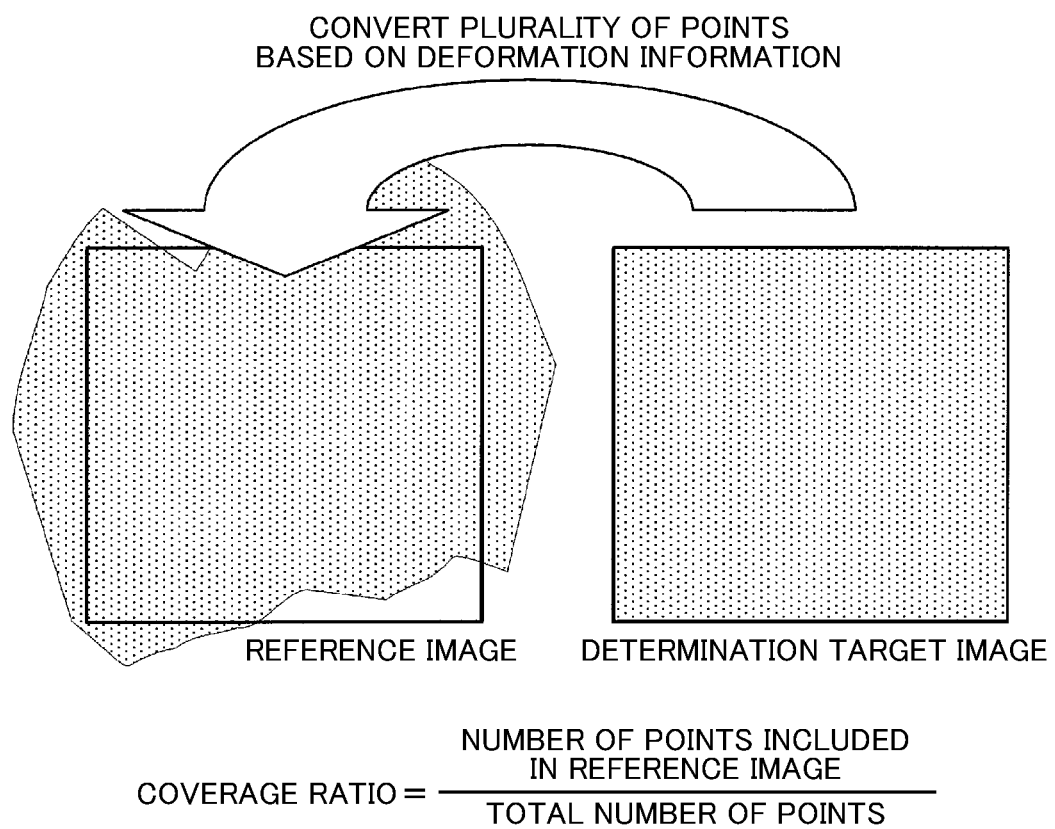
FIG. 5 is a view illustrating a coverage ratio calculation process that utilizes a plurality of points.

The coverage ratio calculation section 1004 sets a plurality of points to the determination target image at equal intervals, for example (see FIG. 5). The coverage ratio calculation section 1004 projects the plurality of points set to the determination target image onto the reference image by utilizing the deformation parameter (e.g., the non-rigid deformation parameter disclosed in JP-A-2011-24763) about the reference image and the determination target image. The ratio of the number of points included in the reference image to the total number of points projected onto the reference image may be used as the coverage ratio.

In this case, the coverage ratio can be easily calculated as compared with the method that deforms the image to calculate the coverage area, and the processing load can be reduced, for example.

Figure 6:
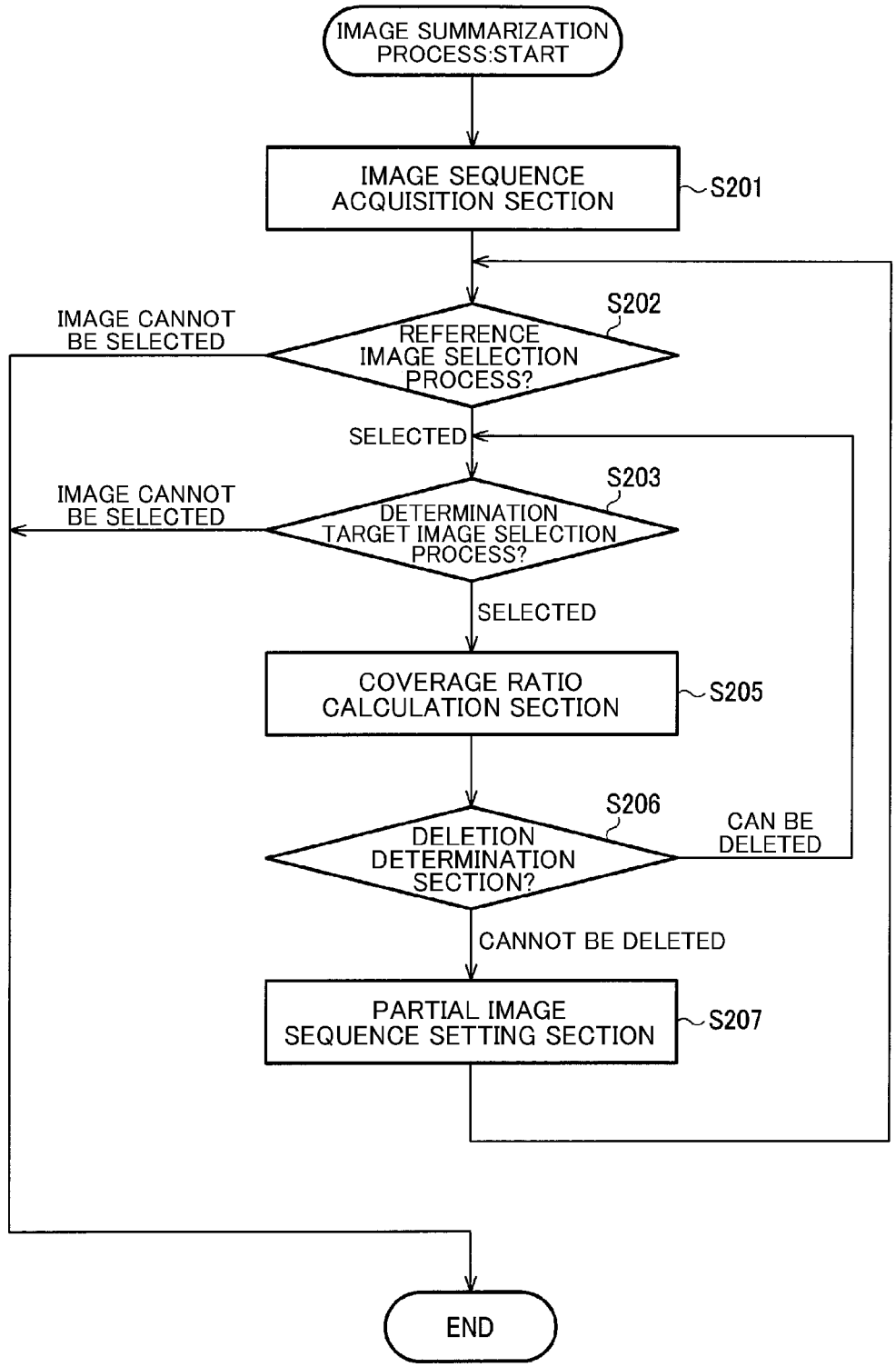
FIG. 6 is a flowchart illustrating a coverage ratio calculation process that utilizes a plurality of points.
Figure 7:
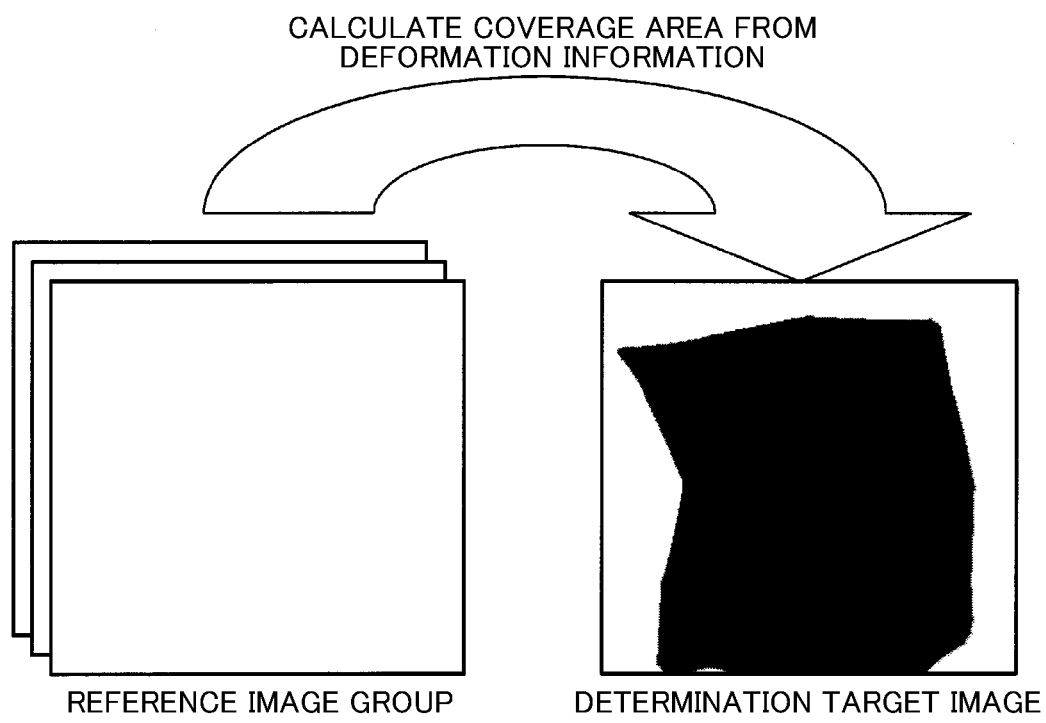
FIG. 7 is a view illustrating a modification that selects a plurality of reference images.

FIG. 6 is a flowchart illustrating the above process. Note that steps S201 to S203, S206, and S207 are the same as the steps S101 to S103, S106, and S107, respectively. The block that corresponds to the step S104 is omitted since it is unnecessary to calculate the coverage area. A step S205 corresponds to the step S105, but differs in process from the step S105. In the step S105, the coverage ratio is calculated based on the coverage area calculated in the step S104. In the step S205, the coverage ratio is calculated based on the results obtained by projecting the plurality of points.

According to this modification, the processing section 100 sets a plurality of points to the determination target image, and calculates the coverage ratio based on the number of points included in the reference image when the plurality of points are converted corresponding to the deformation information about the reference image and the determination target image.

According to this configuration, since the coverage ratio can be calculated by performing a process on the points set to the determination target image instead of performing a process on the reference image based on the deformation information, it is possible to reduce the processing load as compared with the method that calculates the coverage area. Specifically, a plurality of points are set to the determination target image, and the position within the reference image (including the position outside the reference image) that corresponds to each point is calculated. The coverage ratio is calculated by comparing the number of points set to the determination target image with the number of points included in the reference image after performing the process based on the deformation information. This makes it unnecessary to calculate the area after performing the process based on the deformation information, and makes it possible to reduce the processing load, for example. This modification takes account of the case where the determination target image cannot be sufficiently covered by the reference image. In such a case, even if a plurality of points are set to the reference image, and moved to the determination target image, all of the plurality of points are included in the determination target image. Therefore, such points cannot be used as an index that represents the degree of coverage ratio. Therefore, when using the method that sets a plurality of points, it is desirable to set the plurality of points to the determination target image.

2.3 Modification (Example in which a Plurality of Reference Images are Set)

An example in which a plurality of images are used as the reference image is described below. The processing section 100 is configured in the same manner as in FIG. 1. The coverage area calculation section 1003 calculates a candidate area for the coverage area using each reference image among a plurality of reference image (reference image group) and the determination target image, and calculates the coverage area based on a plurality of candidate areas thus calculated. In this case, the process performed by the coverage ratio calculation section 1004, the process performed by the deletion determination section 1005, and the like are the same as described above.

Alternatively, the coverage area may be calculated using each reference image among a plurality of reference image (reference image group) and the determination target image, and the coverage ratio calculation section 1004 may calculate the coverage ratio based on the determination target image and a plurality of coverage areas thus calculated.

A specific process is described below. The flowchart of the specific process is the same as that illustrated in FIG. 2. The step S101 is the same as described above. In the step S102, the first image of the input image sequence is selected as the reference image, and added to the reference image group. Since only one reference image is included in the reference image group when the process in the S102 has been performed for the first time, the processes in the steps S103 to S107 are performed in the same manner as described above.

Figure 8:
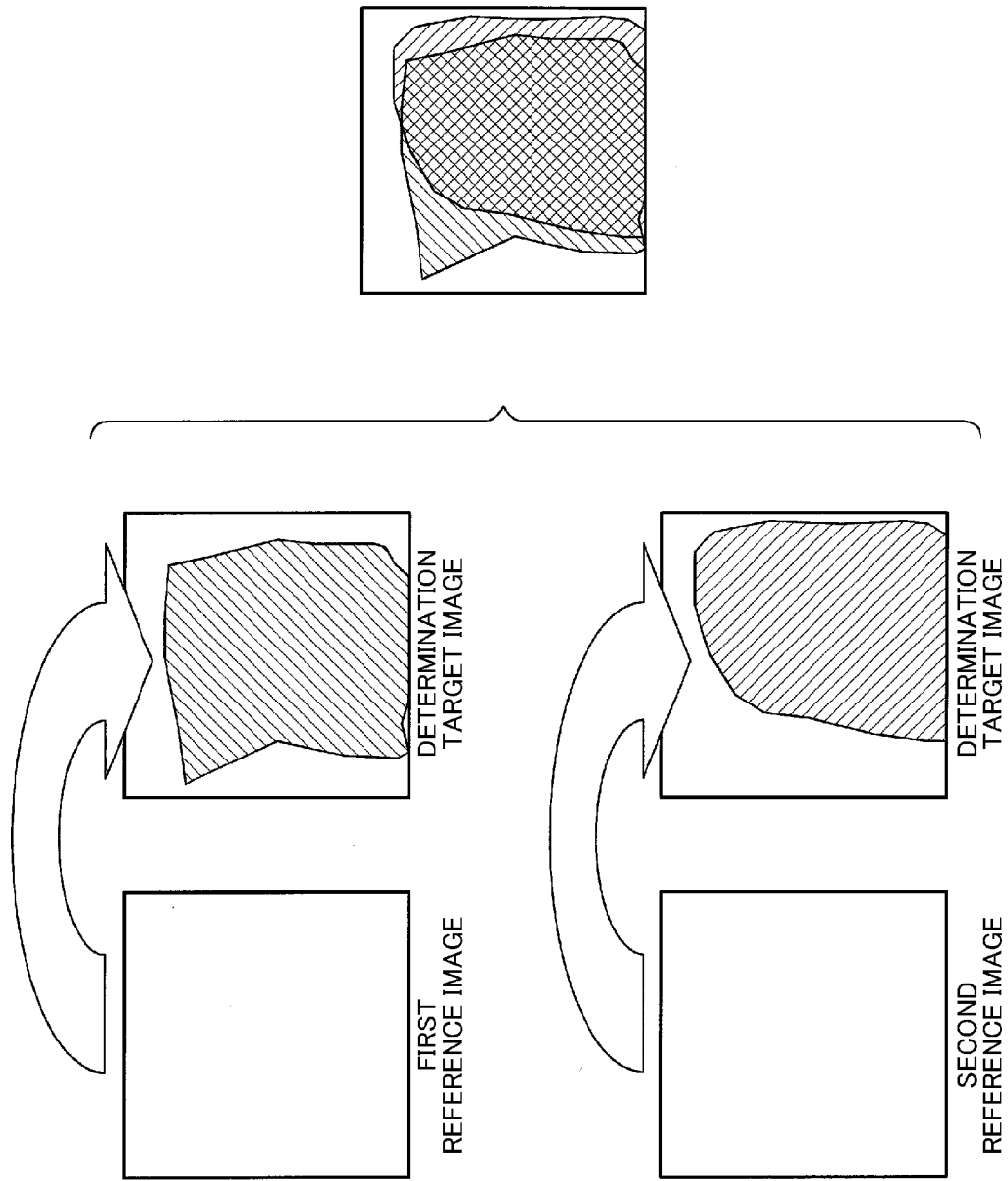
FIG. 8 is a view illustrating a process that calculates a coverage area based on a plurality of reference images.

When the partial image sequence has been set in the S107, and the step S102 is performed again, the reference image selection section 1001 selects the first image of the partial image sequence as the reference image, and adds the selected reference image to the reference image group. Specifically, when the process in the S102 has been performed m times, m reference images in total are included in the reference image group. An ith candidate area is calculated from the ith ($1 \leq i \leq m$) reference image included in the reference image group and the determination target image to calculate m candidate areas, and the coverage area is calculated from the m candidate areas. For example, an area that corresponds to the sum-set of the plurality of candidate areas may be determined to be the coverage area (see FIG. 8).

Figure 9:
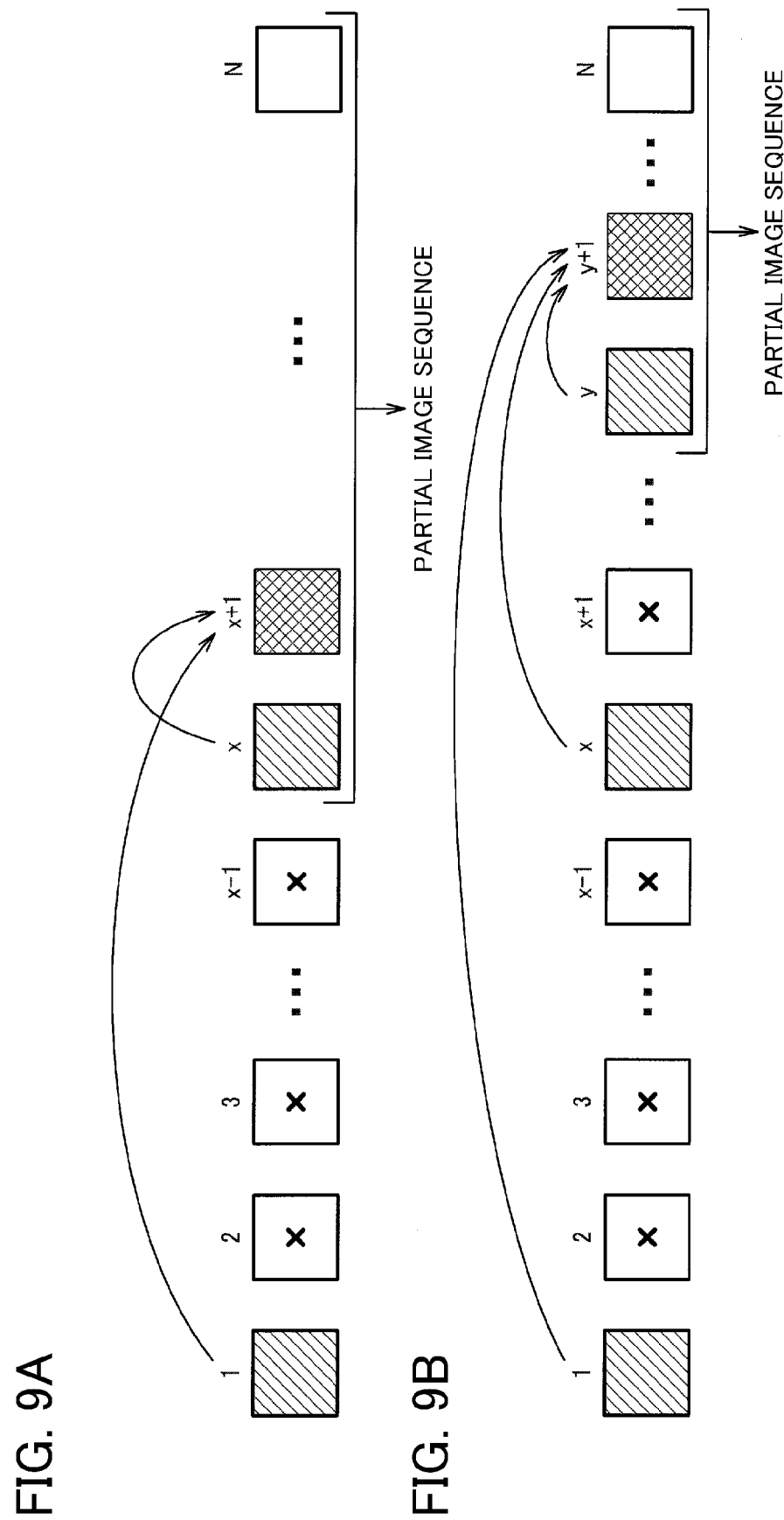
FIGS. 9A and 9B are views illustrating a modification that selects a plurality of reference images.

FIGS. 9A and 9B illustrate a specific example. When the first image has been selected as the reference image, and it has been determined that the second to (x−1)th images can be deleted, and the xth image cannot be deleted, an image sequence that includes the xth to Nth images is set to be the partial image sequence. The first image of the partial image sequence (i.e., the xth image of the original image sequence) is selected as the reference image. Therefore, the first image and the xth image are added to the reference image group as the reference image. When the determination target image (that is sequentially selected from the (x+1)th image) has been selected, the candidate area is calculated based on the first image and the determination target image, and calculated based on the xth image and the determination target image. The coverage area is calculated using the method described above with reference to FIG. 8 or the like, and whether or not the determination target image can be deleted is determined When it has been determined that the yth image cannot be deleted, an image sequence that includes the yth to Nth images is set to be the partial image sequence, and the yth image is added to the reference image group. The (y+1)th image and the subsequent images are sequentially selected as the determination target image, the candidate area is respectively calculated from the first image, the xth image, and the yth image, and the coverage area is calculated. The above process is repeated.

Although an example in which the coverage area is used to calculate the coverage ratio has been described above, the configuration is not limited thereto. For example, the method that utilizes a plurality of points may be used in combination.

According to this modification, the processing section 100 may select first to Mth (M is an integer equal to or larger than 2) reference images from a plurality of images as the reference image. The processing section 100 may calculate a uth ($1 \leq u \leq M$) coverage area based on the deformation information about the uth reference image and the determination target image, set an area that corresponds to the sum-set of the first to Mth coverage areas to be the coverage area, and calculate the coverage ratio based on the set coverage area.

This makes it possible to set a plurality of reference images as the reference image (see FIGS. 9A and 9B). When only one reference image is set, whether or not the determination target image (e.g., the (x+1)th image in FIG. 9A) can be deleted is determined using the reference image (e.g., the xth image in FIG. 9A) that immediately precedes the determination target image. However, when it is desired to prevent occurrence of an area that cannot be observed due to deletion of an image, the object captured within the deletion target image need not be captured within the image that is allowed to remain and immediately precedes the deletion target image (i.e., it suffices that the object captured within the deletion target image be captured within at least one image that is allowed to remain). Therefore, a plurality of reference images may be used instead of using only one reference image. In the example illustrated in FIG. 9A, when the xth to Nth images are set to be the partial image sequence, the xth image is selected as the next reference image. In this case, the first image that has been selected as the reference image during the preceding process may be stored, and used to determine whether or not the determination target image (i.e., the (x+1)th image and the subsequent images) can be deleted, for example. In this case, the coverage area may be an area that corresponds to the sum-set of the areas obtained by deforming each reference image based on the deformation information (see FIG. 8). In this case, it is likely that it is determined that the determination target image can be deleted, and the number of images included in the image sequence obtained by the image summarization process can be reduced. This makes it possible to reduce the burden imposed on the user, for example. Note that the number of images that can be used as the reference image increases (the yth image, the first image, and the xth image can be used as the reference image in the example illustrated in FIG. 9B) by repeating the process, and it is more likely that it is determined that the determination target image can be deleted. However, since the processing load increases as the number of reference images increases, all of the candidates for the reference image need not necessarily be used (i.e., some of the candidates for the reference image may be used).

When using a method that utilizes a plurality of points instead of using the coverage area, the processing section 100 may select first to Mth (M is an integer equal to or larger than 2) reference images from a plurality of images as the reference image. The processing section 100 may calculate the number of points included in the uth ($1 \leq u \leq M$) reference image as uth coverage information when the plurality of points are converted corresponding to the deformation information about the uth reference image and the determination target image, and calculate the coverage ratio based on the first coverage information to the Mth coverage information.

This makes it possible to set a plurality of reference images when using a plurality of points. Since the number of points included in the reference image is used to calculate the coverage ratio when using a plurality of points, it is difficult to calculate information that corresponds to the sum-set of the coverage information calculated from a plurality of reference images. Since the position of each point is calculated, information that corresponds to the sum-set of the coverage information can be calculated by performing a process based on the position information. In this case, however, the advantage that the process is simple as compared with the method that utilizes the coverage area, may be impaired. Therefore, the coverage ratio may be calculated using the maximum value among the numbers of points calculated from each reference image, for example. In this case, the effect of reducing the number of images may be insufficient as compared with the method that utilizes a plurality of reference images and the coverage area. Note that the processing load can be reduced as compared with the method that utilizes a plurality of reference images and the coverage area, and the number of images after the image summarization process can be reduced as compared with the method that utilizes one reference image.

2.4 Modification (Weighting)

Although an example in which the area ratio of the coverage area to the determination target image is used as the coverage ratio has been described above, the configuration is not limited thereto. For example, a weighting coefficient may be set corresponding to the position within the image, and a weighting process using the weighting coefficient may be performed to calculate the coverage ratio. This modification illustrates an example in which an image summarization process that ensures a coverage ratio that is weighted corresponding to the distance from the center of the image is sequentially performed. Note that detailed description of the same process as described above is omitted.

Figure 10:
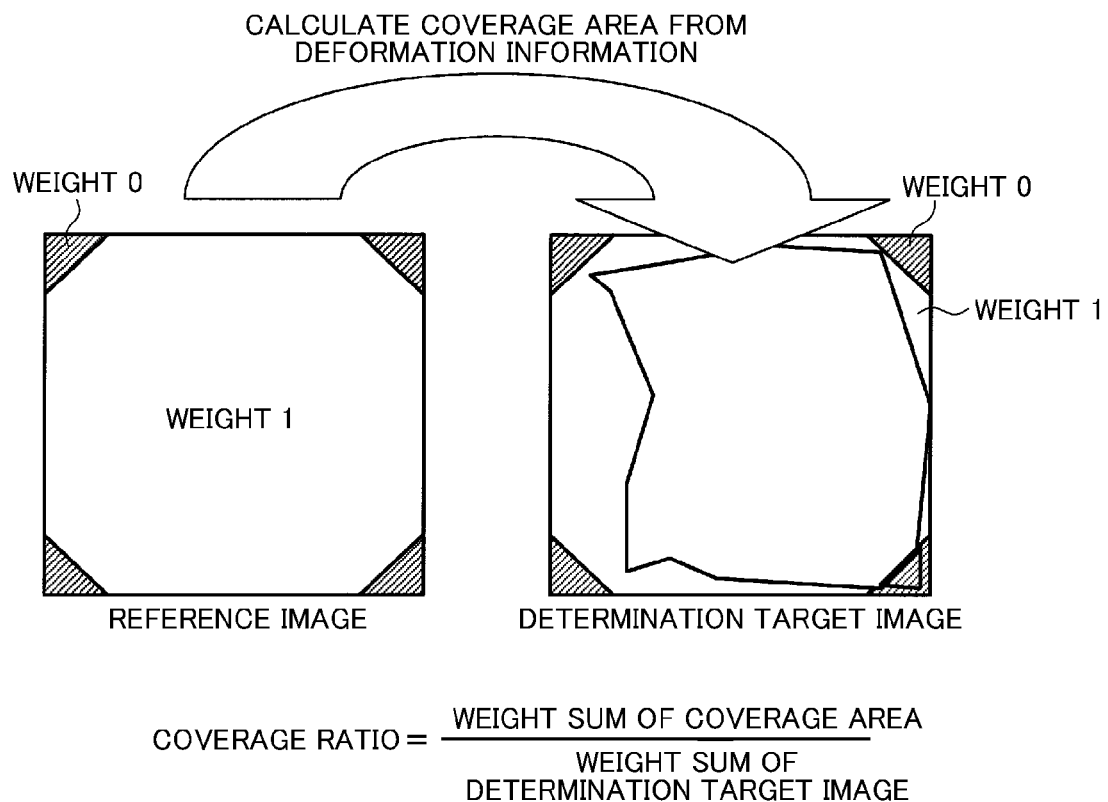
FIG. 10 is a view illustrating a coverage ratio calculation process that utilizes a weighting process.

The coverage area calculation section 1003 acquires a reference image weight map in which a weight is applied corresponding to the position within the image. As illustrated in FIG. 10, the reference image weight map is projected onto the determination target image by utilizing the deformation parameter about the reference image and the determination target image to calculate a weighted coverage area. For example, when processing a capsule endoscopic image in which blocked up shadows occur at each corner, the weight applied to a given area at each corner is set to 0, and the weight applied to the remaining area is set to 1.

The coverage ratio calculation section 1004 acquires a determination target image weight map in which a weight is applied corresponding to the position within the image. The ratio of the sum of a coverage weight map obtained by multiplying the determination target image weight map by the weighted coverage area to the sum of the determination target image weight map is calculated to be the coverage ratio. For example, when processing a capsule endoscopic image in which blocked up shadows occur at each corner, the weight applied to a given area at each corner is set to 0, and the weight applied to the remaining area is set to 1.

In the example illustrated in FIG. 10, the area at each corner in which the weight is set to 0 in the reference image weight map is not handled as the coverage area. The area within the coverage area in which the weight is set to 0 in the determination target image weight map is also not handled as the coverage area. The area of the determination target image that corresponds to the denominator of the coverage ratio calculation expression excludes the area at each corner in which the weight is set to 0 in the determination target image weight map.

Although 0 or 1 is used as the weight in the example illustrated in FIG. 10, the weight may be set to a value between 0 and 1. Although the weight is typically set to a value between 0 and 1, the weight may be set to a negative value, or may be set to a value larger than 1.

Note that the weighting process need not necessarily utilize the coverage area. For example, a plurality of points may be set, and the weighting coefficient may be set to each point. The weighting process may also be applied to the method that utilizes a plurality of reference images.

According to this modification, the processing section 100 may set the weighting coefficient corresponding to the position within the determination target image. The processing section 100 may calculate the coverage ratio based on the ratio of a first weight sum that is calculated based on the weighting coefficient and the coverage area to a second weight sum that is calculated based on the weighting coefficient and the determination target image.

This makes it possible to perform the weighting process corresponding to the position within the determination target image, and set the degree of contribution to the coverage ratio calculation process corresponding to the position within the determination target image. For example, when using an optical system that is significantly affected by distortion (e.g., fish-eye lens), the peripheral area of the image is distorted to a large extent as compared with the center area of the image (i.e., the peripheral area of the image is not suitable for observing the object). In this case, the deletion determination process that attaches weight to the center area can be implemented by increasing the weighting coefficient set to the center area, and decreasing the weighting coefficient set to the peripheral area. Specifically, even when an equal area within the image is covered, a contribution to the coverage ratio increases when the center area is covered, and decreases when the peripheral area is covered.

The weight sum is determined based on the processing target area and the weighting coefficient. For example, when the weighting coefficient is set to each pixel, the first weight sum may be calculated by calculating the sum of the weighting coefficient set to each pixel included in the coverage area, and the second weight sum may be calculated by calculating the sum of the weighting coefficient set to each pixel included in the entire determination target image. When the weighting coefficient is set to each given area (that may differ in size), the second weight sum is the sum of the product of the weighting coefficient and the area to which the weighting coefficient is set, and the first weight sum is the sum of the product of the weighting coefficient and the area to which the weighting coefficient is set and which is included in the coverage area. The weight sum may be calculated using another method depending on the weighting coefficient setting method.

The processing section 100 may set the weighting coefficient corresponding to the position within the determination target image when using a method that utilizes a plurality of points instead of the coverage area. The processing section 100 may calculate the coverage ratio based on the weighting coefficient and the number of points included in the reference image when the plurality of points are converted corresponding to the deformation information about the reference image and the determination target image.

This makes it possible to utilize the weighting coefficient when using a plurality of points. For example, when setting a plurality of points to the determination target image, the weighting coefficient corresponding to the position within the image may be set to each point. When the plurality of points are projected onto the reference image based on the deformation information, the coverage ratio is calculated by integrating the weighting coefficients set to the points included in the reference image instead of merely counting the number of points included in the reference image. In this case, the sum of the weighting coefficient set to each point is used as the denominator of the coverage ratio calculation expression illustrated in FIG. 5 instead of the total number of points.

The processing section 100 may set 0 to a first area of the determination target image as the weighting coefficient, and set 1 to a second area of the determination target image that differs from the first area.

This makes it possible to perform a process that uses part of the determination target image, and does not use the remaining area (i.e., extreme weighting example).

Although an example in which the weighting coefficient is set to the determination target image has been described above, the weighting coefficient may also be set to the reference image. In FIG. 10 (in which the coverage area is used), a weighting coefficient "0" is set to each corner of the reference image, and a weighting coefficient "1" is set to the remaining area of the reference image, for example. In this case, the second weight sum is calculated in the same manner as described above, but the first weight sum is calculated using a method that differs from the method described above. A weighting coefficient "0" is set to the area of the coverage area that corresponds to each corner of the reference image, and a weighting coefficient "1" is set to the remaining area of the coverage area. Since the coverage area is projected onto the determination target image, the weighting coefficient corresponding to the position within the determination target image is also set. Specifically, when the weighting coefficient is set to each pixel, the weighting coefficient corresponding to the reference image and the weighting coefficient corresponding to the determination target image are set to each pixel included in the coverage area. In this case, the first weight sum may be calculated by calculating the product of the weighting coefficient corresponding to the reference image and the weighting coefficient corresponding to the determination target image corresponding to each pixel included in the coverage area, and calculating the sum of the products, for example.

The weighting coefficient may also be set to the reference image when using a plurality of points (see FIG. 5). In this case, since each point among the plurality of points that is situated within the reference image can be linked to the weighting coefficient set to the reference image, the weighting coefficient corresponding to the reference image and the weighting coefficient corresponding to the determination target image are set to each point. Therefore, the product of the weighting coefficient corresponding to the reference image and the weighting coefficient corresponding to the determination target image may be calculated corresponding to each point included in the reference image, and the coverage ratio may be calculated based on the sum of the products, for example.

2.5 Modification (Method that Utilizes Deformation Parameter about Adjacent Images)

Although an example in which the coverage area is calculated directly using the deformation parameter about the reference image and the determination target image has been described above, the configuration is not limited thereto. For example, the coverage area may be cumulatively projected between adjacent images by utilizing the deformation parameter about all of the adjacent images between the reference image and the determination target image to calculate the coverage area obtained by projecting the reference image onto the determination target image.

According to this modification, the processing section 100 may calculate the deformation information about adjacent images among the images included in the image sequence and situated between the reference image and the determination target image, and calculate the deformation information about the reference image and the determination target image based on the calculated deformation information about the adjacent images.

According to this configuration, when the reference image and the determination target image are not adjacent to each other, it is possible to calculate the deformation information about the reference image and the determination target image by accumulating the deformation information about adjacent images instead of directly calculating the deformation information about the reference image and the determination target image. The deformation information can be calculated using the method disclosed in JP-A-2011-24763, for example. The processing load imposed by a process that combines a plurality of pieces of deformation information is normally very low as compared with a process that calculates the deformation information from the beginning. For example, when the deformation information is a matrix, the processing load imposed by a process that calculates the matrix from two pieces of image information is heavy, while it is very easy to synthesize a plurality of matrices calculated in advance (since it suffices to calculate the product of the matrices).

This method is particularly effective when implementing a process that utilizes the deformation information a number of times (see the second embodiment), for example. In the second embodiment, the reference image (second reference image) that follows the determination target image is also set in addition to the reference image that precedes the determination target image, and the second reference image is updated corresponding to the conditions. Specifically, when the first image is used as the first reference image, and the kth image is used as the second reference image, whether or not the determination target image can be deleted is determined using the second to (k−1)th images and each reference image, and the second reference image is updated with the (k+1)th image depending on the conditions without updating the first reference image. In this case, the deformation information about each of the second to (k−1)th images and the (k+1)th image (second reference image) is required, and it is necessary to calculate the deformation information k−1 times. Since the required deformation information differs from the deformation information about each of the second to (k−1)th images and the kth image (preceding second reference image), it is necessary to additionally calculate the required deformation information. For example, when the image sequence acquisition section 200 acquires N images as the image sequence, and the second reference image is sequentially updated with the third to Nth images while the first reference image remains unchanged, it is necessary to calculate the deformation information 1+2+3+ . . . +(N−2)=(N−2)(N−1)/2 times. Specifically, it is necessary to perform the deformation information calculation process that imposes a heavy load a number of times, and it is inefficient.

When using the deformation information about adjacent images, it suffices to calculate the deformation information N−1 times when the image sequence acquisition section 200 has acquired N images as the image sequence. In this case, it is necessary to perform a process that synthesizes pieces of deformation information among the N−1 pieces of deformation information when the reference image and the determination target image have been selected from the N images. However, the processing load imposed by the synthesis process is low as compared with the deformation information calculation process.

3. Second Embodiment

The second embodiment illustrates a method that sequentially performs the image summarization process that ensures the coverage ratio by the images that precede or follow the determination target image. A basic method and two modifications are described below.

3.1 Method According to Second Embodiment

Figure 11:
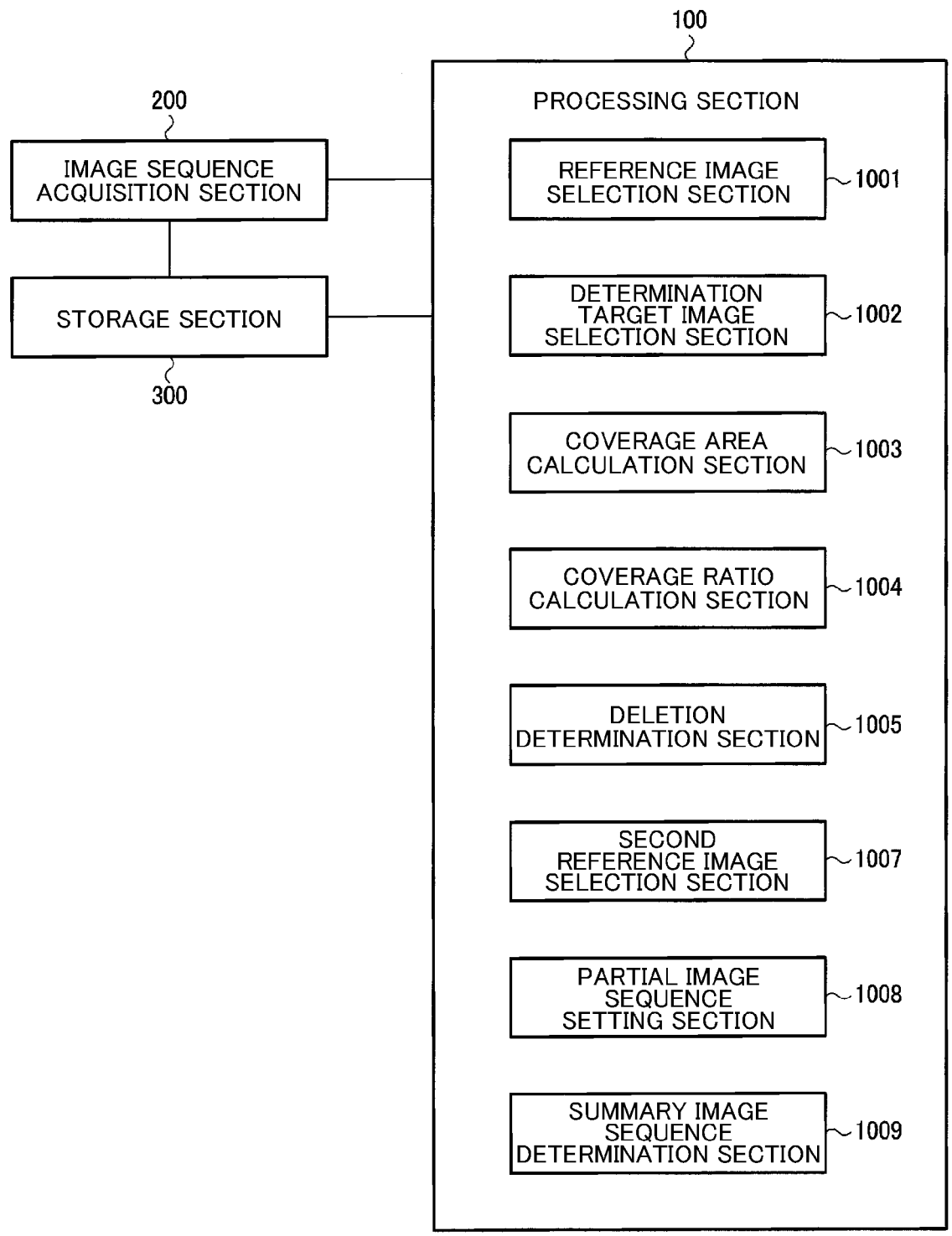
FIG. 11 illustrates a system configuration example of an image processing device according to a second embodiment.

FIG. 11 illustrates a system configuration example of an image processing device according to the second embodiment. The image processing device illustrated in FIG. 11 differs from the image processing device illustrated in FIG. 1 in that the processing section 100 further includes a second reference image selection section 1007.

The reference image selection section 1001 selects a first reference image. The second reference image selection section 1007 selects an image that follows the first reference image at an interval of one or more images as a second reference image. The determination target image selection section 1002 selects an image that follows the reference image and precedes the second reference image as the determination target image. Although FIG. 11 illustrates an example in which the reference image selection section 1001 and the second reference image selection section 1007 are separately provided, the configuration is not limited thereto. For example, the reference image selection section 1001 may select both the first reference image and the second reference image.

Figure 12:
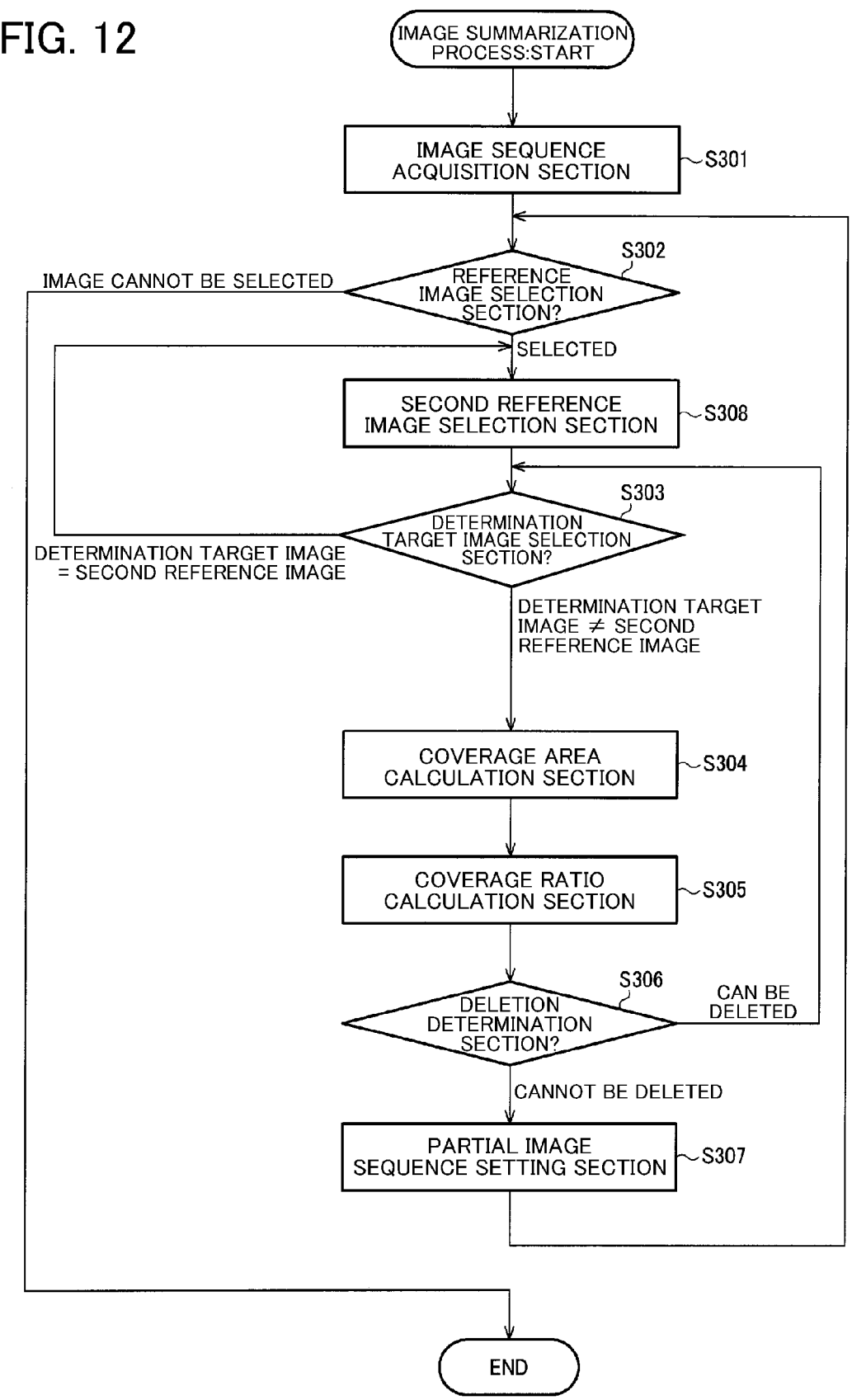
FIG. 12 is a flowchart illustrating a process according to the second embodiment.

FIG. 12 is a flowchart illustrating the image summarization process according to the second embodiment. Note that steps S301 and S302 are the same as the steps S101 and S102, respectively. After the step S302, an image that follows the first reference image selected in the step S302 at an interval of one or more images is selected as the second reference image (S308). The determination target image is set (S303). When the determination target image has not been set, the image that immediately follows the first reference image (i.e., the second image of the input image sequence) is selected as the determination target image. When the kth image of the input image sequence has been selected as the determination target image, the (k+1)th image (i.e., the selection position is shifted by 1) of the input image sequence is selected as the next determination target image. Note that the determination target image selection range is limited to the second reference image instead of the last image of the input image sequence.

When the determination target image does not coincide with the second reference image, the process in the step S304 is performed to calculate the coverage area. Specifically, a first candidate area is calculated based on the deformation parameter about the first reference image and the determination target image, and a second candidate area is calculated based on the deformation parameter about the second reference image and the determination target image. An area corresponding to the sum set of the first candidate area and the second candidate area is set to be the coverage area (see FIG. 8).

Note that steps S304 to S306 are the same as the steps S104 to S106, respectively. When it has been determined that the determination target image can be deleted in the step S306, the determination target image is updated with the image that immediately follows the current determination target image (S303). When the updated determination target image coincides with the second reference image, the second reference image is updated with the image that immediately follows the current second reference image (S308). When the second reference image has been updated, the selected state of the determination target image is reset. When the determination target image does not coincide with the second reference image, the process in the step S304 is performed.

When it has been determined that the determination target image cannot be deleted in the step S306 (i.e., all of the images situated between the first reference image and the current second reference image cannot be covered by the first reference image and the current second reference image), the image that immediately precedes the current second reference image must be allowed to remain in the summary image sequence. Therefore, an image sequence that includes the image that immediately precedes the current second reference image, and the subsequent images is set to be the partial image sequence (S307), and the process in the step S302 is performed.

FIGS. 13A and 13B illustrate the image summarization process described above. Although an example is described below in which the deformation parameter about adjacent images is used cumulatively when projecting the reference image onto the determination target image, the configuration is not limited thereto.

In FIGS. 13A and 13B, the kth image of the image sequence is selected as the first reference image. The first to (k−1)th images have been processed, and the kth to Nth mages have been set to be the partial image sequence. The (k+2)th image is selected as the second reference image.

The image situated between the first reference image and the second reference image is selected as the determination target image, the coverage ratio is calculated by performing the coverage area calculation process based on the first reference image and the determination target image, and the coverage area calculation process based on the second reference image and the determination target image, and whether or not the determination target image can be deleted is determined.

When it has been determined that all of the images situated between the first reference image and the second reference image can be deleted (see FIG. 13A) (i.e., the image that follows the current second reference image can be selected as the second reference image), the next second reference image is selected as illustrated in FIG. 13B. Specifically, the (k+3)th image is selected as the second reference image.

Whether or not the images situated between the first reference image and the second reference image can be deleted is then determined. When it has been determined that the determination target image cannot be deleted (see FIG. 13B) (i.e., all of the images situated between the first reference image and the current second reference image are not covered by the first reference image and the current second reference image) (i.e., the determination target image that cannot be deleted is not covered by the first reference image and the current second reference image), it is considered that the update of the second reference image (increment in the selection position) was inappropriate.

Therefore, an image sequence that includes the image that immediately precedes the current second reference image (corresponding to the second reference image in FIG. 13A), and the subsequent images is set to be the partial image sequence. Therefore, the second reference image in FIG. 13A is selected as the reference image during the subsequent process to ensure that the image to be deleted is covered by the image that is allowed to remain in the summary image sequence.

Figure 14A:
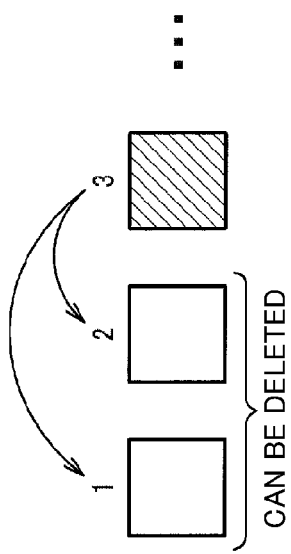
FIGS. 14A to 14D are views illustrating an example of a method according to the second embodiment that selects the first reference image.

Although an example has been described in which the first image of the input image sequence is selected as the reference image in the step S302, the first image of the input image sequence need not necessarily be selected as the reference image when the process in the step S302 is performed for the first time. In the second embodiment, the determination target image can be deleted as long as the determination target image is covered by the second reference image that follows the determination target image. For example, when the first image and the second image are covered by the third image (see FIG. 14A), it is unnecessary to allow the first image and the second image to remain in the summary image sequence. Therefore, the first image need not necessarily be allowed to remain in the summary image sequence. When the first image is used as the reference image, the number of images included in the summary image sequence may unnecessarily increase.

Figure 14B:
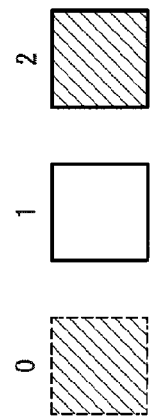
Figure 14C:
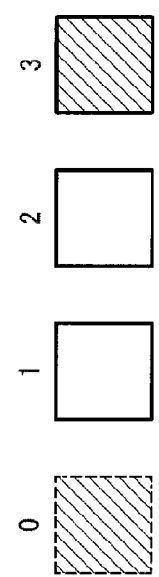
Figure 14D:
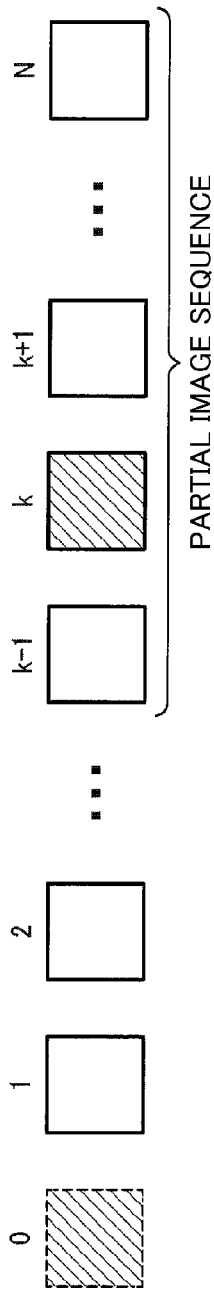

In the second embodiment, the first reference image need not necessarily be the first image of the image sequence acquired by the image sequence acquisition section 200. An example of a specific method is described below. As illustrated in FIG. 14B, a virtual zeroth image is actually selected as the first reference image. Note that this selection process is performed for convenience, and it is unnecessary to actually provide the zeroth image, for example. In this case, the second image is selected by the second reference image selection process in the step S308, and the image (first image) situated between the first reference image and the second reference image is sequentially selected as the determination target image. The process in the steps S304 to S306 is performed on the determination target image and the second reference image since the first reference image is not actually present. When the first image is covered by the second image, the second reference image is updated with the third image according to the process illustrated in FIG. 12 (see FIG. 14C), and whether or not the first image and the second image are covered by the third image is determined. The kth image that cannot cover all of the first to (k−1)th images when the kth image is selected as the second reference image (i.e., the (k−1)th image can cover all of the first to (k−2)th images when the (k−1)th image is selected as the second reference image) (see FIG. 14D) can be found by repeating the above process. In this case, it is determined that the determination target image cannot be deleted in the step S306, an image sequence that includes the (k−1)th to Nth images is set to be the partial image sequence, and the process in the step S302 is performed again. In this case, since the first image of the input image sequence is selected as the reference image during the process in the step S302, the (k−1)th image is allowed to remain in the summary image sequence as the reference image. Since the first to (k−2)th images are covered by the (k−1)th image, the first to (k−2)th images can be deleted, and the number of images included in the summary image sequence can be reduced.

According to the second embodiment, when the first to Nth (N is an integer equal to or larger than 2) images have been input as the input image sequence, the processing section 100 selects the pth image as the first reference image, selects the qth (q is an integer that satisfies $p+2 \leq q \leq N-1$) image as the second reference image, and selects the rth (r is an integer that satisfies $p+1 \leq r \leq q-1$) image as the determination target image. The processing section 100 calculates the coverage ratio based on the deformation information about the first reference image and the determination target image and the deformation information about the second reference image and the determination target image, and determines whether or not the determination target image can be deleted based on the calculated coverage ratio. When it has been determined that the (p+1)th to (q−1)th images can be deleted, the processing section 100 selects the (q+1)th image as the second reference image.

This makes it possible to set the reference images to precede or follow the determination target image (see FIGS. 13A and 13B), and implement the image summarization process based on the coverage ratio. Since two reference images are used, it is likely that it is determined that the determination target image can be deleted, and the number of images included in the summary image sequence (the number of images after the summarization process) can be reduced. Moreover, an image that is temporally (or spatially) close to the determination target image can be set to be the reference image as compared with a method that sets a plurality of reference images to precede the determination target image (see the modification of the first embodiment). Since it is likely that a similar object is captured when the reference image is close to the determination target image, it is likely that the determination target image is determined to be deleted. Note that a plurality of reference images may be set to precede and/or follow the determination target image (see the modification). When it has been determined that the determination target image that is set between the first reference image and the second reference image can be deleted (when all of the determination target images can be deleted in a narrow sense), it is likely that the determination target image that is set between the first reference image and the second reference image can be deleted even when the interval between the first reference image and the second reference image is increased, and the second reference image is updated with the image that follows the current second reference image.

According to the second embodiment, since the reference image can be set to follow the determination target image, the first image need not necessarily be set to be the first image of the image sequence when the process is performed for the first time. If all of the preceding images are covered by a given image that follows the second image, the preceding images can be deleted when the given image is set to be the reference image.

The processing section 100 may perform a process that allows the image selected as the first reference image to remain in the summary image sequence. When it has been determined that at least one of the (p+1)th to (q−1)th images cannot be deleted, the processing section 100 may set a partial image sequence that includes the (q−1)th to Nth images to be the input image sequence, and perform the process on the set input image sequence after setting the value p to 1.

This makes it possible to allow the first reference image to remain in the summary image sequence in the same manner as in the first embodiment in which the reference image is allowed to remain in the summary image sequence. Since the case where at least one of the determination target images situated between the first reference image and the second reference image cannot be deleted corresponds to the case where the interval between the first reference image and the second reference image is increased to a large extent, it is necessary to allow the image that precedes (immediately precedes in a narrow sense) the second reference image to remain in the summary image sequence. Therefore, a partial image sequence that includes the (q−1)th to Nth images is set to be the input image sequence, and the process that selects the first reference image, the second reference image, and the determination target image, the deletion determination process, the second reference image update process (optional), and the like are performed on the set input image sequence. Since it is necessary to allow the first image of the partial image sequence to remain in the summary image sequence, it is desirable to set the parameter p to 1.

3.2 Modification (Another Second Reference Image Update Method)

A modification of the second embodiment is described below. In this modification, a similar expression is repeatedly used in connection with the deletion determination process when describing the second reference image selection method. For convenience of description, the expression "the qth image is OK" is used when the qth image has been selected as the second reference image, and it has been determined by the deletion determination process that all of the images situated between the first reference image and the second reference image can be deleted, and the expression "the qth image is NG" is used when the qth image has been selected as the second reference image, and it has been determined by the deletion determination process that at least one of the images situated between the first reference image and the second reference image cannot be deleted.

According to the above method, the next second reference image is selected when the qth image is OK, but is limited to the (q+1)th image.

When the first to Nth images have been input as the input image sequence, the first image has been selected as the first reference image, and the qth image has been selected as the second reference image, q−2 images (second to (q−1)th images) are candidates for the determination target image, and the determination process is performed q−2 times. If the image summarization process has ended without determining that the determination target image cannot be deleted, a value within the range from 3 to N (N+1 may be included in the range when a virtual image is taken into account) is selected as q, and the process must be performed at least $1+2+3+\ldots+(N-2)=(N-2)(N-1)/2$ times (i.e., the amount of calculations is $N^2$). Specifically, the above method has a disadvantage in that the amount of calculations significantly increases when N is very large.

The amount of calculations can be reduced by increasing the selection range when selecting the next second reference image instead of limiting the selection target to the adjacent image. Specifically, when the qth image is OK, the next second reference image is not limited to the (q+1)th image, but is allowed to be selected from the (q+2)th image and the subsequent images. In this case, even when the qth image is NG, it is unknown whether the (q−1)th image is OK since the (q−1)th image may not have been selected as the second reference image. Therefore, the determination process is basically performed on the preceding image by selecting the image that precedes the qth image as the second reference image instead of necessarily allowing the (q−1)th image to remain in the summary image sequence when the qth image is NG as described above in connection with the basic method according to the second embodiment.

In this modification, the next summary image that follows the first reference image is searched while updating the second reference image with the subsequent image when the qth image is OK, and updating the second reference image with the preceding image when the qth image is NG, until the termination condition is satisfied. The number of images selected as the second reference image until the next summary image is found can be reduced by appropriately setting the position of the second reference image, and the amount of calculations can be reduced. Note that the amount of calculations when using the above method may be smaller than the amount of calculations when using this modification depending on the position of the next summary image that follows the first reference image. The method according to this modification is described in detail below.

A system configuration example of the image processing device is the same as that illustrated in FIG. 11. The second reference image selection process (update process) performed by the second reference image selection section 1007 differs from that described above. The following description focuses on this difference, and detailed description of the same features is omitted.

When the input image sequence has been input, the reference image selection section 1001 selects the first reference image. For example, the reference image selection section 1001 selects the first image of the input image sequence as the first reference image. When the input image sequence is the image sequence acquired by the image sequence acquisition section 200 (i.e., when the first reference image selection process is performed for the first time), an image other than the first image (e.g., a virtual zeroth image) may be selected as the first reference image. Note that the following description is given on the assumption that the first reference image is the first image of the input image sequence unless otherwise specified.

The second reference image is then selected. Specifically, a second reference image selection interval is set that corresponds to the images to be selected as the second reference image (corresponding to the range in which the next summary image that follows the first reference image is searched). A semi-open interval [i, j) corresponding to the ith to jth images is set to be the second reference image selection interval. i corresponds to the image that immediately follows the first reference image (i=2 in a narrow sense), and j is set to N+2. j is set to N+2 since a virtual (N+1)th image can be set to be the second reference image in the same manner as in the case of setting a virtual zeroth image to be the first reference image. A case where the second reference image is the (N+1)th image corresponds to the case where whether or not all of the images that follow the first reference image can be covered only by the first reference image, and the second reference image is unnecessary is determined The second reference image is selected from the second reference image selection interval. The second reference image is determined based on a given condition in order to efficiently perform the process. Specifically, when the second reference image is selected for the first time after the first reference image has been set, the (i+1)th image (third image in a narrow sense) is selected as the second reference image in the same manner as in the basic method according to the second embodiment.

Figure 20A:
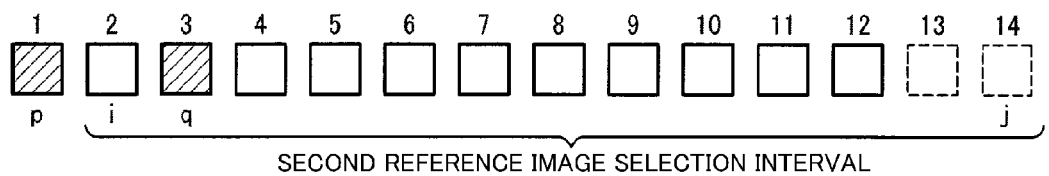
FIGS. 20A to 20G are views illustrating a modification of the second embodiment.

FIG. 20A illustrates the process described above. FIG. 20A illustrates an image sequence in which N=12. The first reference image is the first image, the second reference image selection interval corresponds to the second to fourteenth images (i=2, j=14), and the second reference image is the third image.

After the second reference image has been selected, the determination target image selection process, the coverage ratio calculation process, and the deletion determination process are performed (repeated) in the same manner as described above (detailed description thereof is omitted).

When a given image (the third image during the first process) has been selected as the second reference image, and the given image is OK (i.e., the position of the second reference image can be further shifted away from the first reference image), the image that follows the current second reference image is selected as the next second reference image in the same manner as in the basic method according to the second embodiment. Note that the second reference image may be shifted by two or more images instead of shifting the second reference image by one image.

Figure 20B:
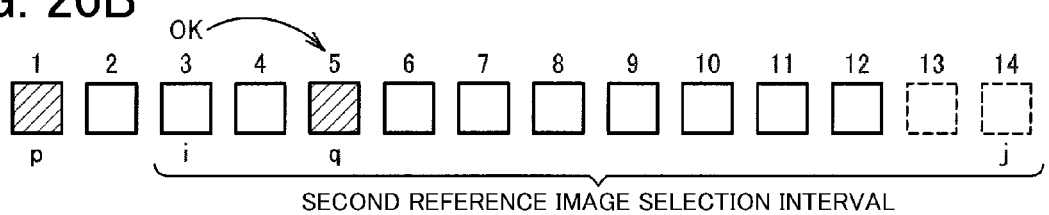

For example, when the current second reference image is the ath image from the first reference image, the (2×a)th image from the first reference image may be selected as the next second reference image. Specifically, when the third image (i.e., the second image from the first reference image) has been selected as the second reference image, and the third image is OK, the fifth image (i.e., the fourth image from the first reference image) is selected as the next second reference image (see FIG. 20B).

When the qth image is OK, it is unnecessary to allow the (q−1)th image and the images that precede the (q−1)th image to remain in the summary image sequence. In this case, the second reference image selection interval may be updated since no advantage is obtained even if the image that precedes the qth image is selected as the second reference image. Specifically, the starting point i of the second reference image selection interval may be set to i=q. Since the second reference image is selected from the second reference image selection interval, the image that precedes the current second reference image is not selected when the starting point i is set to i=q. For example, when the third image is OK (i.e., when the second image is not selected as the summary image), the second image is excluded from the second reference image selection interval, and the starting point of the second reference image selection interval is updated with the third image (see FIG. 20B).

Figure 20C:
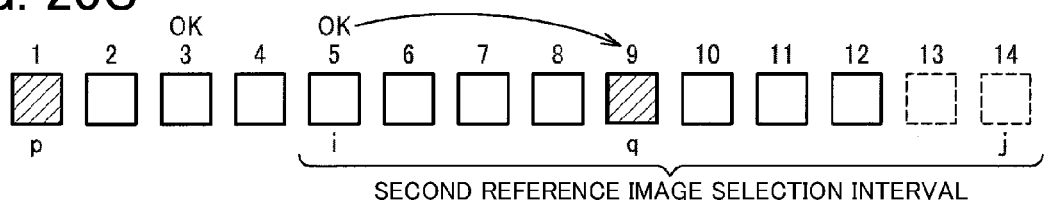

Likewise, when the fifth image is OK, the ninth image is selected as the next second reference image, and the starting point of the second reference image selection interval is updated with the fifth image (see FIG. 20C).

However, when the qth image has been selected as the second reference image, and the qth image is OK, it is likely that an image that is situated significantly away from the qth image is selected as the next second reference image as the value q increases (see FIG. 20C). For example, a situation may occur in which an image that follows the (N+1)th image may be set to be a candidate for the second reference image (i.e., the second reference image cannot be selected), or the interval between the current second reference image and the next second reference image increases to a large extent, and the next summary image search process becomes inefficient.

Therefore, another method may be used in combination when selecting an image that follows the current second reference image as the next second reference image. For example, the next second reference image may be determined based on the value (q+j)/2. For example, when the ninth image is OK, the starting point of the second reference image selection interval is updated with the ninth image (i.e., the second reference image selection interval is a semi-open interval [9, 14)). Specifically, the center of the search range can be set to be the processing target by selecting an image around the center of the search range as the next second reference image. The method that halves the search range by determining the center of the search range is a widely known binary search method, and it is known that the binary search method is advantageous from the viewpoint of the amount of calculations. The binary search method can be applied to the second reference image selection interval since all of the images that precede a given image are determined to be OK when the given image is OK, and all of the images that follow a given image are determined to be NG when the given image is NG. Specifically, it is considered that an efficient process can be implemented by selecting the next second reference image from the center point between the current second reference image and the end point of the second reference image selection interval.

A method that doubles the distance from the first reference image, and a method that corresponds to the binary search method may be used in combination. For example, when the qth image is the current second reference image, the kth image that satisfies the following expression (1) may be selected as the next second reference image. Note that min(a, b) outputs the smaller of a and b.

$$k = \min\left(2q - 1, \frac{q+j}{2}\right) \quad (1)$$

Figure 20D:
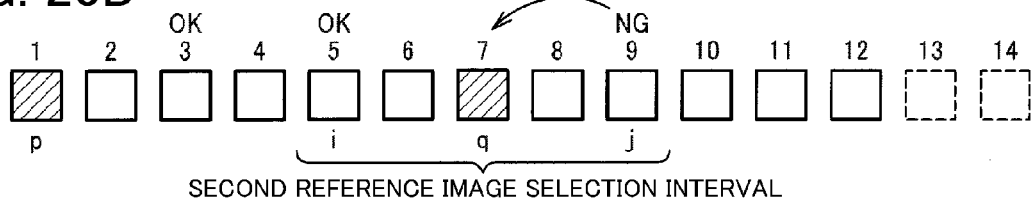

When the qth image is NG, the next second reference image is selected from the images that precede the current second reference image. The next second reference image may be determined using various methods. For example, the next second reference image may be determined using a method that corresponds to the binary search method. In this case, since the starting point of the second reference image selection interval is the ith image, the next second reference image is determined based on the value (i+q)/2. Since the qth image is NG, the qth image and the images that follow the qth image are not selected as the second reference image. Therefore, the end point of the second reference image selection interval can be updated (i.e., j=q). FIG. 20D illustrates an example when the ninth image is NG. The seventh image is selected as the next second reference image, and the end point j of the second reference image selection interval is updated with j=9.

Note that a semi-open interval is used as the second reference image selection interval for convenience of explanation. Specifically, since the qth image may be selected as the summary image when the qth image is OK, it is desirable that the starting point i (i=q) of the second reference image selection interval be included in the second reference image selection interval. Since the qth image is not selected as the summary image when the qth image is NG, it is desirable that the end point j (j=q) of the second reference image selection interval not be included in the second reference image selection interval. Therefore, the second reference image selection interval is represented by [i, j). The second reference image selection interval may be represented by an open interval or a closed interval depending on the sign or the expression.

Figure 20E:
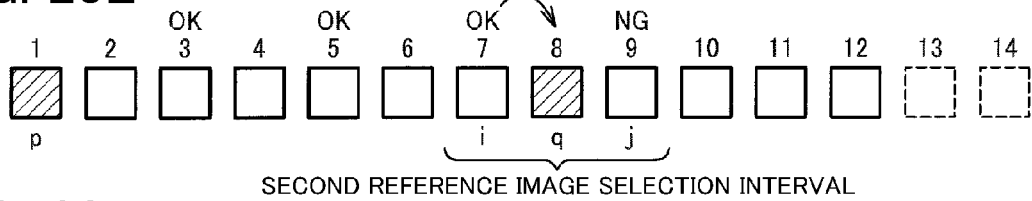
Figure 20F:
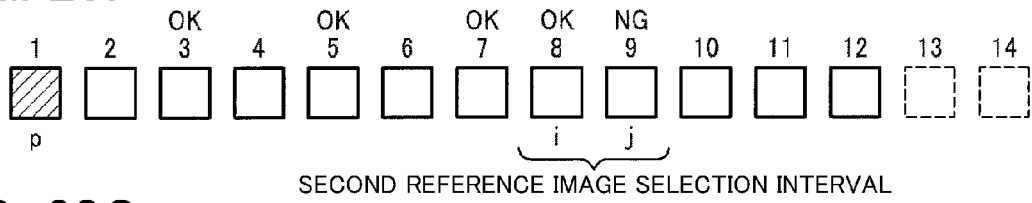
Figure 20G:
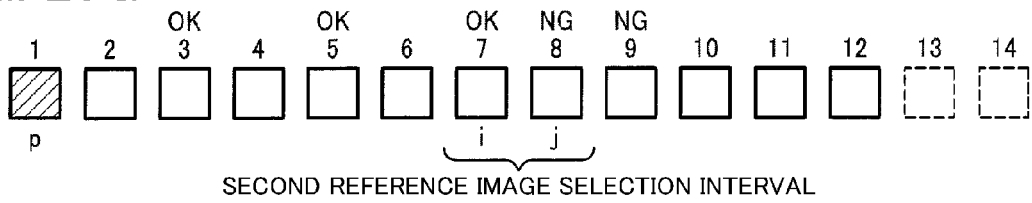

The second reference image selection interval (i.e., the next summary image search range in a narrow sense) is reduced by the above process. Since the next summary image is the kth image when the kth image is OK and the (k+1)th image is NG, the process is terminated when an image that is OK and an image that is NG are adjacent to each other. In the above example, it is considered that the process is performed in a binary search manner (see FIG. 20E). In FIG. 20E, the ith image is OK, the jth image is NG, and the qth image between the ith image and the jth image is selected as the second reference image. FIG. 20F illustrates the case where the qth image is OK, and FIG. 20G illustrates the case where the qth image is NG. In FIGS. 20F and 20G, the starting point and the end point of the second reference image selection interval are adjacent to each other, the image corresponding to the starting point is OK, and the image corresponding to the end point is NG. In this case, the image corresponding to the starting point is selected as the next summary image, and the search process on the input image sequence is terminated.

When the next summary image has been found, a partial image sequence that includes the next summary image and the images that follow the next summary image is set to be the input image sequence in the same manner as in the case of using the basic method according to the second embodiment. Therefore, the partial image sequence setting section 1008 sets the starting point of the second reference image selection interval and the subsequent images to be the partial image sequence, and sets the partial image sequence to be the next input image sequence. The subsequent process is performed in the same manner as described above, and detailed description thereof is omitted.

Figure 21:
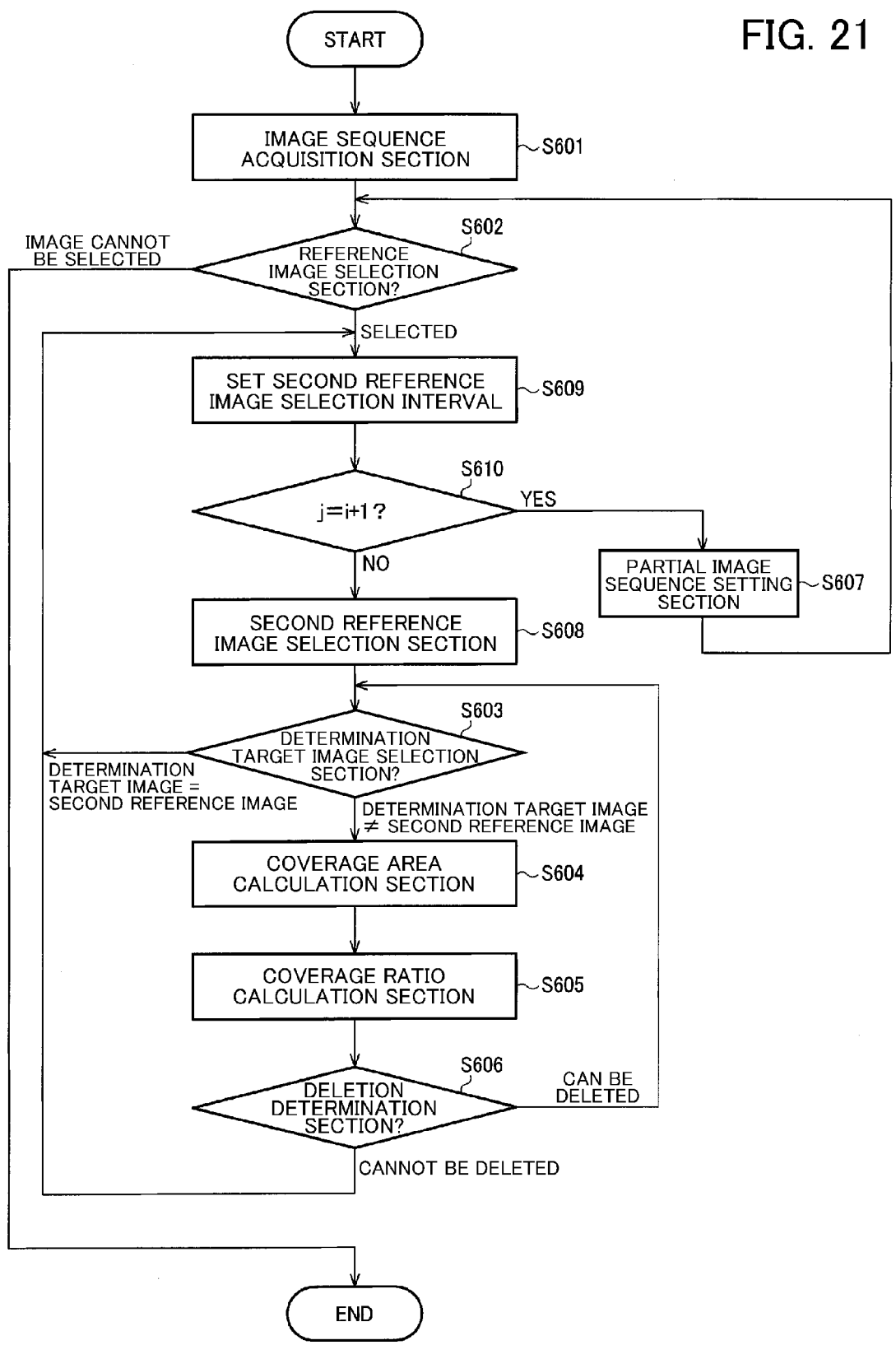
FIG. 21 is a flowchart illustrating a process according to a modification of the second embodiment.

FIG. 21 is a flowchart illustrating the above process. Note that steps S601 and S602 are the same as the steps S301 and S302, respectively. After the first reference image has been selected in the step S602, the second reference image selection interval is set (S609). When the step S609 is performed immediately after the step S602, a semi-open interval [i, j) that satisfies i=2 and j=N+2 may be set, for example. When the step S609 is performed after the step S603 or S606, the second reference image selection interval is updated.

When the second reference image selection interval has been set (or updated) in the step S609, whether or not the starting point and the end point of the second reference image selection interval are adjacent to each other (i.e., whether or not j=i+1 is satisfied) is determined (S610). When it has been determined that the starting point and the end point of the second reference image selection interval are adjacent to each other in the step S610 (i.e., when it has been determined that the ith image is the next summary image that follows the first image (see FIG. 20F)), the ith image and the subsequent images are set to be the partial image sequence (S607), and the process in the step S602 is performed.

When it has been determined that the starting point and the end point of the second reference image selection interval are not adjacent to each other in the step S610 (i.e., when the next summary image has not been found), the second reference image is selected from the second reference image selection interval set in the step S609 (S608). When the process in the step S608 is performed for the first time after the first reference image has been set in the step S602, the (i+1)th image (i.e., the image that follows the first reference image at an interval of one image) may be selected, for example. When the process in the step S608 is not performed for the first time after the first reference image has been set in the step S602, the next second reference image is selected corresponding to the position of the current second reference image.

When the second reference image has been selected in the step S608, the determination target image is selected (S603). The coverage area calculation process (S604), the coverage ratio calculation process (S605), and the deletion determination process (S606) after the determination target image has been selected are performed in the same manner as in the steps S304 to S306, respectively. When it has been determined that the determination target image can be deleted in the step S606, the determination target image is updated with the image that immediately follows the current determination target image (S603), and the process is performed in the same manner as described above. Whether or not all of the images situated between the first reference image and the second reference image can be deleted, or at least one of the images situated between the first reference image and the second reference image cannot be deleted, is determined by repeating the steps S603 to S606. When it has been determined that all of the images situated between the first reference image and the second reference image can be deleted (determination target image=second reference image), the process in the step S609 is performed. When it has been determined that at least one of the images situated between the first reference image and the second reference image cannot be deleted, it is determined that the determination target image cannot be deleted in the step S606, and the process in the step S609 is performed. It is necessary to store information that indicates whether the step S609 is performed after the step S603 or S606, and change the process in the step S609 based on the information (not illustrated in FIG. 21).

When the step S609 is performed after the step S603 (i.e., when all of the images can be deleted), the starting point of the second reference image selection interval is updated, and the image that follows the current second reference image is selected as the next second reference image in the step S608.

When the step S609 is performed after the step S606 (i.e., when at least one of the images cannot be deleted), the end point of the second reference image selection interval is updated, and the image that precedes the current second reference image is selected as the next second reference image in the step S608.

According to this modification, when the pth image is selected from the input image sequence that includes the first to Nth images as the first reference image, and the qth image is selected as the second reference image, the processing section 100 selects the second reference image from the second reference image selection interval in which the starting point and the end point are set corresponding to the (p+2)th to Nth images. The processing section 100 determines whether or not the determination target image can be deleted based on the first reference image and the second reference image. When it has been determined that the (p+1)th to (q−1)th images can be deleted, the processing section 100 selects the xth (x is an integer that satisfies x>q) image included in the second reference image selection interval as the next second reference image. In this case, the processing section 100 may update the starting point of the second reference image selection interval with the qth image.

The second reference image selection interval includes the (p+2)th to Nth images that are candidates for the second reference image. However, since a virtual image (e.g., (N+1)th image) can be selected as the second reference image, the end point of the second reference image selection interval may be larger than N. Since the second reference image selection interval is used as the next summary image search range, an image that is not selected as the second reference image, but may be selected as the summary image may be included in the second reference image selection interval. In this case, the image ((p+1)th image) that immediately follows the first reference image may be set to be the starting point of the second reference image selection interval.

This makes it possible to flexibly determine the position of the next second reference image when updating the second reference image. Since the basic method according to the second embodiment reduces the search range by thoroughly checking the search range from the first image, the amount of calculations may significantly increase depending on the position of the second reference image. In contrast, the search range can be significantly reduced by the unit determination that determines whether the qth image is OK or NG by allowing a non-adjacent image to be selected as the next second reference image. This makes it possible to reduce the amount of calculations, and reduce the load imposed on the system, or reduce the processing time.

When it has been determined that at least one of the (p+1)th to (q−1)th images cannot be deleted, the processing section 100 may select the yth (y is an integer that satisfies y<q) image included in the second reference image selection interval as the next second reference image. In this case, the processing section 100 updates the end point of the second reference image selection interval with the qth image.

This makes it possible to select the image that precedes the current second reference image as the next second reference image when updating the second reference image. Since the search process is not limited to a process that selects the adjacent image, the range that precedes the current second reference image may not have been searched, and may include a correct answer depending on the deletion determination result. In this case, it is possible to perform an appropriate process by performing a forward search process.

Moreover, the next second reference image need not necessarily be selected from the adjacent image in the same manner as in the case of performing a backward search process.

When the jth (j is an integer) image corresponds to the end point of the second reference image selection interval, the processing section 100 may set the value x based on the value $(q+j)/2$. Alternatively, when the ith (i is an integer) image corresponds to the starting point of the second reference image selection interval, the processing section 100 may set the value y based on the value $(i+q)/2$.

This makes it possible to use the binary search method when selecting the next second reference image. The image that is situated between the current second reference image and the end point is selected when performing a backward search process, and the image that is situated between the current second reference image and the starting point is selected when performing a forward search process. This makes it possible to halve the search range (corresponding to the length of the second reference image selection interval). It is expected that the entire search ranges is completely searched when log N images are selected as the second reference image. Therefore, the amount of calculations can be reduced to N×log N. When N is very large, the amount of calculations can be significantly reduced as compared with the basic method according to the second embodiment (the amount of calculations is $N^2$). Note that the value $(q+j)/2$ and the value $(i+q)/2$ are not necessarily an integer, and an image corresponding to each value may be absent. In such a case, the maximum integer that does not exceed the value $(q+j)/2$, or an integer that is larger than the value $(q+j)/2$ by 1 may be used, for example.

The processing section 100 may perform a process that allows the image selected as the first reference image to be included in the summary image sequence when the starting point and the end point of the second reference image selection interval are adjacent to each other as a result of updating the starting point or the end point of the second reference image selection interval. The processing section 100 may set the partial image sequence that includes the image corresponding to the starting point and the images that follow the image corresponding to the starting point in the input image sequence, to be the input image sequence, and perform the process on the set input image sequence after setting the value p to 1.

The expression "the starting point and the end point of the second reference image selection interval are adjacent to each other" means that the image corresponding to the starting point and the image corresponding to the end point are adjacent to each other in the input image sequence. When N images have been provided as the input image sequence, it is considered that the input image sequence is a set of temporally or spatially continuous images. Therefore, the position within the image sequence can be defined based on the continuity. For example, an image acquired at an earlier time precedes an image acquired at a later time. Specifically, when the images included in the input image sequence are referred as first to Nth images, it is determined that an image is situated at a forward position when the number assigned to the image is small. Therefore, j=i+1 is satisfied when the ith image and the jth (>i) mage included in the image sequence are adjacent to each other.

This makes it possible to set a condition based on the starting point and the end point (or the length) of the second reference image selection interval as a condition whereby the process on the input image sequence is terminated. An image among the images that are determined to be OK when selected as the second reference image that is expected to be situated farthest from the first reference image can be selected as the first image (corresponding to the next summary image) of the partial image sequence by setting the termination condition. This is because the termination condition is equivalent to the condition whereby the position at which the image that is OK and the image that is NG are adjacent to each other is searched (see FIG. 20F, for example). This makes it possible to reduce the number of summary images included in the summary image sequence that is output finally, and reduce the burden imposed on the user, for example.

3.3 Modification (Second Reference Image Initial Setting)

According to the second embodiment and the modification thereof, when the input image sequence (that may be the image sequence acquired by the image sequence acquisition section 200, or may be the partial image sequence that is part of the image sequence acquired by the image sequence acquisition section 200) has been input, the second reference image that is set first, is limited to the image that follows the first reference image at an interval of one image.

Note that the initial position of the second reference image may differ from the above position. For example, it is not likely that an interval in which similar images continue and an interval in which the number of similar images is small are adjacent to each other in the actual image sequence. Specifically, it is considered that the length of the next summary interval (that indicates the distance between the adjacent summary images) is close to the length of the preceding summary interval. Therefore, when a plurality of summary images have been obtained, and information that corresponds to the length of the preceding summary interval has been acquired, it is expected that a correct answer is obtained more quickly, and the amount of calculations can be reduced by setting the initial position of the second reference image to a position that is situated away from the first reference image by the length of the preceding summary interval.

Specifically, the length g of the summary interval is acquired from the preceding summary image and the summary image that immediately precedes the preceding summary image. When the second reference image selection interval is [i, j), the second reference image is set to the (i+g)th image instead of the (i+1)th image. Note that the length g of the summary interval cannot be acquired when the number of summary images is 0 or 1. In this case, the initial position of the second reference image is set without using the length g of the summary interval. For example, when the number of summary images is 0, the (i+1)th image may be selected as the second reference image. When the number of summary images is 1, the (i+g')th image may be selected as the first second reference image (g' is the length from the first image of the image sequence acquired by the image sequence acquisition section 200 to the summary image).

The second reference image may be updated in various ways. For example, the next second reference image may be selected using the binary search method (see above).

Since it is likely that the next summary image is present around the (i+g)th image, the number of searches until the next summary image is found may increase when the updated second reference image is situated away from the (i+g)th image. In such a case, the image that is adjacent to the preceding second reference image may be selected as the next second reference image, as described above in connection with the basic method according to the second embodiment. However, since the determination process is not performed on the (i+1)th to (i+g−1)th images, the next summary image may be present within this range. Therefore, the second reference image need not necessarily be updated one by one in the backward direction, but may be updated one by one in the forward direction depending on the deletion determination result.

4. Third Embodiment

Figure 15:
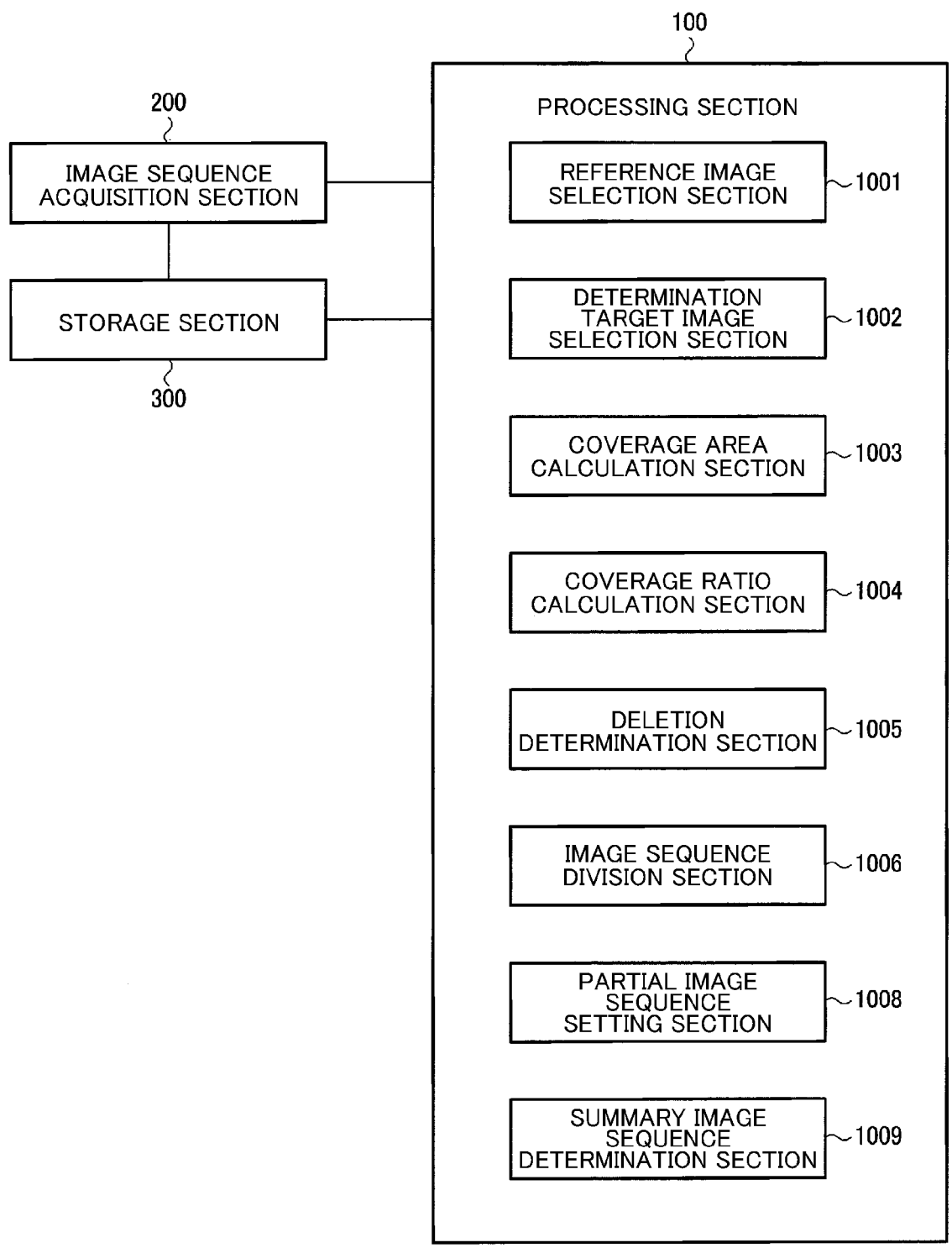
FIG. 15 illustrates a system configuration example of an image processing device according to a third embodiment.

The third embodiment illustrates a method that sequentially performs the image summarization process that ensures the coverage ratio of the images that precede or follow the reference image. FIG. 15 illustrates a system configuration example of an image processing device according to the third embodiment. In FIG. 15, the processing section 100 further includes an image sequence division section 1006 in addition to those illustrated in FIG. 1.

In the third embodiment, the reference image selection section 1001 selects the reference image from the images of the input image sequence other than the first image and the last image (when the number of images included in the input image sequence is 3 or more). The center image of the input image sequence may be selected as the reference image. The determination target image selection section 1002 sequentially selects all of the images included in the input image sequence other than the reference image.

The image sequence division section 1006 divides the input image sequence into a first image sequence that includes the images that precede the reference image, and a second image sequence that includes the images that follow the reference image. The partial image sequence setting section 1008 performs the partial image sequence setting process based on the deletion determination result for each image included in the first image sequence, and performs the partial image sequence setting process based on the deletion determination result for each image included in the second image sequence.

Figure 16:
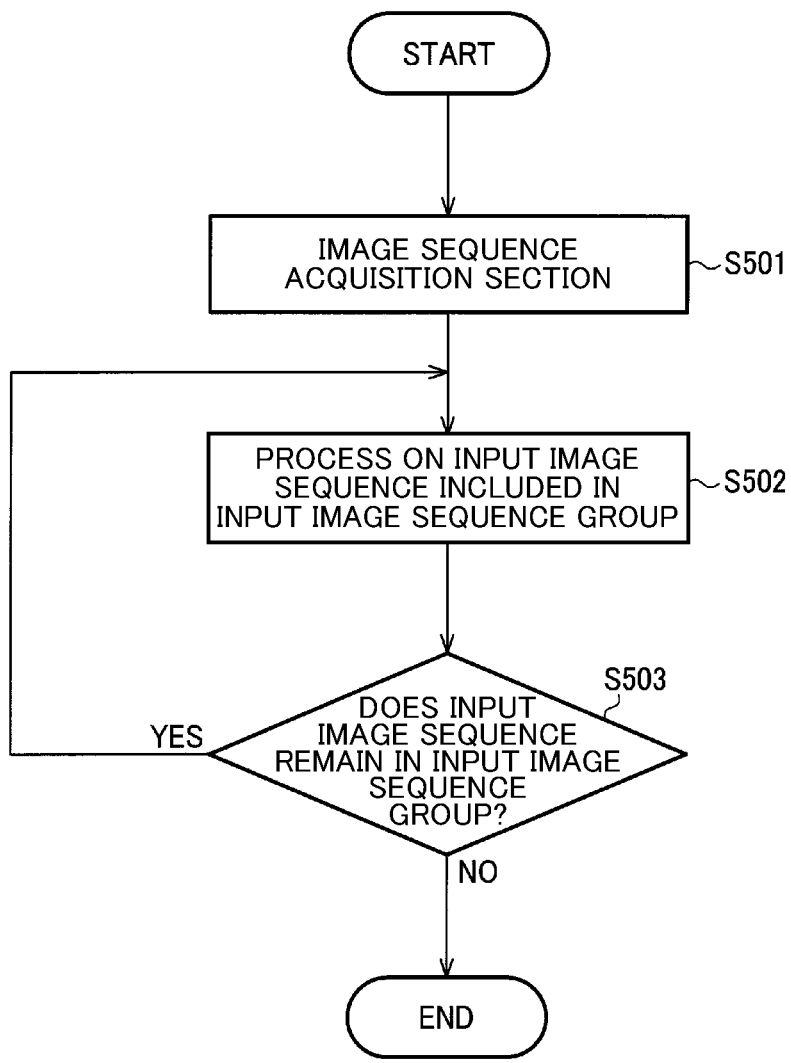
FIG. 16 is a flowchart illustrating a process according to the third embodiment.

FIG. 16 is a flowchart illustrating the image summarization process according to the third embodiment. When the image summarization process has started, the image sequence acquisition section 200 acquires an image sequence subjected to the image summarization process in the same manner as in the step S101 and the like (S501). The image sequence acquired by the image sequence acquisition section 200 is added to an input image sequence group.

Figure 17:
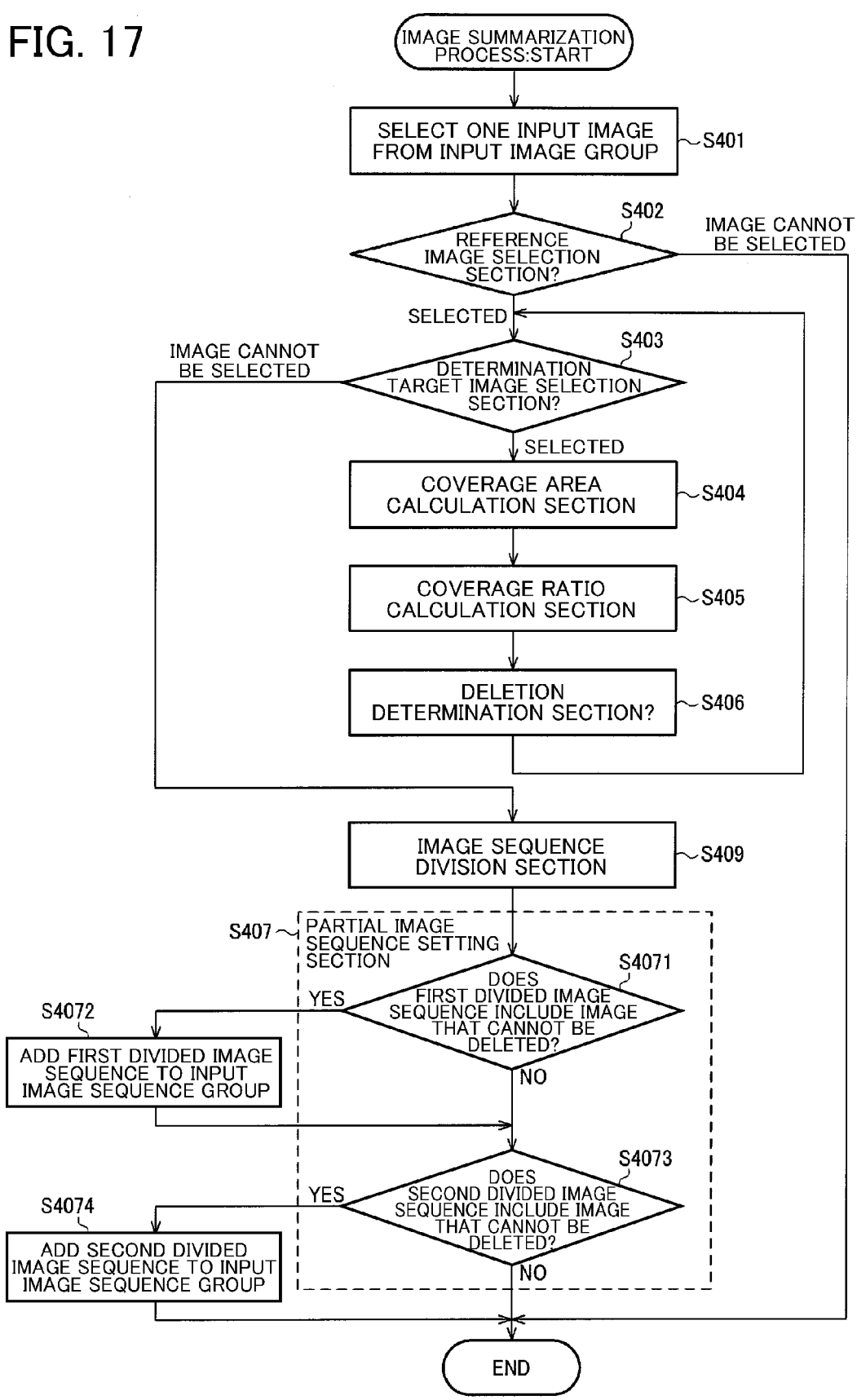
FIG. 17 is another flowchart illustrating a process according to the third embodiment.

A process described later with reference to FIG. 17 is performed on the input image sequence included in the input image sequence group (S502). When the process in the step S502 is performed for the first time, the process is performed on the image sequence acquired in the step S501. Note that the input image sequence subjected to the step S502 is deleted from the input image sequence group. Whether or not the input image sequence remains in the input image sequence group is determined (S503). Since one or two partial image sequences are set during the process in the step S502, and added to the input image sequence group (described later), it may be determined that the input image sequence remains in the input image sequence group in the step S503. The process is terminated when it has been determined that the input image sequence does not remain in the input image sequence group in the step S503.

FIG. 17 is a flowchart illustrating the process in the step S502 illustrated in FIG. 16. The processing target input image sequence is selected from the input image sequence group (S401). Steps S402 to S406 are basically the same as the steps S102 to S106, respectively, except for the difference in the reference image selection position and the like. In the third embodiment, all of the images included in the input image sequence other than the reference image are sequentially selected as the determination target image, and processed regardless of the deletion determination result. When the deletion determination process has been performed on all of the images included in the input image sequence, it is determined that the determination target image cannot be selected in the step S403, and a step S409 is performed.

In the step S409, the input image sequence is divided into the first divided image sequence that includes the images that precede the reference image, and the second divided image sequence that includes the images that follow the reference image. The partial image sequence setting process is performed based on the first divided image sequence and the second divided image sequence (S407). In the step S407, whether or not the first divided image sequence includes at least one image that has been determined to be allowed to remain in the step S406 is determined (S4071). When it has been determined that the first divided image sequence includes at least one image that has been determined to be allowed to remain in the step S406, the first divided image sequence is set to be the partial image sequence, and added to the input image sequence group (S4072). Likewise, whether or not the second divided image sequence includes at least one image that has been determined to be allowed to remain in the step S406 is determined (S4073). When it has been determined that the second divided image sequence includes at least one image that has been determined to be allowed to remain in the step S406, the second divided image sequence is set to be the partial image sequence, and added to the input image sequence group (S4074). Specifically, the process in the step S502 adds 0 to 2 partial image sequences to the input image sequence group as a result of performing the process on one input image sequence.

Figure 18A:
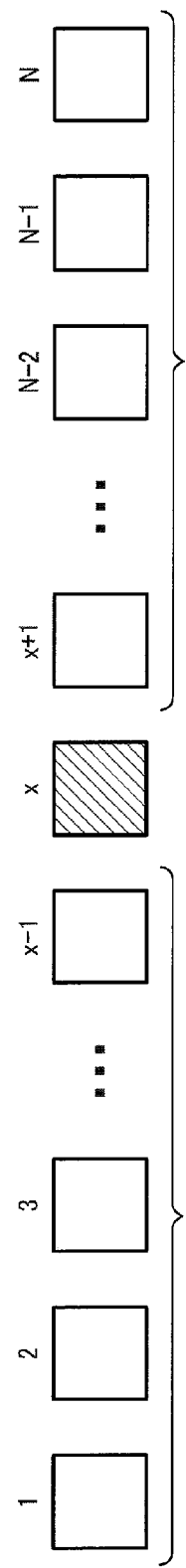
FIGS. 18A and 18B are views illustrating an image summarization process according to the third embodiment.
Figure 18B:
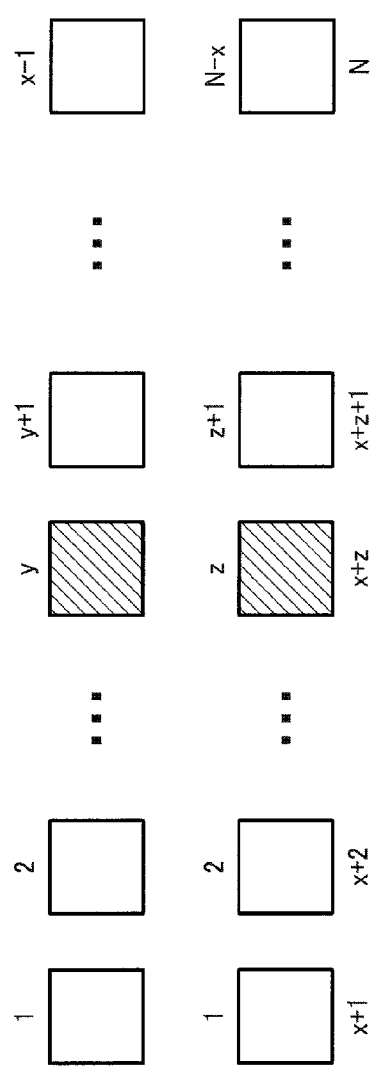

FIGS. 18A and 18B illustrate the image summarization process described above. When an image sequence that includes N images (see FIG. 18A) has been acquired by the image sequence acquisition section 200, the image sequence is added to the input image sequence group, and subjected to the process in the step S502. In the step S502, the xth ($2 \le x \le N-1$ (x is a value close to N/2 in a narrow sense)) image is selected as the reference image, and the first to (x−1)th images and the (x+1)th to Nth images are sequentially selected as the determination target image, and subjected to the deletion determination process.

When it has been determined that at least one image among the first to (x−1)th images cannot be deleted (i.e., when all of the first to (x−1)th images cannot be covered by the reference image), it is necessary to set one of the first to (x−1)th images to be the reference image. Specifically, the first to (x−1)th images are set to be the divided image sequence, and the process in the step S502 is performed again using the divided image sequence as the input image sequence. For example, the yth ($2 \le y \le x-2$ (y is a value close to (x−1)/2 in a narrow sense)) image included in the image sequence that includes x−1 images is selected as the reference image, and the remaining images are sequentially selected as the determination target image, and subjected to the deletion determination process (see FIG. 18B). As a result, a divided image sequence that includes the first to (y−1)th images, and a divided image sequence that includes the (y+1)th to (x−1)th images may be added to the input image sequence group, and subjected to the process in the step S502. The process in the step S502 is repeated until it is determined that all of the images included in the divided image sequence can be deleted (i.e., the divided image sequence is not allowed to remain in the summary image sequence).

The above process is also performed on a divided image sequence that includes the (x+1)th to Nth images (see FIG. 18B).

According to the third embodiment, when first to Nth (N is an integer equal to or larger than 2) images have been input as the input image sequence, the processing section 100 selects the sth (s is an integer that satisfies 2≤s≤N−1) image as the reference image, and selects the tth (t is an integer that satisfies 1≤t≤N and t≠s) image as the determination target image. The processing section 100 calculates the coverage ratio based on the deformation information about the reference image and the determination target image, and determines whether or not the determination target image can be deleted based on the calculated coverage ratio. The processing section 100 sets the partial image sequence that includes the first to (s−1)th images to be the input image sequence when it has been determined that at least one image among the first to (s−1)th images cannot be deleted, and performs the process again. The processing section 100 sets the partial image sequence that includes the (s+1)th to Nth images to be the input image sequence when it has been determined that at least one image among the (s+1)th to Nth images cannot be deleted, and performs the process again.

This makes it possible to implement the process illustrated in FIGS. 18A and 18B. The sth image is desirably an image situated around the center of the input image sequence. Specifically, the input image sequence is divided at the reference image into two divided image sequences, and each of the divided image sequences is subjected to the deletion determination process. When it has been determined that one of the divided image sequences cannot be deleted, the divided image sequence is set to be the input image sequence. Therefore, when one input image sequence has been input, two next input image sequences may be set as the output. In the third embodiment, when it has been determined that at least one image included in the divided image sequence cannot be deleted, the entire divided image sequence is set to be the next input image sequence, and the reference image is selected from the input image sequence. Specifically, it is not determined that a given image is deleted even when it has been determined that the given image can be deleted. The given image may be selected as the reference image when the divided image sequence that includes the given image has been set to be the next input image sequence, and allowed to remain in the summary image sequence (i.e., may not be deleted by the image summarization process).

5. Fourth Embodiment

A basic method that utilizes the observation area is described below. A system configuration example of an image processing device will be described first, the flow of the process will then be described using a flowchart, and the details of the deletion determination process will be described thereafter using three examples.

5.1 System Configuration Example

Figure 22:
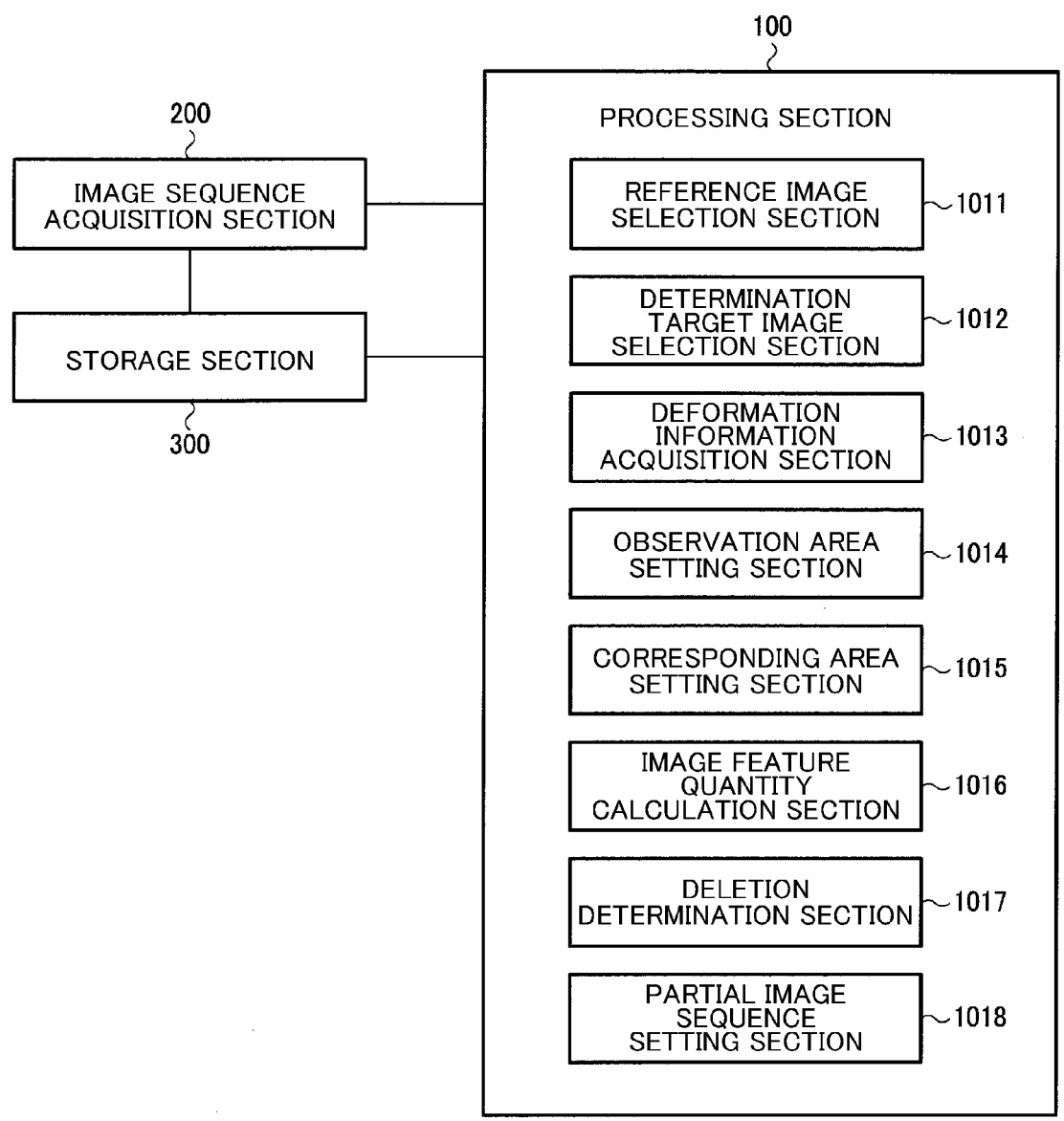
FIG. 22 illustrates a configuration example of an image processing device according to a fourth embodiment.

FIG. 22 illustrates a system configuration example of the image processing device according to the fourth embodiment. The image processing device includes a processing section 100, an image sequence acquisition section 200, and a storage section 300.

As illustrated in FIG. 22, the processing section 100 may include a reference image selection section 1011, a determination target image selection section 1012, a deformation information acquisition section 1013, an observation area setting section 1014, a corresponding area setting section 1015, an image feature quantity calculation section 1016, a deletion determination section 1017, and a partial image sequence setting section 1018.

Note that the reference image selection section 1011 and the determination target image selection section 1012 are respectively the same as the reference image selection section 1001 and the determination target image selection section 1002 illustrated in FIG. 1. The deformation information acquisition section 1013 acquires the deformation information about two images.

The observation area setting section 1014 sets part of the determination target image to be the observation area. The observation area may be a square area having a side of length L, for example. The corresponding area setting section 1015 deforms the observation area based on the deformation information acquired by the deformation information acquisition section 1013 to calculate (set) the corresponding area within the reference image.

The image feature quantity calculation section 1016 calculates the feature quantity of the observation area set by the observation area setting section 1014, and the feature quantity of the corresponding area set by the corresponding area setting section 1015. Specific examples of the feature quantity are described later.

The deletion determination section 1017 determines whether or not the determination target image can be deleted based on the feature quantity (second feature quantity) of the observation area and the feature quantity (first feature quantity) of the corresponding area calculated by the image feature quantity calculation section 1016. The details thereof are described later.

The partial image sequence setting section 1018 sets an image sequence that is included in the image sequence and includes one or more images to be the partial image sequence based on the position of the determination target image in the image sequence when the deletion determination section 1017 has determined that the determination target image cannot be deleted.

5.2 Flow of Process

The flow of the image summarization process according to the fourth embodiment is described below with reference to FIG. 23 (flowchart). When the image summarization process has started, the image sequence that is subjected to the image summarization process is acquired (S701).

The reference image selection section 1011 selects the first image of the input image sequence (i.e., the image sequence acquired in the step S701, or the partial image sequence set in a step S709) as the reference image (S702). The selected reference image is allowed to remain in the summary image sequence. Note that the process is terminated when the reference image cannot be selected from the input image sequence (e.g., when no image is included in the image sequence) due to an error or the like.

The determination target image selection section 1012 selects the determination target image from the images included in the input image sequence (S703). When the determination target image has not been set, the image that immediately follows the reference image (i.e., the second image of the input image sequence) is selected as the determination target image. When the kth image of the input image sequence has been selected as the determination target image, the (k+1)th image (i.e., the selection position is shifted by 1) of the input image sequence is selected as the next determination target image. The process is terminated when the determination target image cannot be selected (e.g., when the number of images included in the input image sequence is less than 2 or k+1).

When the reference image and the determination target image have been selected, the deformation information acquisition section 1013 acquires the deformation information about the reference image and the determination target image (S704). The observation area is set within the determination target image (S705). When the process in the step S705 is performed for the first time after the determination target image has been set in the step S703, the upper left area of the determination target image may be set to be the observation area, for example.

When the observation area has been set, the observation area is deformed based on the deformation information acquired in the step S704, and projected onto the reference image to calculate the corresponding area (S706).

The second feature quantity (i.e., the feature quantity of the observation area) and the first feature quantity (i.e., the feature quantity of the corresponding area) are calculated (S707), and whether or not the determination target image can be deleted is determined based on the calculated first feature quantity and the calculated second feature quantity (S708). The details of the process in the step S707 and the process in the step S708 are described later.

Figure 24:
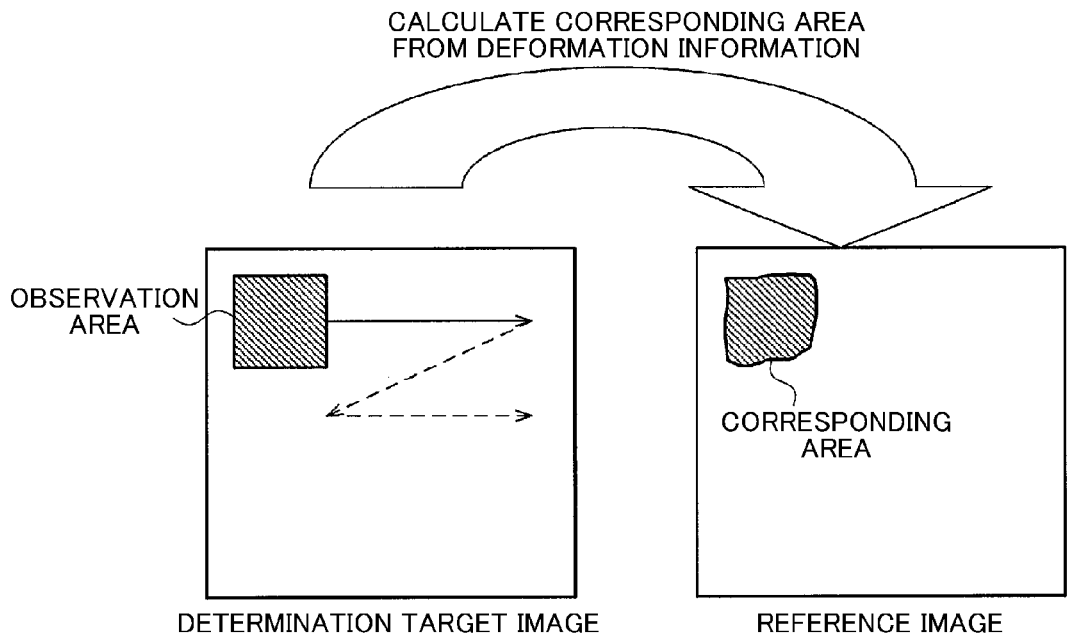
FIG. 24 is a view illustrating an observation area/corresponding area setting method.

When it has been determined that the determination target image can be deleted in the step S708, the observation area is set again in the step S705. Specifically, the position of the observation area is updated. For example, the position of the observation area within the determination target image may be moved from the upper left area in the rightward direction and the downward direction (see FIG. 24). When the observation area has been set, the steps S706 to S708 are performed again.

When the observation area has reached the lower right end in the step S705 (i.e., when it has been determined in the step S708 that the determination target image can be deleted corresponding to all of the observation areas set within the determination target image), it is determined that the determination target image can be deleted, and the determination target image is updated in the step S703.

When it has been determined in the step S708 that the determination target image cannot be deleted while updating the observation area, it is determined that the determination target image cannot be deleted, and the partial image sequence setting section 1018 sets the partial image sequence (S709). Specifically, an image sequence that includes the determination target image that cannot be deleted, and the subsequent images is set to be the partial image sequence. When the partial image sequence has been set, the process in the step S702 is performed using the partial image sequence as the input image sequence. The flow of the image summarization process is the same as described above with reference to FIGS. 4A to 4D.

Figure 23:
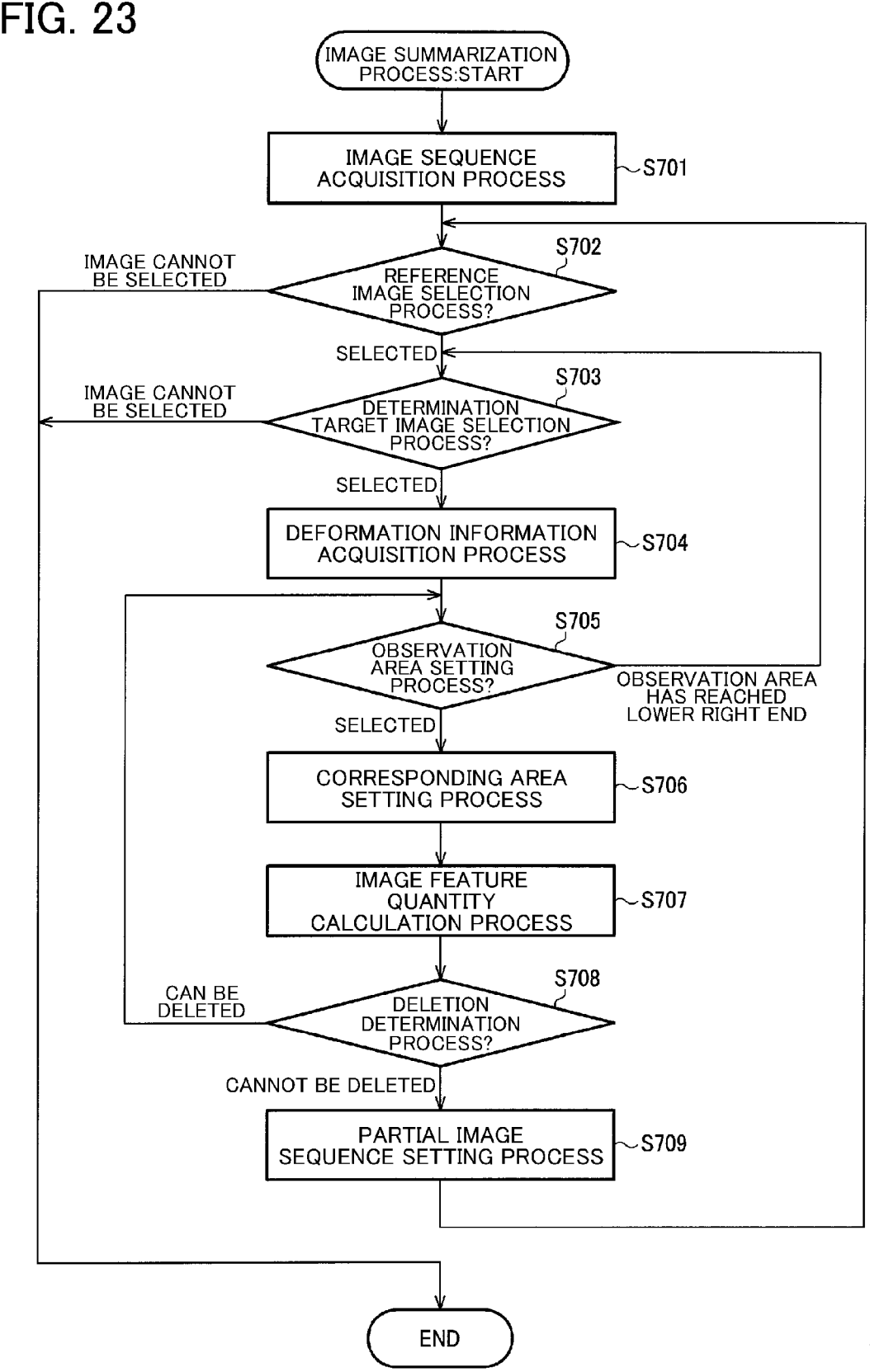
FIG. 23 is a flowchart illustrating an image summarization process according to the fourth embodiment.

Although FIG. 23 illustrates an example in which it is determined that the determination target image cannot be deleted when it has been determined even once in the step S708 that the determination target image cannot be deleted, the configuration is not limited thereto. For example, when the observation area is set within the determination target image up to M (M is an integer equal to or larger than 2) times, an integer t that satisfies 1≤t≤M may be set, and it may be determined that the determination target image cannot be deleted when it has been determined t times or more in the step S708 that the determination target image cannot be deleted. Another method may be used when determining the final result from the results of the deletion determination process in the step S708 that is performed up to M times. For example, various modifications may be made, such as performing a weighting process that attaches importance to the result obtained using the observation area (or the corresponding area) set to the center area of the image as compared with the result obtained using the observation area (or the corresponding area) set to the peripheral area of the image.

5.3 Deletion Determination Process

The details of the feature quantity calculation process in the step S707 and the deletion determination process in the step S708 illustrated in FIG. 23 are described below. Note that the observation area and the corresponding area have been set in advance.

5.3.1 Deletion Determination Based on Brightness Information

A method that utilizes brightness information about the observation area and the corresponding area as the feature quantity is described below. Various index values may be used as the index value that represents the brightness information about an area. For example, the RGB values of the pixels within the area may be converted into the brightness values, and the average value of the brightness values within the area may be used as the feature quantity. Note that the brightness information about the area need not necessarily be calculated from the brightness value of each pixel by calculating the average value of the brightness values. The median value or the like may also be used. The average value need not necessarily be calculated by calculating a simple average value. For example, a weighted average value may be used, or a trimmed average value that excludes an extreme value may be used.

The RGB value of each pixel may be converted into the brightness value using various methods. For example, the maximum value among the R pixel value, the G pixel value, and the B pixel value may be used directly as the brightness value. Note that the brightness value may be calculated using another method.

The deletion determination process based on the first feature quantity (i.e., the brightness information about the corresponding area) and the second feature quantity (i.e., the brightness information about the observation area) is described below. Whether or not the determination target image can be deleted is determined based on two conditions.

The first condition is determined by an upper-limit threshold value K_over and a lower-limit threshold value K_under. Specifically, the first feature quantity is compared with the upper-limit threshold value K_over and the lower-limit threshold value K_under. More specifically, it is determined that the determination target image can be deleted when the first feature quantity satisfies the following expression (2), and it is determined that the determination target image cannot be deleted when the first feature quantity does not satisfy the expression (2).

$$K\_under \leq \text{first feature quantity} \leq K\_over \quad (2)$$

The lower-limit threshold value K_under may be set so that the brightness information is smaller than the lower-limit threshold value K_under when it is difficult to observe the area due to too low a brightness. When the first feature quantity is smaller than the lower-limit threshold value K_under, the corresponding area is normally not suitable for observation due to blocked up shadows.

The upper-limit threshold value K_over may be set so that the brightness information is larger than the upper-limit threshold value K_over when it is difficult to observe the area due to too high a brightness. When the first feature quantity is larger than the upper-limit threshold value K_over, the corresponding area is normally not suitable for observation due to blown out highlights.

Since whether or not blown out highlights or blocked up shadows (or a state close to blown out highlights or blocked up shadows) occur in the corresponding area can be detected by performing a determination based on the expression (2), whether or not it is difficult to observe the object captured within the corresponding area can be determined. Since the corresponding area and the observation area are set based on the deformation information, and have a relationship with the captured object area, it is possible to perform appropriate observation by allowing the determination target image to remain in the summary image sequence, and observing the observation area within the determination target image.

When blown out highlights or blocked up shadows occur in the observation area within the determination target image, the object cannot be observed even if the determination target image is allowed to remain in the summary image sequence. Therefore, it is not advantageous to allow the determination target image to remain in the summary image sequence in such a case. Therefore, whether or not the following expression (3) is satisfied may be determined in addition to determining whether or not the expression (2) is satisfied, and it may be determined that the determination target image cannot be deleted when the expression (2) is not satisfied, and the expression (3) is satisfied, otherwise it may be determined that the determination target image can be deleted.

$$K\_under \leq \text{second feature quantity} \leq K\_over \quad (3)$$

The second condition is determined based on the difference (the absolute value thereof in a narrow sense) between the first feature quantity and the second feature quantity using a given threshold value K_light. Specifically, it is determined that the determination target image cannot be deleted when the following expression (4) is satisfied.

$$|\text{First feature quantity} - \text{second feature quantity}| > K\_light \quad (4)$$

Figure 25:
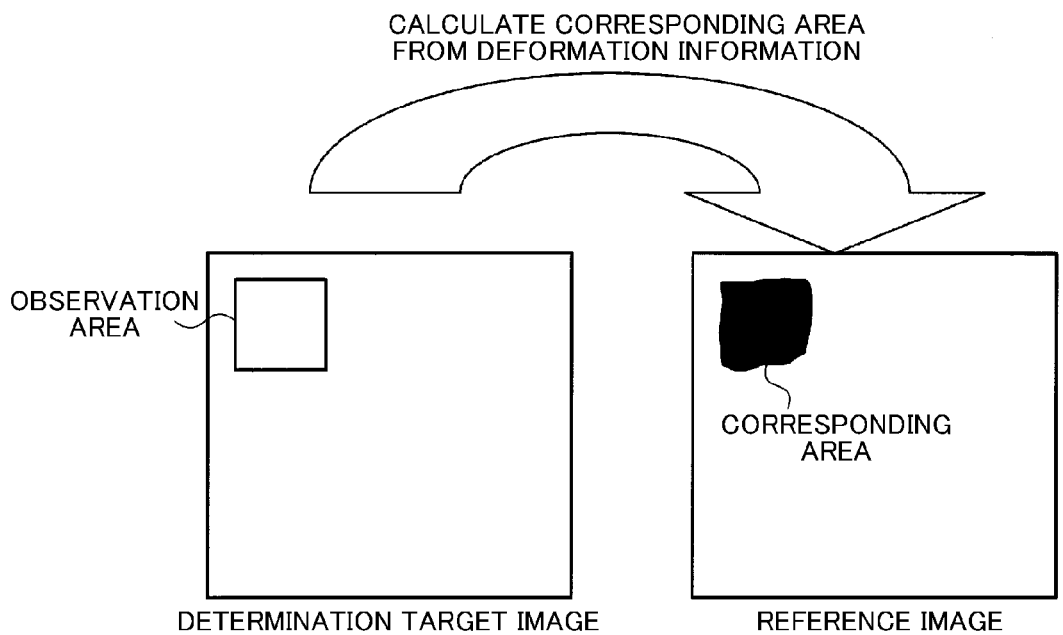
FIG. 25 illustrates an example in which brightness information is used as a feature quantity.

The absolute value of the difference between the first feature quantity and the second feature quantity is large when the brightness of the corresponding area and the brightness of the observation area differ from each other to a large extent (see FIG. 25). It is considered that a preferable brightness when observing the object differs depending on the type of the object and the like. The object may be easily observed when the image is bright, or may be easily observed when the image is dark. The expression (4) is satisfied when one of the first feature quantity and the second feature quantity is large, and the other of the first feature quantity and the second feature quantity is small (depending on the threshold value K_light). This corresponds to an extreme situation in which one of the corresponding area and the observation area is bright, and the other of the corresponding area and the observation area is dark. Specifically, since the brightness of the corresponding area is not an intermediate value that can be used in a versatile way, it may be difficult to observe the object captured within the corresponding area depending on the situation. It is likely that appropriate observation can be performed when the determination target image that includes the observation area that significantly differs in brightness from the corresponding area is allowed to remain in the summary image sequence.

There may be a case where the corresponding area is suitable for observation, and the observation area is not suitable for observation even when the expression (4) is satisfied. However, a brightness suitable for observation differs depending on the situation, and it is difficult to determine such a brightness in advance. Therefore, the determination target image is allowed to remain in the summary image sequence when the expression (4) is satisfied. Specifically, the method according to the fourth embodiment allows an unnecessary determination target image to remain in the summary image sequence depending on the situation.

5.3.2 Deletion Determination Based on Size Information

A method that utilizes size information about the observation area and the corresponding area as the feature quantity is described below. The size information corresponds to the area of each area. For example, the size information may be calculated by counting the number of pixels included in each area. Note that the size information may be calculated using another method.

A situation in which the size of the corresponding area decreases to a large extent, and the object cannot be appropriately observed (see FIG. 26) is taken into account when using the size information as the feature quantity. Therefore, the determination target image is allowed to remain in the summary image sequence when the first feature quantity that is the size information about the corresponding area is small so that the object that cannot be appropriately observed within the corresponding area can be observed within the observation area within the determination target image. The deletion determination process may be performed using only the size of the corresponding area (i.e., using only the first feature quantity). In this example, the deletion determination process is performed using a relative size (e.g., the ratio of the size of the observation area to the size of the corresponding area). For example, it is determined that the size of the corresponding area has decreased to a level that is not suitable for observation, and the determination target image cannot be deleted when the following expression (5) is satisfied.

$$(\text{Second feature quantity}/\text{first feature quantity}) > K\_area \quad (5)$$

Note that the expression used for the determination is not limited to the expression (5). It suffices that the expression used for the determination be based on the difference between the first feature quantity and the second feature quantity. For example, the difference between the logarithm of the second feature quantity and the logarithm of the first feature quantity may be calculated, and compared with a given threshold value. The difference between the second feature quantity and the first feature quantity may be calculated, and compared with a given threshold value.

5.3.3 Deletion Determination Based on Similarity with Given Shape

A method that utilizes the similarity of the observation area and the corresponding area with a given shape as the feature quantity is described below. The similarity with the given shape represents the degree by which each area is similar to the given shape. For example, when the given shape is a circle, the degree of circularity calculated by the following expression (6) may be used as the feature quantity. Note that the given shape is not limited to a circle, and the similarity calculation method is not limited to the method using the expression (6).

$$\text{Degree of circularity}=(4\pi\times\text{area})/(\text{circumferential length})^2 \qquad (6)$$

Figure 27:
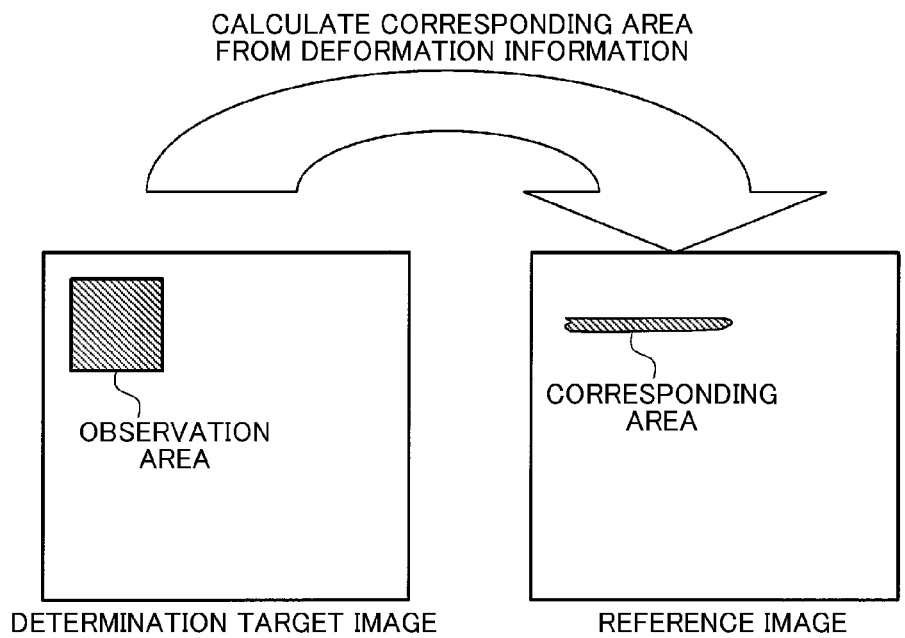
FIG. 27 illustrates an example in which the similarity with a given shape is used as a feature quantity.

A situation in which the corresponding area has an extreme shape, and the object cannot be appropriately observed (see FIG. 27) is taken into account when using the similarity with the given shape as the feature quantity. In FIG. 27, the corresponding area has a rectangular shape in which the short side is extremely shorter than the long side, and the object is compressed in the short-side direction. Therefore, a simple shape (e.g., circle or square) that is suitable for observation is set as the given shape, and the determination target image is allowed to remain in the summary image sequence when the first feature quantity that is the similarity of the corresponding area with the given shape is small so that the object that cannot be appropriately observed within the corresponding area can be observed within the observation area within the determination target image. The deletion determination process may be performed using only the similarity of the corresponding area (i.e., using only the first feature quantity). In this example, the deletion determination process is performed using relative information (e.g., the ratio of the similarity of the observation area to the similarity of the corresponding area). For example, it is determined that the shape of the corresponding area is not suitable for observation, and the determination target image cannot be deleted when the following expression (7) is satisfied.

$$(\text{Second feature quantity/first feature quantity})>K\_\text{shape} \qquad (7)$$

Note that the expression used for the determination is not limited to the expression (7) in the same manner as in the case of using the size information. For example, the difference between the logarithm of the second feature quantity and the logarithm of the first feature quantity may be calculated, and compared with a given threshold value. The difference between the second feature quantity and the first feature quantity may be calculated, and compared with a given threshold value.

5.3.4 Combination of Determinations that Utilize a Plurality of Feature Quantities Two or more deletion determination processes among the deletion determination process that utilizes the brightness information, the deletion determination process that utilizes the size information, and the deletion determination process that utilizes the similarity with a given shape may be used in combination.

The deletion determination processes may be combined in various ways. If priority is given to prevention of occurrence of an area that is not suitable for observation, the probability that it is determined that the determination target image cannot be deleted is increased. Therefore, when using a plurality of types of feature quantities, the deletion determination process is performed using each feature quantity, and the determination target image is deleted when it has been determined by each deletion determination process that the determination target image can be deleted. The determination target image is not deleted when it has been determined by at least one deletion determination process that the determination target image cannot be deleted. According to this configuration, the determination target image is allowed to remain when it has been determined from at least one feature quantity that the corresponding area is not suitable for observation, and it is likely that the target object can be appropriately observed.

However, when it is easily determined that the determination target image cannot be deleted, the number of images that are allowed to remain in the summary image sequence increases, and the effect of reducing the number of images may decrease. Therefore, when priority is given to a reduction in the number of images, a method may be used that determines that the determination target image can be deleted with higher probability.

For example, even when the determination target image is not deleted when it has been determined by at least one deletion determination process among a plurality of deletion determination processes that the determination target image cannot be deleted, the determination condition used for the deletion determination process that utilizes each feature quantity may be changed. For example, when using the size information and the similarity with a given shape in combination, the value K_area and the value K_shape may be increased as compared with the case of independently using the size information and the similarity with a given shape. In this case, since it is easily determined by each deletion determination process that the determination target image can be deleted, it is possible to prevent a situation in which the number of images included in the summary image sequence increases to a large extent while implementing a determination based on the size and the similarity.

According to the fourth embodiment, the image processing device includes the image sequence acquisition section 200 that acquires an image sequence that includes a plurality of images, and the processing section 100 that performs the image summarization process that deletes some of the plurality of images included in the image sequence acquired by the image sequence acquisition section 200 to acquire a summary image sequence (see FIG. 22). The processing section 100 selects the reference image and the determination target image used for the image summarization process from the plurality of images, sets the observation area within the determination target image, and calculates the corresponding area (i.e., an area of the reference image that corresponds to the observation area) based on the deformation information about the reference image and the determination target image. The processing section 100 determines whether or not the determination target image can be deleted based on at least one of the first feature quantity calculated from the corresponding area and the second feature quantity calculated from the observation area.

The observation area is an area that is set within the determination target image. The observation area is an area narrower than the determination target image in a narrow sense. When determining whether or not the entirety of the object captured within the determination target image is suitable for observation within the reference image, it is necessary to set the observation area a plurality of times to cover the entire determination target image while changing the position of the observation area within the determination target image when the reference image and the determination target image have been selected. For example, each pixel included in the determination target image is included in the observation area at least once. This is implemented by setting the observation area while shifting the observation area by one pixel in the rightward direction and the downward direction from the upper left area (see FIG. 24). However, since the processing load increases as the observation area is set a larger number of times, the amount of calculations may be reduced by shifting the observation area by the length of one side of the observation area.

When using the size information as the feature quantity, an area that is necessary and sufficient for appropriate observation may be set to be the observation area. In this case, since the second feature quantity represents an appropriate reference value, whether or not the corresponding area has a size suitable for observation can be determined by comparing the second feature quantity with the first feature quantity, for example. When using the similarity with a given shape (i.e., a shape (e.g., circle or square) that is suitable for observation) as the feature quantity, the observation area may have a shape similar to the given shape (the same shape as the given shape in a narrow sense). It is considered that an area having a constant size and a constant shape is used as the observation area during a series of processes. Note that the observation area may be set variably.

This makes it possible to determine whether or not the determination target image can be deleted based on the feature quantity of the observation area within the determination target image, and the feature quantity of the corresponding area within the reference image. When the corresponding area is an area calculated by deforming the observation area based on the deformation information, the object captured within the observation area corresponds to the object captured within the corresponding area. Therefore, when it has been determined that the corresponding area is not suitable for observation based on the feature quantity, it suffices to allow the observation area in which the corresponding object (identical object in a narrow sense) is captured to be observed after the image summarization process. This is implemented by allowing the determination target image to remain in the summary image sequence (i.e., determining that the determination target image cannot be deleted).

The first feature quantity may be at least one of the brightness information about the corresponding area, the size information about the corresponding area, and the similarity information about the similarity of the corresponding area with a given (specific) shape. The second feature quantity may be at least one of the brightness information about the observation area, the size information about the observation area, and the similarity information about the similarity of the observation area with a given shape.

The similarity of a given area with a given shape is an index value that represents the degree by which the given area is similar to the given shape. For example, when the given shape is a circle, a k-sided regular polygonal area (k is an integer equal to or larger than 3) has a lower degree of similarity with the given shape as the value k decreases, and has a higher degree of similarity with the given shape as the value k increases. When the given shape is symmetrical (e.g., circle), a symmetrical area tends to have a higher degree of similarity with the given shape as compared with an asymmetrical area.

This makes it possible to use at least one of the brightness information, the size information, and the similarity information about the similarity with a given shape as the feature quantity. Specifically, the image processing device according to the fourth embodiment determines whether or not the object within the corresponding area is suitable for observation based on the brightness, the size, or the shape, and allows the determination target image to remain in the summary image sequence when the object within the corresponding area is not suitable for observation. It may be determined that the object within the corresponding area is not suitable for observation when the brightness is too high (blown out highlights), when the brightness is too low (blocked up shadows), when the size is extremely small, or when the shape is extreme (e.g., when the shape is deformed or distorted), for example.

The processing section 100 may determine whether or not the determination target image can be deleted based on at least one comparison process among a first comparison process that compares the first feature quantity with a first threshold value, a second comparison process that compares the second feature quantity with a second threshold value, and a third comparison process that compares the degree of difference between the first feature quantity and the second feature quantity with a third threshold value.

The degree of difference between the first feature quantity and the second feature quantity that represents the difference between the first feature quantity and the second feature quantity is calculated by the difference, the ratio, or a value corresponding thereto (e.g., the difference between the logarithm of the first feature quantity and the logarithm of the second feature quantity). When using the brightness information as the feature quantity, the degree of difference between the first feature quantity and the second feature quantity is high when one of the corresponding area and the observation area is bright, and the other of the corresponding area and the observation area is dark. When using the size information as the feature quantity, the degree of difference between the first feature quantity and the second feature quantity is high when one of the corresponding area and the observation area has a large area, and the other of the corresponding area and the observation area has a small area. When using the similarity with the given shape as the feature quantity, the degree of difference between the first feature quantity and the second feature quantity is high when one of the corresponding area and the observation area has a shape similar to the given shape, and the other of the corresponding area and the observation area has a shape that differs to a large extent from the given shape.

This makes it possible to perform the deletion determination process based on at least one comparison process among the first to third comparison processes. The first comparison process is performed based on the first feature quantity that is the feature quantity of the corresponding area. For example, the first comparison process may be used when a determination can be made independently of the state of the observation area (e.g., when determining whether or not blown out highlights or blocked up shadows occur in the corresponding area (see the expression (2)). The second comparison process is performed based on the second feature quantity that is the feature quantity of the observation area. For example, the second comparison process may be used when determining whether or not blown out highlights or blocked up shadows occur in the observation area (see the expression (3)). The second comparison process may be used alone. However, it is desirable to use the second comparison process in combination with the first comparison process or the like taking account of the effect of reducing the number of images through the image summarization process. Since the third comparison process is based on the degree of difference between the first feature quantity and the second feature quantity, the third comparison process takes account of the state of the corresponding area and the state of the observation area. It is possible to perform an accurate deletion determination process by utilizing the third comparison process. Note that the two feature quantities used for the third comparison process must correspond to each other (e.g., a comparison between the brightness information about the corresponding area and the size information about the observation area is not useful). Specifically, when one of the two feature quantities used for the third comparison process is the brightness information, the other of the two feature quantities used for the third comparison process is also the brightness information. When one of the two feature quantities used for the third comparison process is the size information, the other of the two feature quantities used for the third comparison process is also the size information. When one of the two feature quantities used for the third comparison process is the similarity with the given shape, the other of the two feature quantities used for the third comparison process is also the similarity with the given shape.

The processing section 100 may calculate the brightness information about the corresponding area as the first feature quantity based on the pixel value of each pixel included in the corresponding area, and calculate the brightness information about the observation area as the second feature quantity based on the pixel value of each pixel included in the observation area.

This makes it possible to perform the deletion determination process using the brightness information as the feature quantity. The brightness information about the corresponding area and the brightness information about the observation area are calculated based on the brightness calculated corresponding to each pixel included in each area. For example, the maximum value among the R pixel value, the G pixel value, and the B pixel value is used as the brightness of each pixel. Note that the brightness of each pixel may be calculated using another method (e.g., a method that calculates the average value of the maximum value and the minimum value). The brightness information about each area may be calculated from the brightness of each pixel by calculating the average value of the brightness of each pixel included in each area. Note that the brightness information about each area may be calculated using another method (e.g., a method that calculates the median value, a weighted average value, or a trimmed average value). Specific examples of the deletion determination process based on the brightness information include a process that determines that the determination target image cannot be deleted when the corresponding area is not suitable for observation due to blown out highlights or blocked up shadows. In this case, the determination target image that includes the observation area in which the same object as that captured within the corresponding area is considered to be captured can be allowed to remain in the summary image sequence, and the object can be appropriately observed.

The processing section 100 may determine that the determination target image cannot be deleted when the first feature quantity that is the brightness information is larger than a given upper-limit threshold value, or when the first feature quantity is smaller than a given lower-limit threshold value.

This makes it possible to implement the process represented by the expression (2). This process takes account of a situation in which blown out highlights or blocked up shadows (or a state close to blown out highlights or blocked up shadows) occur in the corresponding area. Therefore, the upper-limit threshold value may be set so that the brightness information is larger than the upper-limit threshold value when the object is not suitable for observation due to too high a brightness, and the lower-limit threshold value may be set so that the brightness information is smaller than the lower-limit threshold value when the object is not suitable for observation due to too low a brightness.

The processing section 100 may calculate a value represented by the size information about the corresponding area as the first feature quantity, and calculate a value represented by the size information about the observation area as the second feature quantity.

This makes it possible to perform the deletion determination process using the size information as the feature quantity. For example, information that corresponds to the area of each area may be used as the size information. Specifically, the size information may be calculated by counting the number of pixels included in each area. Specific examples of the deletion determination process based on the size information include a process that determines that the determination target image cannot be deleted when the corresponding area has a very small area, and is not suitable for observation (i.e., the object cannot be appropriately observed) (see FIG. 26).

The processing section 100 may calculate a value that represents the similarity of the corresponding area with a given shape as the first feature quantity, and calculate a value that represents the similarity of the observation area with a given shape as the second feature quantity.

This makes it possible to perform the deletion determination process using the similarity with the given shape as the feature quantity. When the given shape is a circle, the degree of circularity represented by the expression (6) may be used as the similarity with the given shape, for example. Specific examples of the deletion determination process based on the similarity with the given shape include a process that determines that the determination target image cannot be deleted when the corresponding area has an extreme shape, and is not suitable for observation (i.e., the object is deformed in the vertical direction) (see FIG. 27).

The processing section 100 may determine that the determination target image cannot be deleted when the degree of difference between the first feature quantity and the second feature quantity is larger than a given threshold value.

This makes it possible to perform the deletion determination process using the feature quantity of the corresponding area and the feature quantity of the observation area. When using the brightness information as the feature quantity, the degree of difference between the first feature quantity and the second feature quantity is high when one of the corresponding area and the observation area is bright, and the other of the corresponding area and the observation area is dark. The brightness value suitable for observation cannot be uniquely determined. For example, the brightness value suitable for observation varies depending on the relationship with the shape/color of the object, the color of the background that is captured behind the object, or the like. If the brightness information about the corresponding area represents an intermediate value, the brightness information may be used in a versatile way to a certain extent. However, it is not considered that the brightness information can be used in a versatile way when the degree of difference is high. Specifically, when the degree of difference is high (e.g., when the expression (4) is satisfied), it is necessary to consider that the corresponding area may have a brightness that is not suitable for observation, and it is desirable to determine that the determination target image cannot be deleted. Note that the determination target image that includes the observation area that is not suitable for observation may be allowed to remain in the summary image sequence due to the process that utilizes the expression (4) or the like even when the corresponding area is suitable for observation.

When using the size information as the feature quantity, whether or not the corresponding area has a small area is taken into consideration, and it is not effective to allow the determination target image to remain in the summary image sequence when the observation area does not have an area suitable for observation. Therefore, it is desirable to detect that the corresponding area is sufficiently smaller than the observation area (see the expression (5)) as a situation in which the degree of difference is high. When using the size information as the feature quantity, it is considered that the second feature quantity is constant when the size and the shape of the observation area are constant, and a value calculated in advance may be continuously used. In such a case, since the second feature quantity in the expression (5) is constant, the determination process is substantially performed based on the first feature quantity. However, when the observation area is set dynamically (e.g., when the observation area changes according to an instruction issued by the user, or an area corresponding to the attention area detected by image processing is set to be the observation area), it is necessary to calculate the second feature quantity each time the observation area is set.

When using the similarity with the given shape (that is suitable for observation) as the feature quantity, whether or not the corresponding area has an extreme shape is taken into consideration, and it is not effective to allow the determination target image to remain in the summary image sequence when the shape of the observation area is not close to the given shape to a certain extent. Therefore, it is desirable to detect that the similarity of the corresponding area is sufficiently smaller than the similarity of the observation area (see the expression (7)) as a situation in which the degree of difference is high. In this case, the second feature quantity can be calculated in advance when the shape of the observation area is constant. For example, an area having the same shape as the given shape may be set to be the observation area.

6. Fifth Embodiment

A method that utilizes the deletion determination process that utilizes the first feature quantity and the second feature quantity (described above in connection with the fourth embodiment) (hereinafter referred to as "first deletion determination process") in combination with a second deletion determination process that differs from the first deletion determination process is described below.

Specifically, the second deletion determination process is performed on each image included in the image sequence acquired by the image sequence acquisition section 200 to set a summary candidate image sequence that includes summary images that have been determined to be allowed to remain, and a deletion candidate image sequence that includes deletion candidate images that have been determined to be deleted. The first deletion determination process is then performed to generate the summary image sequence. When performing the first deletion determination process, the reference image is selected from the summary candidate image sequence, and the determination target image is selected from the deletion candidate image sequence.

Specifically, the method according to the fifth embodiment implements a two-step process that performs the second deletion determination process as preprocessing to provisionally determine the images that are allowed to remain and the images that are deleted, and performs the first deletion determination process using the provisional results to determine the final results. This makes it possible to improve the determination accuracy as compared with the case of performing the image summarization process based on only one of the first deletion determination processes and the second deletion determination process, for example. Specifically, since the second deletion determination process utilizes a process that differs from the first deletion determination process, the process can be implemented from a different point of view.

For example, the deletion determination process based on the coverage ratio may be performed as the second deletion determination process. An image summarization process that ensures the coverage of an area can be implemented by the deletion determination process based on the coverage ratio. In this case, however, an area that is difficult to observe may occur (see FIG. 26). Specifically, an image that should not be deleted may be deleted by the second deletion determination process that utilizes the coverage ratio. However, it is possible to recover such an image by performing the first deletion determination process using the results of the second deletion determination process, and implement a more appropriate image summarization process.

A system configuration example of an image processing device will be described first, and the flow of the process will then be described using a flowchart. Note that the second deletion determination process is implemented using a method among the methods described above in connection with the first to third embodiments, and detailed description thereof is omitted.

6.1 System Configuration Example

Figure 28:
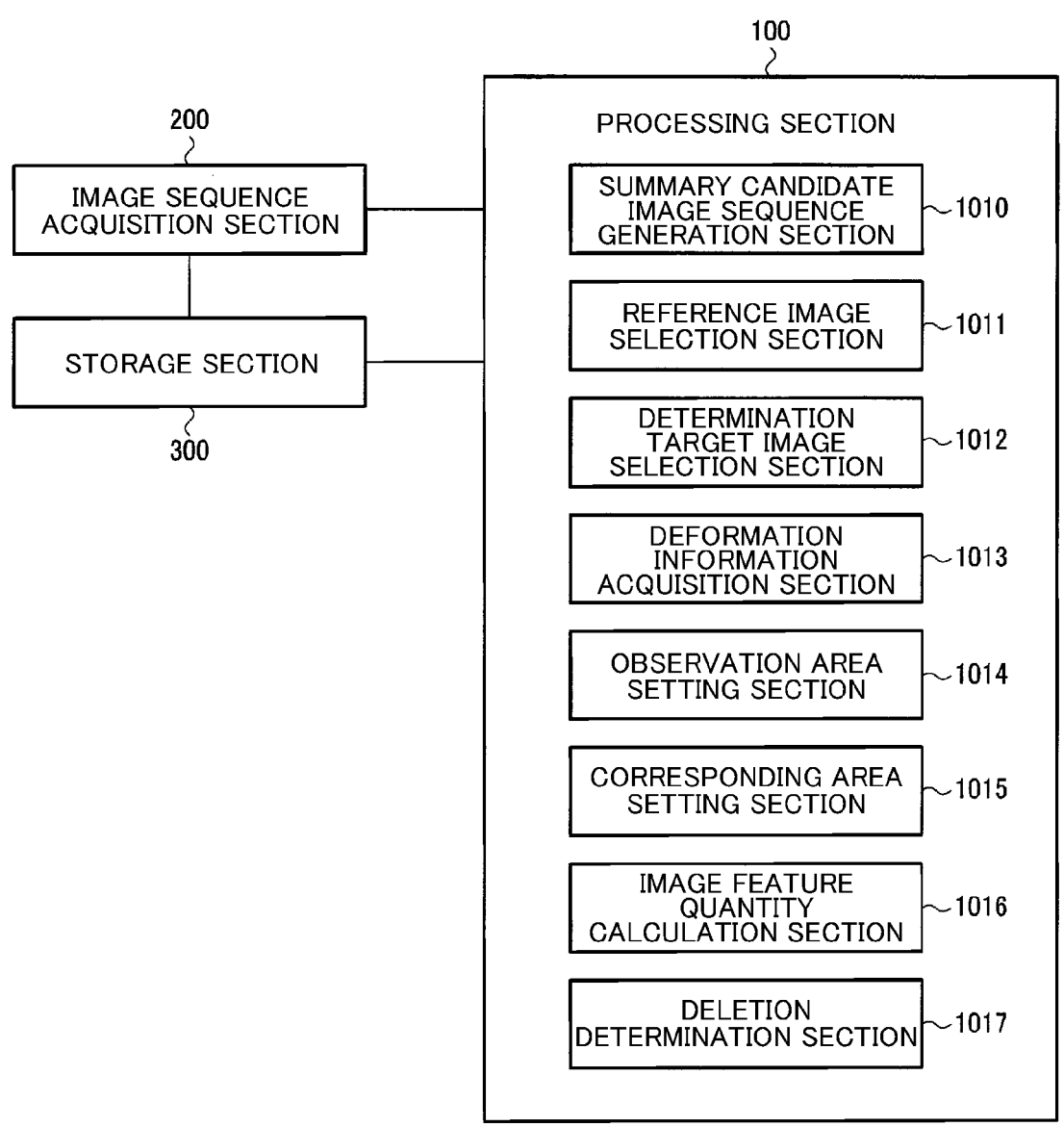
FIG. 28 illustrates a configuration example of an image processing device according to a fifth embodiment.

FIG. 28 illustrates a system configuration example of the image processing device according to the fifth embodiment. In FIG. 28, the partial image sequence setting section 1018 (see FIG. 22) is omitted from the processing section 100, and the processing section 100 further includes a summary candidate image sequence generation section 1010. Note that detailed description of the same configuration as that described above in connection with the fourth embodiment is omitted.

The summary candidate image sequence generation section 1010 performs the second deletion determination process on the image sequence acquired by the image sequence acquisition section 200 to generate the summary candidate image sequence that includes the summary images (i.e., images that are allowed to remain in the summary image sequence). The summary candidate image sequence generation section 1010 may set the deletion candidate image sequence that includes the deletion candidate images (i.e., images that are included in the image sequence acquired by the image sequence acquisition section 200, and are not allowed to remain in the summary candidate image sequence).

The determination target image selection section 1012 according to the fifth embodiment selects the determination target image from the images included in the deletion candidate image sequence. The reference image selection section 1011 selects the reference image from the images included in the summary candidate image sequence corresponding to the position of the determination target image selected by the determination target image selection section 1012 within the image sequence (i.e., the image sequence acquired by the image sequence acquisition section 200). The details of the process performed by the reference image selection section 1011 and the process performed by the determination target image selection section 1012 are described later.

As described above, the image that is allowed to remain in the summary image sequence (or a candidate for the image that is allowed to remain in the summary image sequence) is selected as the reference image, and the image that is subjected to the deletion determination process based on the reference image is selected as the determination target image. Specifically, when using the coverage ratio during the second deletion determination process, the reference image and the determination target image are set during the second deletion determination process, and the reference image and the determination target image are also set during the first deletion determination process (i.e., the process that utilizes the observation area). Note that the reference image and the determination target image that are set during the first deletion determination process may respectively be referred to as "first image" and "second image" when it is unclear whether the reference image and the determination target image are set during the first deletion determination process or the second deletion determination process.

6.2 Flow of Process

Figure 29:
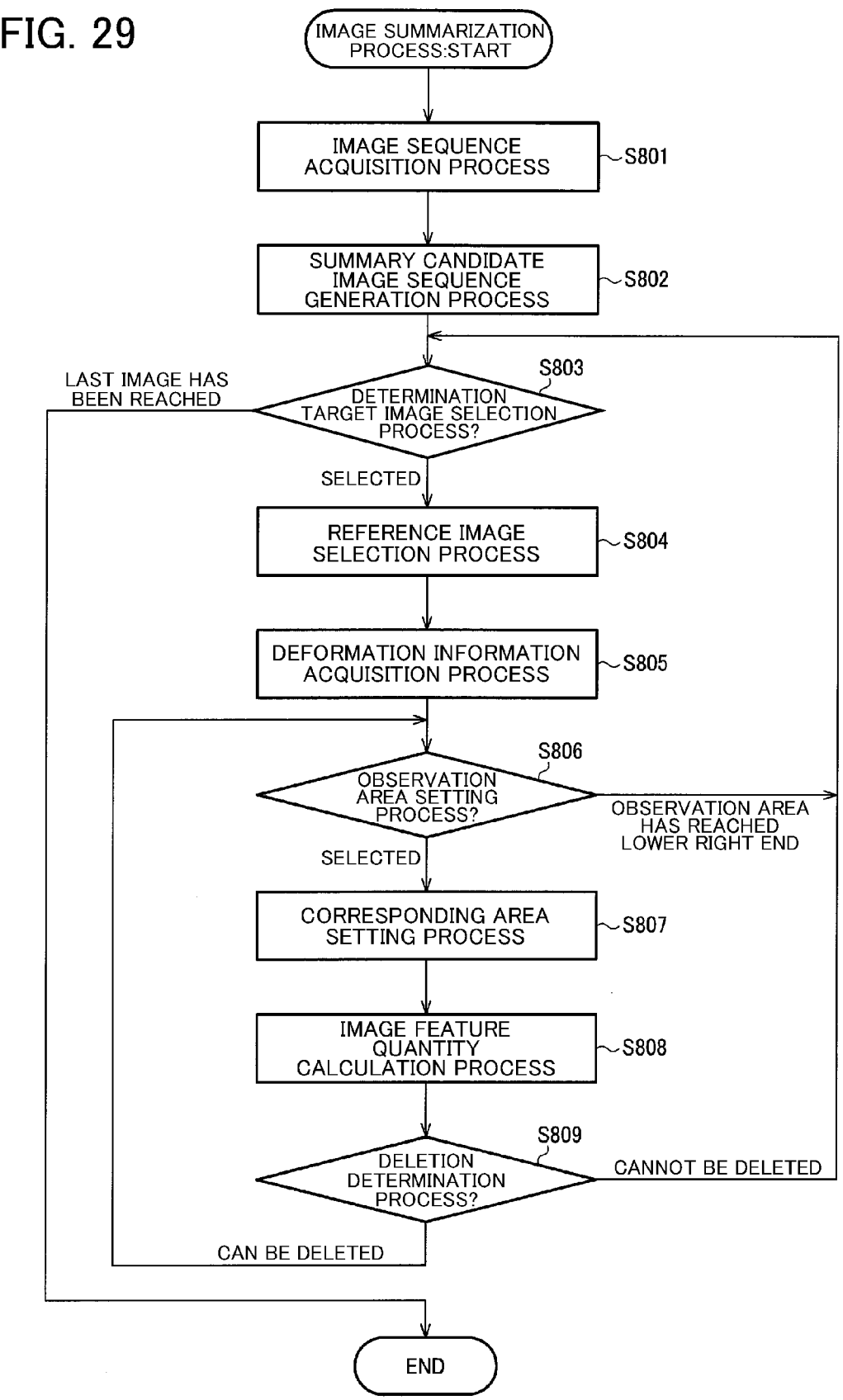
FIG. 29 is a flowchart illustrating an image summarization process according to the fifth embodiment.

The flow of the image summarization process according to the fifth embodiment is described below with reference to FIG. 29 (flowchart). When the image summarization process has started, the image sequence that is subjected to the image summarization process is acquired (S801). The image sequence acquired in the step S801 may be referred to as "acquired image sequence" in order to clearly distinguish the image sequence acquired in the step S801 from another image sequence.

The second deletion determination process is performed on the acquired image sequence to set the summary candidate image sequence and the deletion candidate image sequence (S802). A specific example of the second deletion determination process performed in the step S802 is described later. For example, when it has been determined that the third and eighth images among twelve images included in the acquired image sequence cannot be deleted, and the remaining images can be deleted (see FIG. 30), the summary candidate image sequence includes the third and eighth images, and the deletion candidate image sequence includes the remaining ten images. The deletion determination process may be performed a plurality of times on a single image depending on the second deletion determination process. Note that the deletion determination results refer to the final results when the second deletion determination process has completed, and it is not necessarily immediately determined that an image is the deletion candidate image or the summary image when it has been determined that the image can be deleted or cannot be deleted only once.

After completion of the second deletion determination process, the determination target image is selected (S803). For example, the determination target image is selected sequentially from the first image of the deletion candidate image sequence. Therefore, the first image of the deletion candidate image sequence is selected when the process in the step S803 is performed for the first time. The determination target image is updated (i.e., the image included in the deletion candidate image sequence that immediately follows the current determination target image is selected) during the subsequent process in the step S803.

When the determination target image has been selected, the reference image is selected from the summary candidate image sequence corresponding to the position of the determination target image within the acquired image sequence (S804). For example, the summary image included in the acquired image sequence that precedes and is situated closest to the determination target image is selected as the first image, and the summary image included in the acquired image sequence that follows and is situated closest to the determination target image, is selected as the second image. When no summary image precedes or follows the determination target image, the corresponding reference image is not selected.

Figure 30:
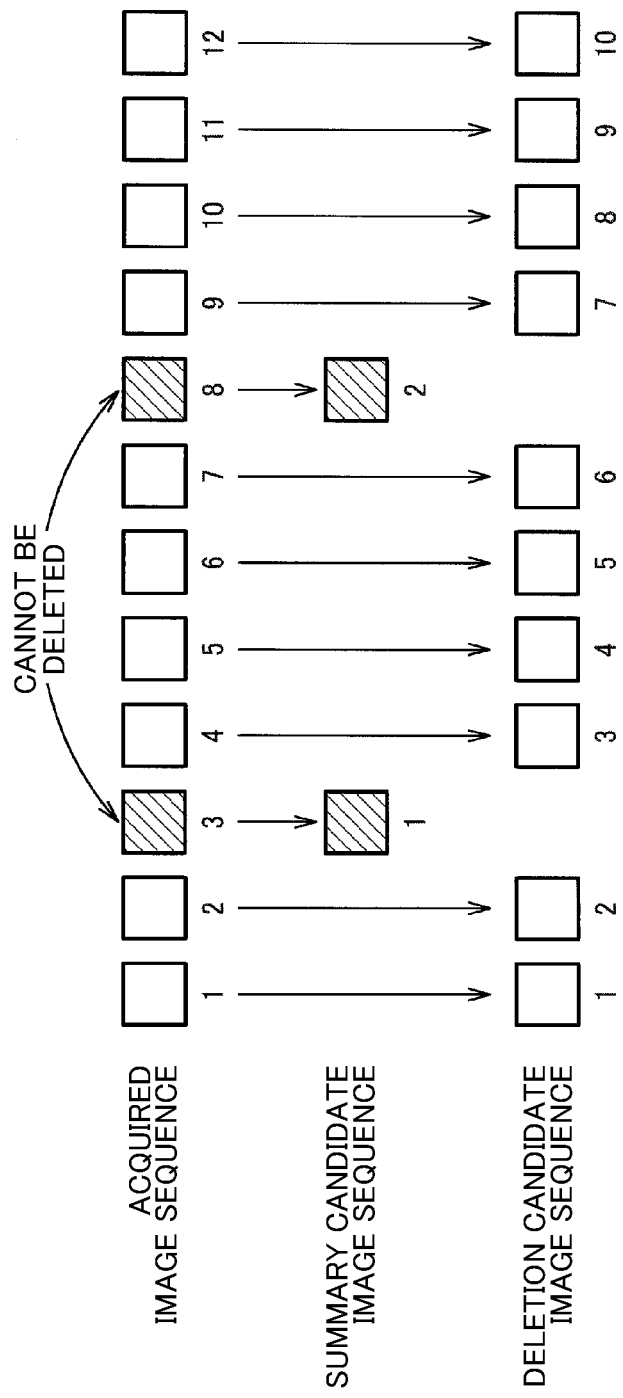
FIG. 30 is a view illustrating a summary candidate image sequence generation process.

In the example illustrated in FIG. 30, when the first image of the deletion candidate image sequence has been selected as the determination target image, the first reference image is not selected since no summary image precedes the determination target image in the acquired image sequence. The third image (i.e., the first image of the summary candidate image sequence) among the third and eighth images (summary images) of the acquired image sequence that follows the determination target image and is situated closest to the determination target image is selected as the second image.

In the example illustrated in FIG. 30, when the third to sixth images of the deletion candidate image sequence are selected as the determination target image, the first image of the summary candidate image sequence is selected as the first reference image, and the second image of the summary candidate image sequence is selected as the second reference image. When the seventh to tenth images of the deletion candidate image sequence are selected as the determination target image, the second image of the summary candidate image sequence is selected as the first reference image, and the second reference image is not selected.

The deformation information acquisition process (S805), the observation area selection process (S806), the corresponding area selection process (S807), the image feature quantity calculation process (S808), and the deletion determination process (S809) after the reference image and the determination target image have been selected are performed in the same manner as in the steps S704 to S708 illustrated in FIG. 23, respectively, and detailed description thereof is omitted.

When two reference images have been selected, the first deletion determination process using the first reference image and the determination target image, and the first deletion determination process using the second reference image and the determination target image are performed, and it is determined that the determination target image cannot be deleted (i.e., is allowed to remain in the summary image sequence) when it has been determined by each first deletion determination process that the determination target image cannot be deleted. Specifically, even when the corresponding area within one reference image is not suitable for observation, it is not advantageous to allow the determination target image to remain in the summary image sequence when the corresponding area within the other reference image in which the same object is captured is suitable for observation.

In the fifth embodiment, since the images that are allowed to remain have been provisionally searched during the second deletion determination process, the partial image sequence setting process (S709 in FIG. 23) (see the fourth embodiment) is unnecessary.

According to the fifth embodiment, the processing section 100 sets the summary candidate image sequence that includes the summary images that have been determined to be allowed to remain based on the coverage ratio, and the deletion candidate image sequence that includes the deletion candidate images that have been determined to be deleted based on the coverage ratio. The processing section 100 selects the first image from the summary candidate image sequence, selects the second image from the deletion candidate image sequence, sets the observation area within the second image, calculates the corresponding area that is an area within the first image that corresponds to the observation area based on the deformation information about the first image and the second image, and determines whether or not the second image can be deleted based on at least one of the first feature quantity calculated from the corresponding area and the second feature quantity calculated from the observation area.

The first image is the reference image that is set during the first deletion determination process, and the second image is the determination target image that is set during the first deletion determination process.

This makes it possible to perform the process that sets the summary candidate image sequence and the deletion candidate image sequence from the image sequence (acquired image sequence) (see FIG. 30) as preprocessing for the deletion determination process (first deletion determination process) that utilizes the first feature quantity and the second feature quantity. It is determined that the summary image is allowed to remain in the summary image sequence by selecting the reference image from the summary candidate image sequence, and selecting the determination target image from the deletion candidate image sequence, and it is possible to finally determine whether to delete the deletion candidate image or allow the deletion candidate image to remain in the summary candidate image sequence. Therefore, the accuracy of the process that sets the summary candidate image sequence and the deletion candidate image sequence may be low to some extent. For example, each image among the plurality of images included in the acquired image sequence that cannot be clearly determined to be the summary image may be determined to be the deletion candidate image. Since a high-accuracy determination is then made by performing the first deletion determination process, each deletion candidate image may be allowed to remain in the summary image sequence. Since it is considered that the image that has been determined to be the summary image is allowed to remain in the summary image sequence, it is desirable that the process that sets the summary candidate image sequence and the deletion candidate image sequence be performed based on a standard (instead of being performed randomly) taking account of the final results of the image summarization process (e.g., the effect of reducing the number of images) and the like.

7. Sixth Embodiment

A method that sets the partial image sequence using a scene change is described below.

7.1 System Configuration Example

Figure 31:
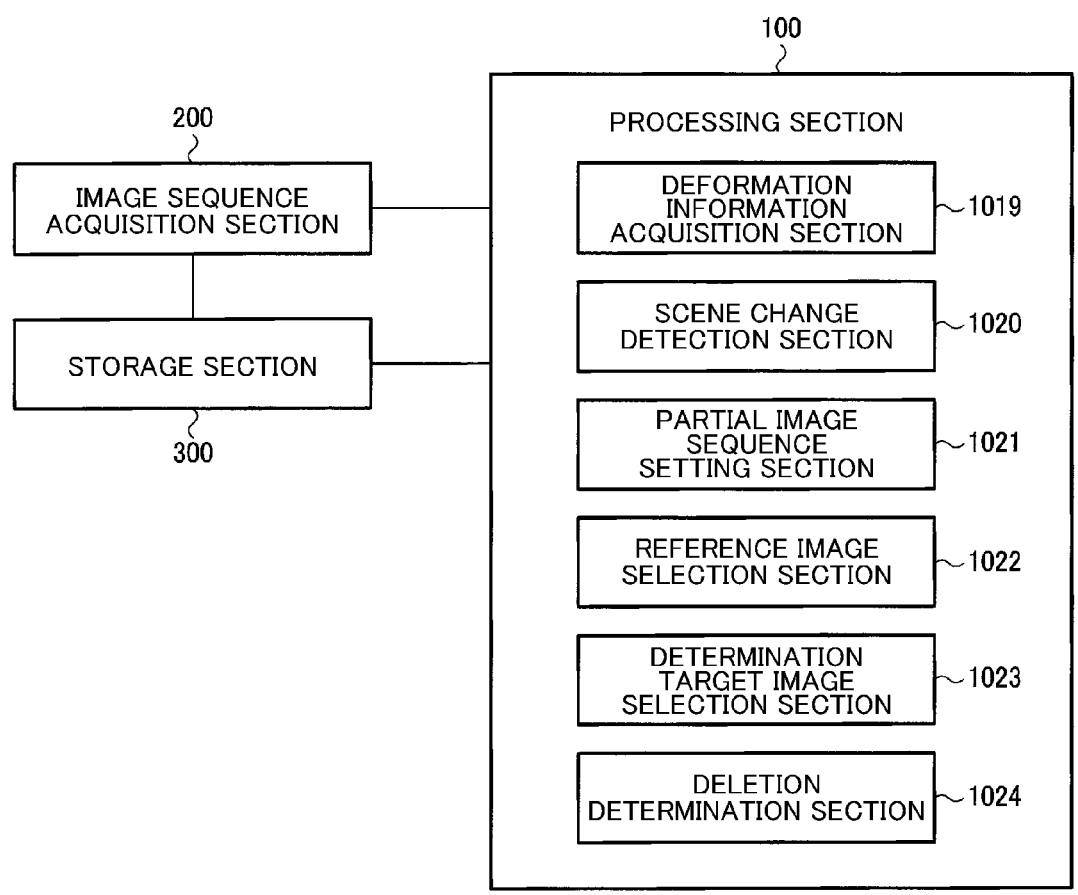
FIG. 31 illustrates a configuration example of an image processing device according to a sixth embodiment.

FIG. 31 illustrates a system configuration example of an image processing device according to the sixth embodiment. The image processing device includes a processing section 100, an image sequence acquisition section 200, and a storage section 300.

As illustrated in FIG. 31, the processing section 100 may include a deformation information acquisition section 1019, a scene change detection section 1020, a partial image sequence setting section 1021, a reference image selection section 1022, a determination target image selection section 1023, and a deletion determination section 1024.

The deformation information acquisition section 1019 acquires the deformation information about two images. The scene change detection section 1020 detects a scene change from the acquired image sequence. A specific method is described later.

The partial image sequence setting section 1021 sets part of the image sequence to be the partial image sequence based on the scene change detected by the scene change detection section 1020. Specifically, the position of the scene change may be used as the starting point or the end point of the partial image sequence. For example, when three scene changes A1 to A3 have been detected from the image sequence (see FIG. 32A), a partial image sequence B1 from the first image of the image sequence to the scene change A1, a partial image sequence B2 from the scene change A1 to the scene change A2, a partial image sequence B3 from the scene change A2 to the scene change A3, and a partial image sequence B4 from the scene change A3 to the final image of the image sequence, may be set. More specifically, when each scene change is set between adjacent images (see FIG. 32B), the starting point and the end point of each partial image sequence correspond to the image that immediately precedes or follows the scene change. In the example illustrated in FIG. 32B, the partial image sequence B1 corresponds to the series of images from the first image of the image sequence to the image that immediately precedes the scene change A1, and the partial image sequence B2 corresponds to the series of images from the image that immediately follows the scene change A1 to the image that immediately precedes the scene change A2. When a plurality of partial image sequences are set, the process performed by each section is respectively performed on each partial image sequence.

The reference image selection section 1022 selects the reference image from a plurality of images included in the partial image sequence. The determination target image selection section 1023 selects an image among the plurality of images included in the partial image sequence that differs from the reference image as the determination target image.

The deletion determination section 1024 determines whether or not the determination target image can be deleted based on the deformation information about the reference image and the determination target image. In the sixth embodiment, the deletion determination section 1024 determines whether or not the determination target image can be deleted based on the coverage ratio that represents the degree by which the determination target image is covered by the reference image.

Figure 33:
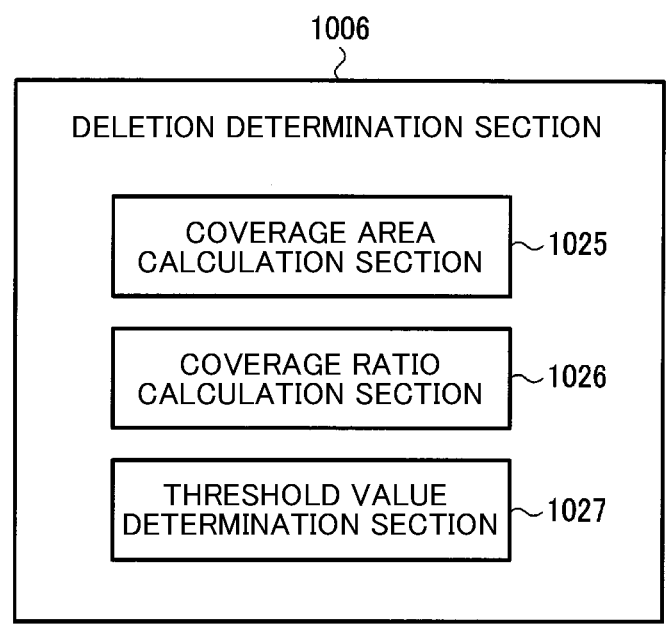
FIG. 33 illustrates a configuration example of a deletion determination section.

As illustrated in FIG. 33, the deletion determination section 1024 may include a coverage area calculation section 1025, a coverage ratio calculation section 1026, and a threshold value determination section 1027. Note that the configuration of the deletion determination section 1024 is not limited to the configuration illustrated in FIG. 33. Various modifications may be made, such as omitting some of the elements illustrated in FIG. 33, or adding other elements.

The coverage area calculation section 1025 projects one of two images onto the other image by utilizing the deformation information (deformation parameter) about the two images to calculate the coverage area. The coverage ratio calculation section 1026 calculates the coverage ratio based on the coverage area. The threshold value determination section 1027 compares the calculated coverage ratio with a given threshold value.

7.2 Flow of Process

The flow of the image summarization process according to the sixth embodiment is described below with reference to FIG. 34 (flowchart). When the image summarization process has started, the image sequence acquisition section 200 acquires the image sequence that is subjected to the image summarization process (S1001).

Figure 35A:
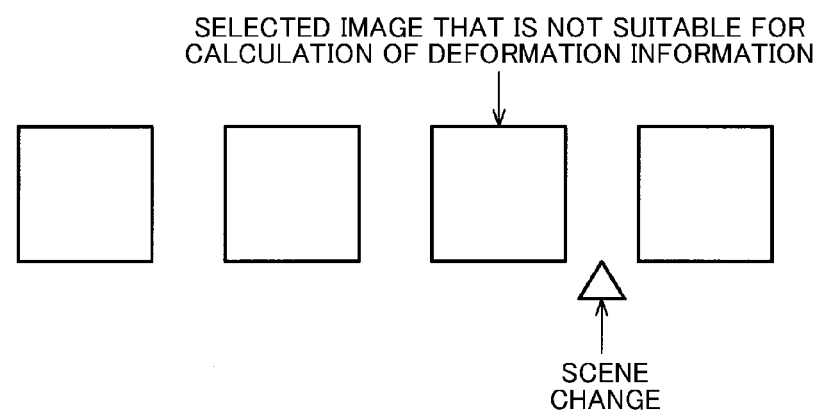
FIGS. 35A and 35B are views illustrating the relationship between the position of a selected image within an image sequence and the position of a detected scene change.
Figure 35B:
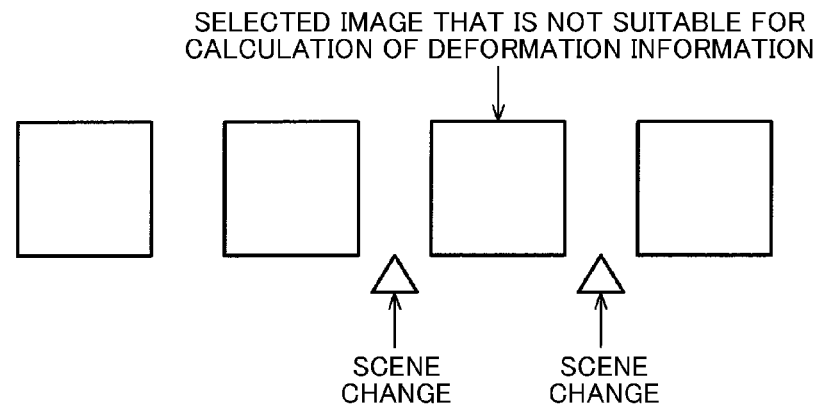

A scene change is detected from the acquired image sequence (S1002). Specifically, whether or not each image included in the image sequence is suitable for calculation of the deformation information is determined, and it is determined that a scene change occurred at a position corresponding to an image that has been determined not to be suitable for calculation of the deformation information. For example, when an image selected from the image sequence is not suitable for calculation of the deformation information (see FIG. 35A), it may be determined that a scene change occurred between the selected image and the image that immediately follows the selected image. In this case, the selected image is the end point of the partial image sequence, and the image that immediately follows the selected image is the starting point of the next partial image sequence. It may be determined that a scene change occurred at positions that precede or follow the selected image (see FIG. 35B).

Figure 36:
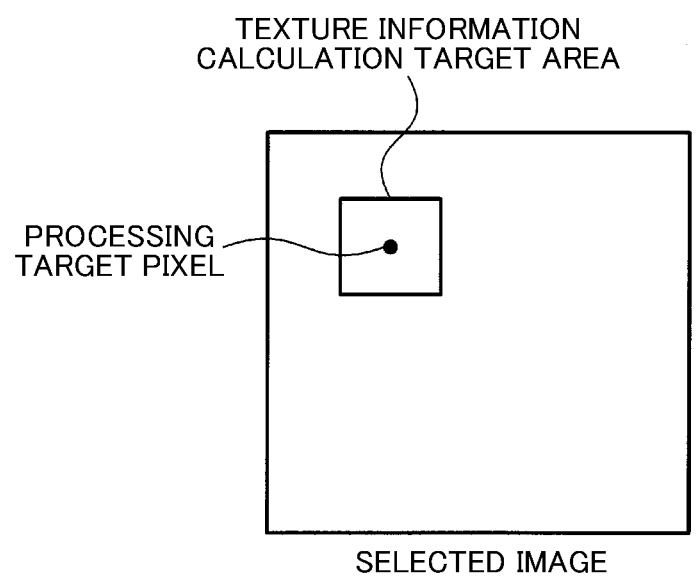
FIG. 36 illustrates a texture information calculation target area setting example.

Whether or not the selected image is suitable for calculation of the deformation information may be determined by determining whether or not each pixel of the selected image is suitable for calculation of the deformation information, and calculating the ratio of the pixels that have been determined to not be suitable for calculation of the deformation information to the pixels that have been determined to be suitable for calculation of the deformation information. For example, when a given area that includes the processing target pixel (determination target pixel) has a small amount of texture, it is difficult to distinguish the processing target pixel and its peripheral pixel (see FIG. 36). Therefore, even if the selected image has been selected as the reference image, and an area having similar properties has been found within the determination target image, it is difficult to determine the pixel of the determination target image that corresponds to the processing target pixel, and calculate accurate deformation information. For example, texture information (e.g., edge quantity) about the given area that includes the processing target pixel is calculated, and it is determined that the processing target pixel is suitable for calculation of the deformation information when a value represented by the texture information is larger than a given threshold value.

Each image included in the image sequence may be sequentially selected as the selected image, the ratio of the number of pixels suitable for calculation of the deformation information to the total number of pixels may be calculated for the selected image, it may be determined that the selected image is suitable for calculation of the deformation information (i.e., no scene change occurred at a position corresponding to the selected image) when the calculated ratio is larger than a given threshold value, and it may be determined that the selected image is not suitable for calculation of the deformation information (i.e., a scene change occurred at a position corresponding to the selected image) when the calculated ratio is equal to or smaller than the given threshold value.

Figure 32A:
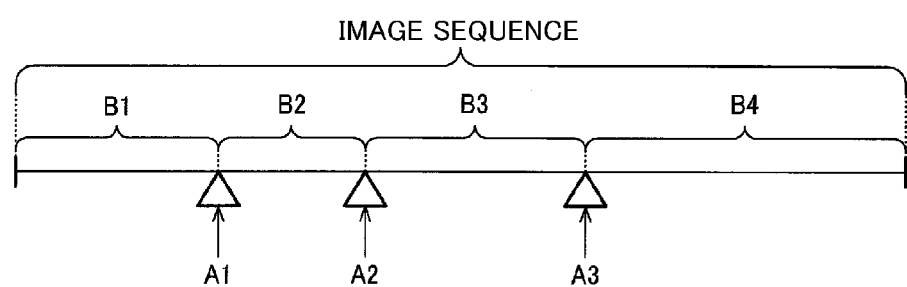
FIGS. 32A to 32B are views illustrating the relationship between a scene change and a partial image sequence.
Figure 32B:
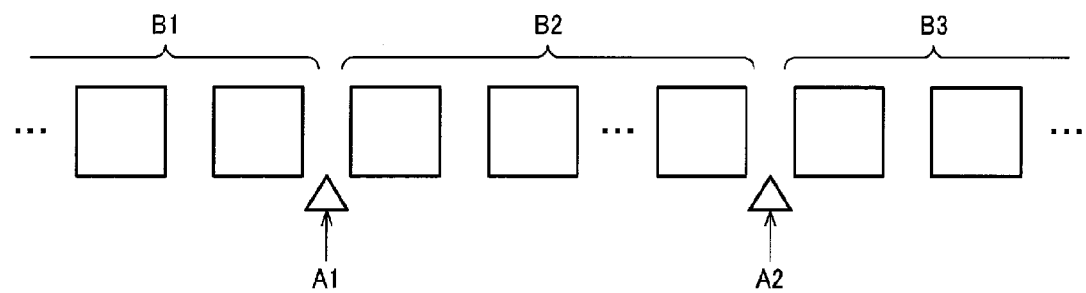

When a scene change has been detected, the partial image sequence is set based on the detected scene change (S1003). As illustrated in FIGS. 32A and 32B, the starting point and the end point of the partial image sequence may be set corresponding to the position of the detected scene change.

In the step S1003, the images included in the set partial image sequence that have not been subjected to the image summarization process are selected. The reference image selection section 1022 selects the first image of the selected partial image sequence as the reference image (S1004). When the subsequent process in the step S1004 is performed on a given partial image sequence (i.e., when the process in the step S1004 is performed after the process in the step S1007), the determination target image that has been determined to be allowed to remain in the deletion determination process in the step S1007 is selected as the next reference image. The selected reference image is allowed to remain in the summary image sequence. Note that the process on the partial image sequence is terminated when the reference image cannot be selected from the partial image sequence due to an error or the like, and the process in the step S1003 is performed again.

When the reference image has been selected, the determination target image selection section 1023 selects the determination target image from the images included in the partial image sequence (S1005). When the determination target image has not been set, the image that immediately follows the reference image (i.e., the second image of the partial image sequence when the process in the step S1005 is performed on a given partial image sequence for the first time) is selected as the determination target image. When the kth image of the partial image sequence has been selected as the determination target image, the (k+1)th image (i.e., the selection position is shifted by 1) of the input image sequence is selected as the next determination target image. When the deletion determination process has been performed on the last image of the partial image sequence, the determination target image cannot be selected in the step S1005. In this case, the image summarization process on the partial image sequence is terminated, and the step S1003 is performed again.

When the reference image and the determination target image have been selected, the deformation information about the reference image and the determination target image is calculated (S1006), and whether or not the determination target image can be deleted is determined based on the calculated deformation information (S1007). Specifically, the coverage area is calculated by utilizing the deformation information (deformation parameter) about two images, and the coverage ratio is calculated based on the coverage area.

When it has been determined that the determination target image can be deleted in the step S1007, the determination target image is updated (S1005). When it has been determined that the determination target image cannot be deleted (i.e., the determination target image cannot be covered by the reference image) in the step S1007, it is necessary to allow the determination target image to remain in the summary image sequence. Therefore, the determination target image that has been determined to be allowed to remain in the step S1007 is selected as the next reference image in the step S1004.

The image summarization process on one partial image sequence is completed by the processes in the steps S1004 to S1007. In this case, the image summarization process is performed on the next partial image sequence from the step S1003. When the image summarization process has been performed on each partial image sequence (i.e., when the partial image sequence cannot be selected in the step S1003), the process is terminated.

The flow of the image summarization process on each partial image sequence is the same as described above with reference to FIGS. 4A to 4D.

Figure 34:
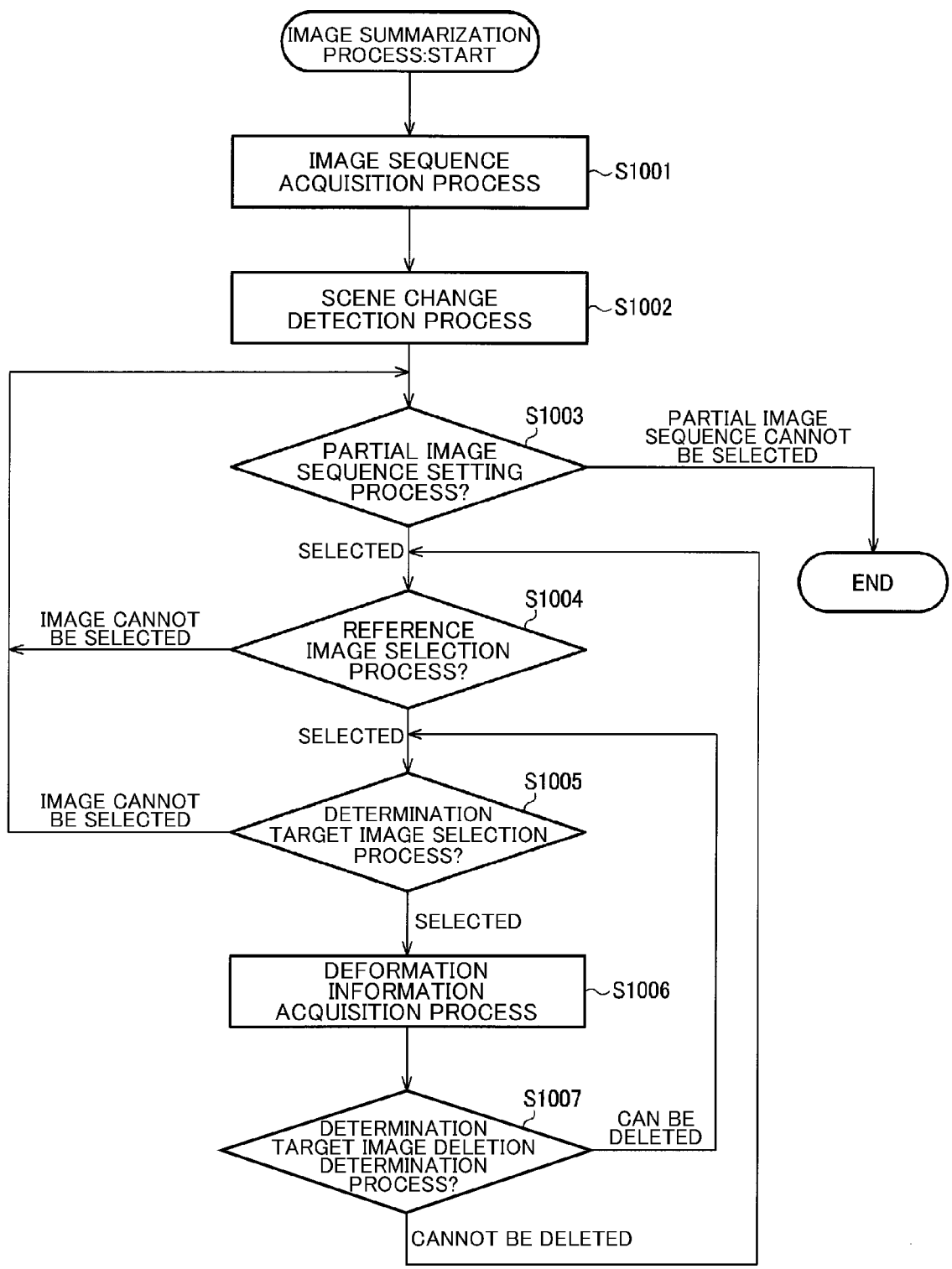
FIG. 34 is a flowchart illustrating an image summarization process according to a sixth embodiment.

Although FIG. 34 illustrates an example in which a plurality of partial image sequences that have been set based on a scene change are sequentially processed one by one, the configuration is not limited thereto. When the configuration of the processing section 100 is suitable for parallel processing (e.g., when a CPU that includes a plurality of cores is used as the processing section 100), or when the image processing device according to the sixth embodiment includes a plurality of computers, and distributed processing is performed by each computer, the deletion determination process (S1004 to S1007) may be performed on the plurality of partial image sequences in parallel. This makes it possible to reduce the time required for the deletion determination process, for example.

7.3 Modifications

Figure 39:
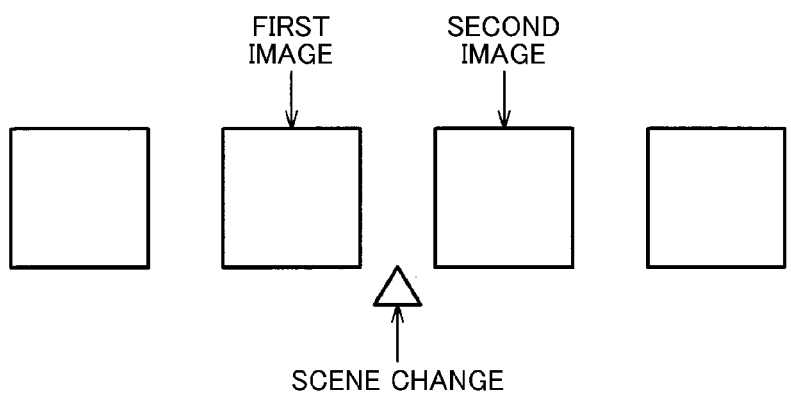
FIG. 39 is a view illustrating the relationship between the positions of a first image and a second image within an image sequence and the position of a detected scene change.

Various modifications may be made of the method according to the sixth embodiment. For example, the scene change detection method is not limited to the above method. For example, a scene change may be detected based on similarity information about two images (two adjacent images in a narrow sense) included in the image sequence acquired by the image sequence acquisition section 200. Since it is considered that the deformation information can be accurately estimated when the similarity between the images is high, the similarity information about the images can be used as information that represents the accuracy of the deformation information. In this case, NCC, or the reciprocal of SSD or SAD (degree of difference between images) may be used as the similarity information about the images. It is determined that a scene change occurred between two images when a value represented by the similarity information is smaller than a given threshold value. For example, when it has been determined that the similarity between a first image and a second image that is adjacent to the first image is low, it may be determined that a scene change occurred between the first image and the second image (see FIG. 39). It is desirable that two images for which the similarity information is calculated be adjacent to each other in the image sequence in order to uniquely determine the position of a scene change.

The reference image/determination target image selection method employed in the steps S1004 and S1005 in FIG. 34 is not limited to the above method.

According to the sixth embodiment, the image processing device includes the image sequence acquisition section 200 that acquires an image sequence that includes a plurality of images, and the processing section 100 that performs the image summarization process that deletes some of the plurality of images included in the image sequence acquired by the image sequence acquisition section 200 to acquire a summary image sequence (see FIG. 31). The processing section 100 detects a scene change from the image sequence, and sets the partial image sequence that includes images among the plurality of images included in the image sequence based on the detected scene change. The processing section 100 selects the reference image and the determination target image from the partial image sequence, and determines whether or not the determination target image can be deleted based on the deformation information about the reference image and the determination target image.

The term "scene change" refers to a change in scene corresponding to the captured image. A scene change is widely used in the field of a movie division technique (e.g., insertion of chapter information) and the like. A scene change used in connection with a known method may be used directly as the scene change according to the sixth embodiment. In this case, the processing section 100 may detect a scene change based on one of motion information calculated from a plurality of images, imaging information about a specific object, and brightness information.

The motion information represents a change in position of the object between two images (between two adjacent images in a narrow sense). For example, the motion information may be the motion vector. The motion vector may be calculated using various methods. The motion vector may be simply calculated by performing a block matching process on a given area (block) within one image and the other image. Specifically, information that represents the relative positional relationship between the position of the given area within the image and the position of the matched area within the image is the motion vector. When using the motion vector, it may be determined that a scene change occurred between two images used to calculate the motion vector when the motion vector is large (e.g., the motion vector is compared with a given threshold value).

The imaging information about a specific object is information that represents whether or not a characteristic object is captured. The object may be detected from the image using various methods. For example, information about the target specific object may be stored as a template, and a template matching process may be performed on each image. In this case, a change from a state in which the specific object is captured to a state in which the specific object is not captured, or a change from a state in which the specific object is not captured to a state in which the specific object is captured, is detected as a scene change.

A scene change may be detected using the brightness information. For example, when using an RGB channel image, the maximum value among the R value, the G value, and the B value of each pixel may be calculated as the brightness value, and the average value of the brightness values of all of the pixels included in the image may be used as the brightness information about the image. When using the brightness information, it may be determined that a scene change occurred between images when the brightness information about a given image of the image sequence differs to a large extent from the brightness information about the image that follows the given image (e.g., when the difference in brightness information is equal to or larger than a threshold value). When the imaging device includes a flash mechanism or the like, the brightness information may change to a large extent by operating the mechanism even if the object or the like has not changed. Therefore, it may be desirable to use information other than the brightness information for detecting a scene change, or use the brightness information and information other than the brightness information in combination depending on the configuration of the imaging device, for example.

Note that a scene change need not necessarily be detected based on the motion information, the imaging information about a specific object, the brightness information, or the like. A scene change may be detected using various methods (e.g., chroma information (e.g., the degree of redness when the image is an in vivo image)).

The above information for detecting a scene change may be used either alone or in combination. For example, when using the motion information and the brightness information in combination, a determination may be made based on whether or not a motion between images represented by the motion information is large, and whether or not a change in brightness represented by the brightness information is large. In this case, a scene change may be detected when the motion and a change in brightness are large, or may be detected when at least one of the motion and a change in brightness is large, for example.

The above configuration makes it possible to divide the image sequence into a plurality of partial image sequences based on a scene change detected from the image sequence, and perform the deletion determination process that utilizes the deformation information on each partial image sequence. Since it is likely that the image that precedes the scene change and the image that follows the scene change differ in the imaging target and the like, it is normally unnecessary to use such images for the deletion determination process that utilizes the deformation information. Since the accuracy of the deletion determination process may decrease as a result of calculating the deformation information about images that differ to a large extent, it may be undesirable to perform the process on the image that precedes the scene change and the image that follows the scene change. An efficient image summarization process can be implemented by setting the partial image sequence based on a scene change.

Note that the expression "precedes or follows the image" or "precedes or follows the scene change" refers to the position within the image sequence. Since it is considered that the image sequence is a set of temporally or spatially continuous images, the position within the image sequence can be defined based on the continuity. For example, an image acquired at an earlier time precedes an image acquired at a later time.

The processing section 100 may detect a scene change based on accuracy information that represents the accuracy of the deformation information used to determine whether or not the determination target image can be deleted. Specifically, the processing section 100 may determine that a scene change has been detected when a value represented by the accuracy information is smaller than a given accuracy threshold value.

The accuracy information that represents the accuracy of the deformation information is calculated corresponding to each image or each combination of two images included in the image sequence. When the accuracy represented by the accuracy information calculated from one image is low, the deformation information does not appropriately represent deformation between two images when the deformation information is calculated using the image and another image included in the image sequence. Therefore, when calculating the accuracy information, the corresponding deformation information need not necessarily be calculated in advance. The accuracy information may be calculated in advance, and whether or not to calculate the corresponding deformation information may be determined based on the accuracy information. When the accuracy represented by the accuracy information calculated from a combination of two images is low, the deformation information does not appropriately represent deformation between the two images when the deformation information is calculated using the two images.

Figure 37A:
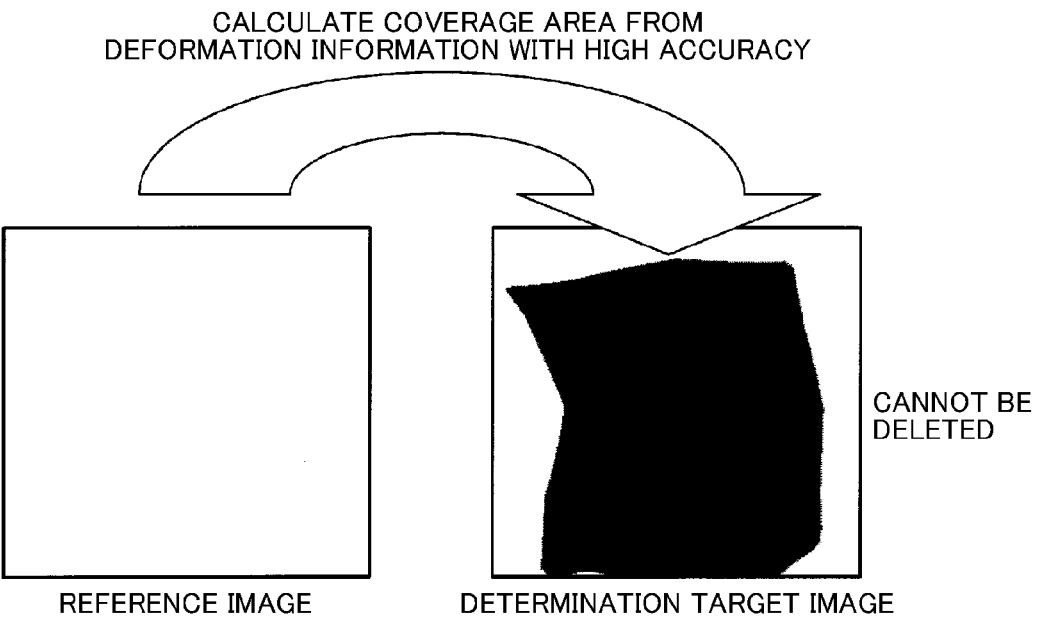
FIGS. 37A and 37B are views illustrating the difference in shape of a coverage area due to the difference in accuracy of deformation information.
Figure 37B:
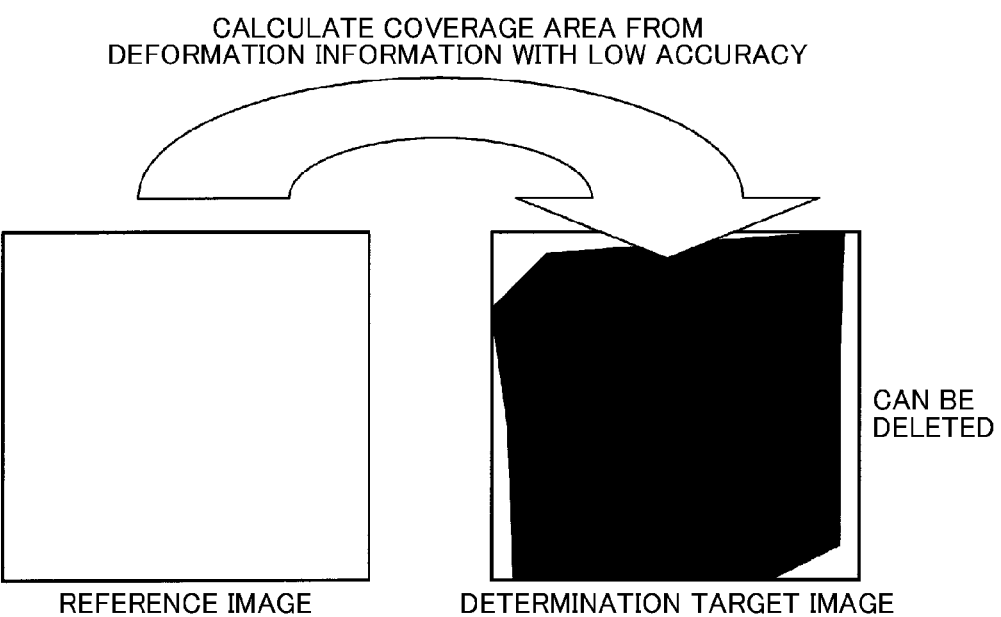

This makes it possible to detect a scene change based on the accuracy information that represents the accuracy of the deformation information. As illustrated in FIGS. 37A and 37B, when the accuracy of the deformation information is low, it is difficult to sufficiently achieve the advantages of the process that utilizes the deformation information (i.e., preventing the occurrence of an area that cannot be observed, or preventing a situation in which the attention area is missed). However, the accuracy of the deletion determination process can be improved by detecting a scene change based on the accuracy information. An improvement in accuracy can also be achieved by utilizing the accuracy information independently of detection of a scene change. In this case, however, it is necessary to perform an additional process in order to detect a scene change. Therefore, the accuracy of the deletion determination process, and the efficiency and the speed of the image summarization process can be improved using a simple process by utilizing the accuracy information for detecting a scene change.

The processing section 100 may determine whether or not each pixel included in a selected image among the plurality of images is suitable for calculation of the deformation information, calculate the accuracy information based on the number of pixels that have been determined to be suitable for calculation of the deformation information, and detect a scene change at a position corresponding to the selected image within the image sequence based on the calculated accuracy information.

Figure 38:
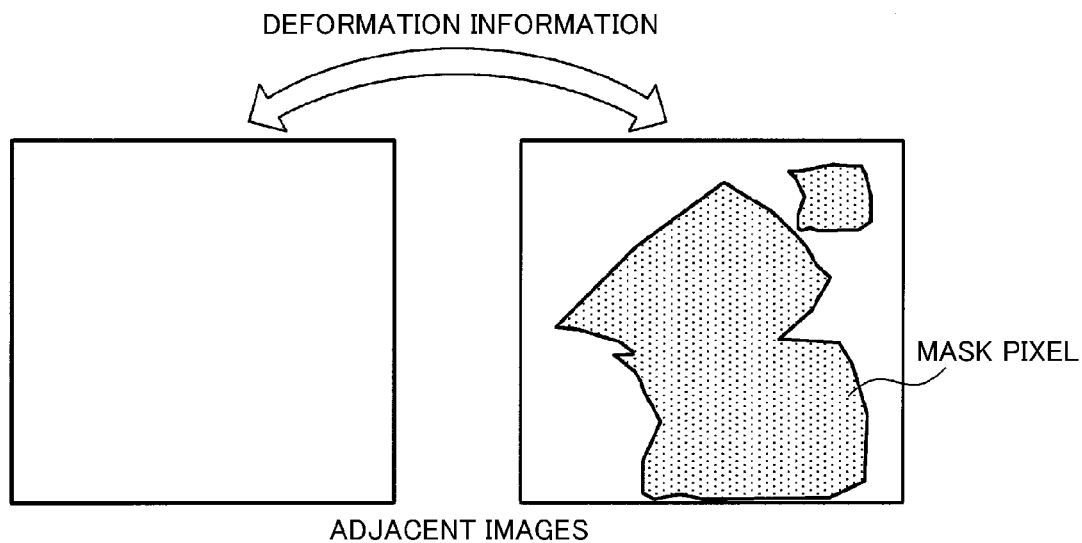
FIG. 38 illustrates an example of an accuracy information calculation method.

According to this configuration, when a given image has been selected from the image sequence as the selected image, the accuracy information about the selected image can be calculated based on the determination result for each pixel of the selected image. The deformation information may be configured in various ways, and the deletion determination process that utilizes the deformation information (deformation process in a narrow sense) may be implemented in various ways. The deformation information and the deletion determination process that utilizes the deformation information are based on the fact that a given pixel within one image corresponds to a pixel within the other image. Specifically, it is natural to determine the accuracy of the deformation information based on information on a pixel basis. In the sixth embodiment, whether or not each pixel included in the selected image is suitable for calculation of the deformation information is determined, and the accuracy information is calculated from the determination results. For example, the ratio of the number of pixels (number of mask pixels) that are suitable for calculation of the deformation information to the total number of pixels of the selected image may be used as the accuracy information (see FIG. 38).

When it has been determined that the accuracy of the deformation information corresponding to the selected image is low based on the accuracy information calculated from the selected image, it is determined that a scene change has been detected at the position of the selected image within the image sequence. For example, it may determined that a scene change occurred between the selected image and the image that immediately follows the selected image (see FIG. 35A). Since it is considered that the accuracy of the deformation information about the selected image and the image that immediately precedes the selected image is also low, it may determined that a scene change has been detected between the selected image and the image that immediately follows the selected image, and between the selected image and the image that immediately precedes the selected image (see FIG. 35B).

The processing section 100 may set an area that has a given size and includes the processing target pixel that is subjected to the determination as to suitability for calculation of the deformation information within the selected image, and determine whether or not the processing target pixel is suitable for calculation of the deformation information based on texture information about the set area.

The term "texture" refers to the pattern of an image. For example, a two-dimensional Fourier transform or the like may be performed on the image to calculate the spatial frequency power spectrum, and the spatial frequency power spectrum may be used as the texture information. Note that it suffices that the texture information is information that represents the amount of pattern within the image. The texture information may include edge information that represents the contour of the object and the like.

This makes it possible to determine whether or not each pixel of the image is suitable for calculation of the deformation information based on the texture information. When a complex pattern is drawn, it is considered that the processing target pixel can be easily distinguished from its peripheral pixel. Therefore, when the deformation information about the selected image and another image is calculated, it is likely that the pixel included in the other image that corresponds to the processing target pixel is clear. When no pattern is present, it is difficult to distinguish the processing target pixel from other pixels, and link the processing target pixel with the pixel included in the other image.

Note that whether or not each pixel is suitable for calculation of the deformation information need not necessarily be determined using the texture information. For example, the method disclosed in JP-A-2007-257287 or the like may be used.

The processing section 100 may calculate similarity information about the similarity between a first image among the plurality of images included in the image sequence and a second image that immediately follows the first image as the accuracy information. The processing section 100 may detect a scene change at a position between the first image and the second image within the image sequence based on the calculated accuracy information.

This makes it possible to use the similarity information about the similarity between two images (adjacent images) as the accuracy information. Specifically, it is considered that the deformation information can be accurately calculated when the similarity between images is high. A known NCC or the like may be used as the similarity information. Alternatively, SSD or SAD that represents the degree of difference between images may be calculated, and the reciprocal thereof may be used as the similarity information. In this case, the position of the scene change may be the position between the first image and the second image (see FIG. 39).

When an ith (i is an integer) scene change and an (i+1)th scene change that immediately follows the ith scene change have been detected from the image sequence, the processing section 100 may set images among the plurality of images included in the image sequence that follow the ith scene change and precede the (i+1)th scene change to be the partial image sequence.

This makes it possible to set the partial image sequence based on the scene change (see FIG. 32B). Since the sixth embodiment is based on the assumption that a scene change is detected between images, for example, an image sequence that includes the image that immediately follows the ith scene change as the starting point, and includes the image that immediately precedes the (i+1)th scene change as the end point, is set to be the partial image sequence. When only one image is present between the ith scene change and the (i+1)th scene change, the image may be allowed to remain in the summary image sequence, or may be deleted (the image is desirably allowed to remain in the summary image sequence taking account of preventing occurrence of an area that cannot be observed), and need not be set to be the partial image sequence. Alternatively, the image may be set to be the partial image sequence, and may be processed. In this case, since the reference image is set in the step S1004, and the determination target image cannot be selected in the step S1005, the image is allowed to remain in the summary image sequence.

When a plurality of partial image sequences have been set, the processing section 100 may select the reference image and the determination target image from the plurality of partial image sequences in parallel, and determine whether or not the determination target image can be deleted based on the deformation information about the reference image and the determination target image.

Specifically, when a jth (j is an integer) scene change has been detected from the image sequence, the processing section 100 sets a kth (k is an integer) partial image sequence that includes images among the plurality of images included in the image sequence that precede the jth scene change, and a (k+1)th partial image sequence that includes images among the plurality of images included in the image sequence that follow the jth scene change. In this case, a process that selects the reference image and the determination target image from the kth partial image sequence, and determines whether or not the determination target image can be deleted based on the deformation information about the reference image and the determination target image, and a process that selects the reference image and the determination target image from the (k+1)th partial image sequence, and determines whether or not the determination target image can be deleted based on the deformation information about the reference image and the determination target image, may be performed in parallel.

According to this configuration, since the deletion determination process (S1004 to S1007 in FIG. 34) on each partial image sequence can be performed in parallel, the speed of the image summarization process can be increased.

The first to sixth embodiments according to the invention and the modifications thereof have been described above. Note that the invention is not limited to the first to sixth embodiments and the modifications thereof. Various modifications and variations may be made of the first to sixth embodiments and the modifications thereof without departing from the scope of the invention. A plurality of elements described in connection with the first to sixth embodiments and the modifications thereof may be appropriately combined to implement various configurations. For example, some elements may be omitted from the elements described in connection with the first to sixth embodiments and the modifications thereof. Some of the elements described above in connection with different embodiments and/or modifications may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. An image processing device comprising:
 a CPU which executes a program stored in a memory to perform:

image sequence acquisition processing that acquires an image sequence that includes a plurality of images; and image summarization processing that deletes some of the plurality of images included in the image sequence acquired by the image sequence acquisition processing to acquire a summary image sequence, wherein the image summarization processing selects a reference image and a determination target image from the plurality of images, calculates a coverage ratio of the determination target image by the reference image based on deformation information about the reference image and the determination target image, and determines whether or not the determination target image can be deleted based on the coverage ratio.

2. The image processing device as defined in claim 1, wherein:

first to Nth (N is an integer equal to or larger than 2) images are input as an input image sequence, the image summarization processing selects a pth (p is an integer that satisfies 1≤p≤N) image as a first reference image, selects a qth (q is an integer equal to or larger than p+2) image as a second reference image, and selects an rth (r is an integer that satisfies p+1≤r≤q−1) image as the determination target image, and the image summarization processing calculates the coverage ratio based on the deformation information about the first reference image and the determination target image and the deformation information about the second reference image and the determination target image, and determines whether or not the determination target image can be deleted based on the coverage ratio.

3. The image processing device as defined in claim 2, wherein:

the image summarization processing selects the second reference image from a second reference image selection interval in which a starting point and an end point are set corresponding to (p+2)th to Nth images, and determines whether or not the determination target image can be deleted based on the first reference image and the second reference image, and the image summarization processing selects an xth (x is an integer that satisfies x>q) image included in the second reference image selection interval as a next second reference image, and updates the starting point of the second reference image selection interval with the qth image when it has been determined that (p+1)th to (q−1)th images can be deleted.

4. The image processing device as defined in claim 3, wherein the image summarization processing sets the value x based on a value (q+j)/2 when a jth (j is an integer) image corresponds to the end point of the second reference image selection interval.

5. The image processing device as defined in claim 3, wherein the image summarization processing selects a yth (y is an integer that satisfies y<q) image included in the second reference image selection interval as a next second reference image, and updates the end point of the second reference image selection interval with the qth image when it has been determined that at least one image among the (p+1)th to (q−1)th images cannot be deleted.

6. The image processing device as defined in claim 5, wherein the image summarization processing sets the value y based on a value (i+q)/2 when an ith (i is an integer) image corresponds to the starting point of the second reference image selection interval.

7. The image processing device as defined in claim 3, wherein:

the image summarization processing performs a process that allows an image among the plurality of images that has been selected as the first reference image to remain in the summary image sequence when the starting point and the end point of the second reference image selection interval are adjacent to each other as a result of updating the starting point or the end point of the second reference image selection interval, and the image summarization processing sets an image sequence that includes an image among the plurality of images that corresponds to the starting point and images that follow the image among the plurality of images that corresponds to the starting point in the input image sequence, to be the input image sequence, and processes the set input image sequence after setting the value p to 1.

8. The image processing device as defined in claim 2, wherein the image summarization processing selects a (q+1)th image as the second reference image when it has been determined that (p+1)th to (q−1)th images can be deleted.

9. The image processing device as defined in claim 8, wherein the image summarization processing performs a process that allows an image among the plurality of images that has been selected as the first reference image to remain in the summary image sequence when it has been determined that at least one of the (p+1)th to (q−1)th images cannot be deleted, sets an image sequence that includes the (q−1)th to Nth images to be the input image sequence, and processes the set input image sequence after setting the value p to 1.

10. The image processing device as defined in claim 1, wherein:

first to Nth (N is an integer equal to or larger than 2) images are input as an input image sequence, and the image summarization processing selects the first image as the reference image, selects a kth (k is an integer that satisfies 2≤k≤N−1) image as the determination target image, calculates the coverage ratio based on the deformation information about the reference image and the determination target image, determines whether or not the determination target image can be deleted based on the coverage ratio, and selects a (k+1)th image as the determination target image when it has been determined that the kth image can be deleted.

11. The image processing device as defined in claim 10, wherein the image summarization processing performs a process that allows an image among the plurality of images that has been selected as the reference image to remain in the summary image sequence when it has been determined that the kth image cannot be deleted, sets an image sequence that includes the kth to Nth images to be the input image sequence, and processes the set input image sequence.

12. The image processing device as defined in claim 1, wherein:

first to Nth (N is an integer equal to or larger than 2) images are input as an input image sequence, and the image summarization processing selects an sth (s is an integer that satisfies 2≤s≤N−1) image as the reference image, selects a tth (t is an integer that satisfies 1≤t≤N and t≠s) image as the determination target image, calculates the coverage ratio based on the deformation information about the reference image and the determination target image, and determines whether or not the determination target image can be deleted based on the coverage ratio.

13. The image processing device as defined in claim 12, wherein the image summarization processing sets an image sequence that includes the first to (s−1)th images to be the input image sequence when it has been determined that at least one image among the first to (s−1)th images cannot be deleted, and processes the set input image sequence.

14. The image processing device as defined in claim 12, wherein the image summarization processing sets an image sequence that includes an (s+1)th to Nth images to be the input image sequence when it has been determined that at least one image among the (s+1)th to Nth images cannot be deleted, and processes the set input image sequence.

15. The image processing device as defined in claim 1, wherein the image summarization processing calculates the deformation information about adjacent images among the reference image, the determination target image, and the plurality of images that are situated between the reference image and the determination target image, and calculates the deformation information about the reference image and the determination target image based on the calculated deformation information about the adjacent images.

16. The image processing device as defined in claim 1, wherein the image summarization processing calculates a coverage area that is an area in which the determination target image is covered by the reference image based on the deformation information about the reference image and the determination target image, and calculates a ratio of the coverage area to the determination target image as the coverage ratio.

17. The image processing device as defined in claim 16, wherein the image summarization processing selects first to Mth (M is an integer equal to or larger than 2) reference images from the plurality of images as the reference image, calculates a uth ($1 \leq u \leq M$) coverage area based on the deformation information about a uth reference image and the determination target image, sets an area that corresponds to a sum-set of first to Mth coverage areas to be the coverage area, and calculates the coverage ratio based on the set coverage area.

18. The image processing device as defined in claim 16, wherein the image summarization processing sets a weighting coefficient corresponding to a position within the determination target image, and calculates the coverage ratio based on a ratio of a first weight sum to a second weight sum, the first weight sum being calculated based on the weighting coefficient and the coverage area, and the second weight sum being calculated based on the weighting coefficient and the determination target image.

19. The image processing device as defined in claim 1, wherein the image summarization processing sets a plurality of points to the determination target image, and calculates the coverage ratio based on a number of points included in the reference image when the plurality of points are converted corresponding to the deformation information about the reference image and the determination target image.

20. The image processing device as defined in claim 19, wherein the image summarization processing sets first to Mth (M is an integer equal to or larger than 2) reference images from the plurality of images as the reference image, calculates a number of points included in a uth ($1 \leq u \leq M$) reference image as uth coverage information when the plurality of points are converted corresponding to the deformation information about the uth reference image and the determination target image, and calculates the coverage ratio based on first coverage information to Mth coverage information respectively calculated from the first to Mth reference images.

21. The image processing device as defined in claim 19, wherein the image summarization processing sets a weighting coefficient corresponding to a position within the determination target image, and calculates the coverage ratio based on the weighting coefficient and a point included in the reference image when the plurality of points are converted corresponding to the deformation information about the reference image and the determination target image.

22. The image processing device as defined in claim 18, wherein the image summarization processing sets 0 to a first area of the determination target image as the weighting coefficient, and sets 1 to a second area of the determination target image as the weighting coefficient, the second area differing from the first area.

23. The image processing device as defined in claim 1, wherein:
the image summarization processing sets a summary candidate image sequence that includes summary images among the plurality of images included in the image sequence acquired by the image sequence acquisition processing that have been determined to be allowed to remain based on the coverage ratio, and sets a deletion candidate image sequence that includes deletion candidate images among the plurality of images included in the image sequence acquired by the image sequence acquisition processing that have been determined to be deleted based on the coverage ratio, and
the image summarization processing selects a first image from the summary candidate image sequence, selects a second image from the deletion candidate image sequence, sets an observation area within the second image, calculates a corresponding area that is an area within the first image that corresponds to the observation area based on the deformation information about the first image and the second image, and determines whether or not the second image can be deleted based on at least one of a first feature quantity calculated from the corresponding area and a second feature quantity calculated from the observation area.

24. The image processing device as defined in claim 23, wherein:
the first feature quantity is at least one of brightness information about the corresponding area, size information about the corresponding area, and similarity information about a similarity of the corresponding area with a given shape, and
the second feature quantity is at least one of the brightness information about the observation area, the size information about the observation area, and the similarity information about the similarity of the observation area with the given shape.

25. The image processing device as defined in claim 24, wherein the image summarization processing determines whether or not the second image can be deleted based on at least one comparison process among a first comparison process that compares the first feature quantity with a first threshold value, a second comparison process that compares the second feature quantity with a second threshold value, and a third comparison process that compares a degree of difference between the first feature quantity and the second feature quantity with a third threshold value.

26. The image processing device as defined in claim 23, wherein the image summarization processing calculates brightness information about the corresponding area as the first feature quantity based on a pixel value of each pixel included in the corresponding area, and calculates the brightness information about the observation area as the second feature quantity based on the pixel value of each pixel included in the observation area.

27. The image processing device as defined in claim 26, wherein the image summarization processing determines that the second image cannot be deleted when the first feature quantity that is the brightness information is larger than a given upper-limit threshold value, or when the first feature quantity is smaller than a given lower-limit threshold value.

28. The image processing device as defined in claim 23, wherein the image summarization processing calculates a value represented by size information about the corresponding area as the first feature quantity, and calculates a value represented by the size information about the observation area as the second feature quantity.

29. The image processing device as defined in claim 23, wherein the image summarization processing calculates a value that represents a similarity of the corresponding area with a given shape as the first feature quantity, and calculates a value that represents the similarity of the observation area with the given shape as the second feature quantity.

30. The image processing device as defined in claim 26, wherein the image summarization processing determines that the second image cannot be deleted when a degree of difference between the first feature quantity and the second feature quantity is larger than a given threshold value.

31. The image processing device as defined in claim 1, wherein the image summarization processing detects a scene change from the image sequence, sets a partial image sequence that includes images among the plurality of images included in the image sequence based on the detected scene change, selects the reference image and the determination target image from the partial image sequence, and determines whether or not the determination target image can be deleted based on the deformation information about the reference image and the determination target image.

32. The image processing device as defined in claim 31, wherein the image summarization processing detects the scene change based on accuracy information that represents accuracy of the deformation information that is used to determine whether or not the determination target image can be deleted.

33. The image processing device as defined in claim 32, wherein the image summarization processing determines whether or not each pixel included in a selected image among the plurality of images is suitable for calculation of the deformation information, calculates the accuracy information based on a number of pixels that have been determined to be suitable for calculation of the deformation information, and detects the scene change at a position corresponding to the selected image within the image sequence based on the calculated accuracy information.

34. The image processing device as defined in claim 33, wherein the image summarization processing sets an area that has a given size and includes a processing target pixel that is subjected to the determination as to suitability for calculation of the deformation information within the selected image, and determines whether or not the processing target pixel is suitable for calculation of the deformation information based on texture information about the set area.

35. The image processing device as defined in claim 32, wherein the image summarization processing calculates similarity information about a similarity between a first image among the plurality of images and a second image that immediately follows the first image as the accuracy information, and detects the scene change at a position between the first image and the second image within the image sequence based on the calculated accuracy information.

36. The image processing device as defined in claim 32, wherein the image summarization processing determines that the scene change has been detected when a value represented by the accuracy information is smaller than a given accuracy threshold value.

37. The image processing device as defined in claim 31, wherein the image summarization processing detects the scene change based on at least one of motion information calculated from the plurality of images, imaging information about a specific object, and brightness information.

38. The image processing device as defined in claim 31, wherein when the image summarization processing has detected an ith (i is an integer) scene change and an (i+1)th scene change that immediately follows the ith scene change from the image sequence, the image summarization processing sets images among the plurality of images included in the image sequence that follow the ith scene change and precede the (i+1)th scene change to be the partial image sequence.

39. The image processing device as defined in claim 31, wherein when the image summarization processing has set a plurality of the partial image sequences, the image summarization processing selects the reference image and the determination target image from the plurality of partial image sequences in parallel, and determines whether or not the determination target image can be deleted based on the deformation information about the reference image and the determination target image.

40. The image processing device as defined in claim 39, wherein when the image summarization processing has detected a jth (j is an integer) scene change from the image sequence, the image summarization processing sets a kth (k is an integer) partial image sequence that includes images among the plurality of images included in the image sequence that precede the jth scene change, and a (k+1)th partial image sequence that includes images among the plurality of images included in the image sequence that follow the jth scene change, and performs, in parallel, a process that selects the reference image and the determination target image from the kth partial image sequence, and determines whether or not the determination target image can be deleted based on the deformation information about the reference image and the determination target image, and a process that selects the reference image and the determination target image from the (k+1)th partial image sequence, and determines whether or not the determination target image can be deleted based on the deformation information about the reference image and the determination target image.

41. An image processing device comprising:
a CPU which executes a program stored in a memory to perform:
image sequence acquisition processing that acquires an image sequence that includes a plurality of images; and
image summarization processing that deletes some of the plurality of images included in the image sequence acquired by the image sequence acquisition processing to acquire a summary image sequence, wherein the image summarization processing selects a reference image and a determination target image from the plurality of images, sets an observation area within the determination target image, calculates a corresponding area that is an area of the reference image that corresponds to the observation area based on deformation information about the reference image and the determination target image, and determines whether or not the determination target image can be deleted based on a detection result with respect to at least one of blown out highlights, blocked up shadows, a decrease in size that is not suitable for observation, and deformation with respect to at least one of the corresponding area and the observation area, the detection result being detected based on at least one of a first feature quantity calculated from the corresponding area and a second feature quantity calculated from the observation area.

42. A computer-readable storage device with an executable program stored thereon, wherein the program instructs a computer to function as:

an image sequence acquisition section that acquires an image sequence that includes a plurality of images; and a processing section that performs an image summarization process that deletes some of the plurality of images included in the image sequence acquired by the image sequence acquisition section to acquire a summary image sequence, wherein the processing section selects a reference image and a determination target image from the plurality of images, calculates a coverage ratio of the determination target image by the reference image based on deformation information about the reference image and the determination target image, and determines whether or not the determination target image can be deleted based on the coverage ratio.

43. A computer-readable storage device with an executable program stored thereon, wherein the program instructs a computer to function as:

an image sequence acquisition section that acquires an image sequence that includes a plurality of images; and a processing section that performs an image summarization process that deletes some of the plurality of images included in the image sequence acquired by the image sequence acquisition section to acquire a summary image sequence, wherein the processing section selects a reference image and a determination target image from the plurality of images, sets an observation area within the determination target image, calculates a corresponding area that is an area of the reference image that corresponds to the observation area based on deformation information about the reference image and the determination target image, and determines whether or not the determination target image can be deleted based on a detection result with respect to at least one of blown out highlights, blocked UP shadows, a decrease in size that is not suitable for observation, and deformation with respect to at least one of the corresponding area and the observation area, the detection result being detected based on at least one of a first feature quantity calculated from the corresponding area and a second feature quantity calculated from the observation area.

44. An image processing method comprising:

acquiring an image sequence that includes a plurality of images;

selecting a reference image and a determination target image from the plurality of images included in the image sequence;

calculating a coverage ratio of the determination target image by the reference image based on deformation information about the reference image and the determination target image;

determining whether or not the determination target image can be deleted based on the coverage ratio; and performing an image summarization process that deletes some of the plurality of images included in the image sequence based on a result of the determination as to whether or not the determination target image can be deleted to acquire a summary image sequence.

45. An image processing method comprising:

acquiring an image sequence that includes a plurality of images;

selecting a reference image and a determination target image from the plurality of images included in the image sequence;

setting an observation area within the determination target image, and calculating a corresponding area that is an area of the reference image that corresponds to the observation area based on deformation information about the reference image and the determination target image;

determining whether or not the determination target image can be deleted based on a detection result with respect to at least one of blown out highlights, blocked up shadows, a decrease in size that is not suitable for observation, and deformation with respect to at least one of the corresponding area and the observation area, the detection result being detected based on at least one of a first feature quantity calculated from the corresponding area and a second feature quantity calculated from the observation area; and performing an image summarization process that deletes some of the plurality of images included in the image sequence based on a result of the determination as to whether or not the determination target image can be deleted to acquire a summary image sequence.

* * * * *